US007825147B2

(12) United States Patent  (10) Patent No.: US 7,825,147 B2
Palle et al.                (45) Date of Patent:    Nov. 2, 2010

(54) INHIBITORS OF PHOSPHODIESTERASE TYPE-IV

(75) Inventors: Venkata P. Palle, Haryana (IN); Sarala Balachandran, Delhi (IN); Mohammad Salman, Haryana (IN); Gagan Kukreja, Delhi (IN); Nidhi Gupta, Delhi (IN); Abhijit Ray, Delhi (IN); Sunanda G. Dastidar, Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 951 days.

(21) Appl. No.: 10/930,569

(22) Filed: Aug. 30, 2004

(65) Prior Publication Data

US 2005/0075383 A1 Apr. 7, 2005

(51) Int. Cl.
*A61K 31/422* (2006.01)
*A61K 31/341* (2006.01)
*A61K 31/4525* (2006.01)
*A61K 31/454* (2006.01)
*A61K 31/496* (2006.01)
*C07D 261/04* (2006.01)
*C07D 493/10* (2006.01)
*C07D 413/02* (2006.01)

(52) U.S. Cl. ............... 514/378; 514/317; 514/462; 514/254.02; 514/422; 544/367; 546/192; 546/209; 548/240; 548/518

(58) Field of Classification Search ............ 514/378, 514/462; 548/240; 549/472
See application file for complete search history.

(56) References Cited

U.S. PATENT DOCUMENTS

| | | | |
|---|---|---|---|
| 3,312,590 A | 4/1967 | Elks et al. | |
| 3,436,389 A | 4/1969 | Nathansohn et al. | |
| 3,506,694 A | 4/1970 | Oxley et al. | |
| 3,639,434 A | 2/1972 | Oxley et al | |
| 3,642,896 A | 2/1972 | Collin et al. | |
| 3,644,353 A | 2/1972 | Lunts et al. | |
| 3,652,554 A | 3/1972 | Anner et al. | |
| 3,700,681 A | 10/1972 | Barth | |
| 3,705,233 A | 12/1972 | Lunts et al. | |
| 3,721,687 A | 3/1973 | Elks et al. | |
| 3,780,177 A | 12/1973 | Ercoli et al. | |
| 3,928,326 A | 12/1975 | Brattsand et al. | |
| 3,929,768 A | 12/1975 | Brattsand et al. | |
| 3,937,838 A | 2/1976 | Wetterlin et al. | |
| 3,947,478 A | 3/1976 | Woods et al. | |
| 3,980,778 A | 9/1976 | Ayer et al. | |
| 3,983,233 A | 9/1976 | Brattsand et al. | |
| 3,992,534 A | 11/1976 | Brattsand et al. | |
| 3,994,974 A | 11/1976 | Murakami et al. | |
| 4,011,258 A | 3/1977 | Wetterlin et al. | |
| 4,014,909 A | 3/1977 | Torossian et al. | |
| 4,076,708 A | 2/1978 | Green et al. | |
| 4,081,541 A | 3/1978 | Bertelli | |
| 4,098,803 A | 7/1978 | Torossian et al. | |
| 4,115,589 A | 9/1978 | Lednicer | ..... 424/330 |
| 4,124,707 A | 11/1978 | Green et al. | |
| 4,158,055 A | 6/1979 | Sultz et al. | |
| 4,226,862 A | 10/1980 | Riva et al. | |
| 4,242,334 A | 12/1980 | Stache et al. | |
| 4,290,962 A | 9/1981 | Tachi et al. | |
| 4,298,604 A | 11/1981 | Hammell | |
| 4,335,121 A | 6/1982 | Phillipps et al. | |
| 4,419,364 A | 12/1983 | Olsson et al. | |
| 4,472,392 A | 9/1984 | Anderson et al. | |
| 4,472,393 A | 9/1984 | Shapiro | |
| 4,579,985 A | 4/1986 | Minderhoud et al. | |
| 4,587,236 A | 5/1986 | Annen et al. | |
| 4,619,921 A | 10/1986 | Kalvoda et al. | |
| 4,780,469 A | 10/1988 | Toda et al. | |
| 4,826,868 A | 5/1989 | Wachter et al. | |
| 4,859,692 A | 8/1989 | Bernstein et al. | |
| 4,873,259 A | 10/1989 | Summer, Jr. et al. | |
| 4,992,474 A | 2/1991 | Skidmore et al. | |
| 5,015,746 A | 5/1991 | Mizushima et al. | |
| 5,126,375 A | 6/1992 | Skidmore et al. | |
| 5,243,076 A | 9/1993 | Skidmore et al. | |
| 5,278,156 A | 1/1994 | Mizushima et al. | |
| 5,482,934 A | 1/1996 | Calatayud et al. | |
| 5,565,473 A | 10/1996 | Belley et al. | |
| 5,583,152 A | 12/1996 | Bernstein et al. | |

(Continued)

FOREIGN PATENT DOCUMENTS

EP    0 387 941    9/1990

(Continued)

OTHER PUBLICATIONS

Fihi et al. Abstract of Bulletin des Societes chimiques Beiges (1995), 104(1), p55-62 (STN serach report).*

(Continued)

*Primary Examiner*—Yong Chu

(57) ABSTRACT

The present invention relates to isoxazoline derivatives, which can be used as selective inhibitors of phosphodiesterase (PDE) type IV. In particular, compounds disclosed herein can be useful in the treatment of AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases in a patient, particularly in humans. The present invention also relates to processes for the preparation of disclosed compounds, as well as pharmaceutical compositions thereof, and their use as phosphodiesterase (PDE) type IV inhibitors.

6 Claims, No Drawings

U.S. PATENT DOCUMENTS

| | | | | |
|---|---|---|---|---|
| 5,686,434 | A | * 11/1997 | Kleinman | 514/92 |
| 5,710,170 | A | 1/1998 | Guay et al. | 514/332 |
| 5,712,298 | A | 1/1998 | Amschler | 514/352 |
| 5,837,699 | A | 11/1998 | Sequeira et al. | |
| 5,869,511 | A | 2/1999 | Cohan et al. | |
| 5,889,015 | A | 3/1999 | Sequeira et al. | |
| 5,976,573 | A | 11/1999 | Kim | |
| 6,057,307 | A | 5/2000 | Sequeira et al. | |
| 6,114,367 | A | 9/2000 | Cohan et al. | |
| 6,127,353 | A | 10/2000 | Yuen et al. | |
| 6,180,781 | B1 | 1/2001 | Yuen et al. | |
| 6,337,324 | B1 | 1/2002 | Harmenberg et al. | |
| 6,723,713 | B2 | 4/2004 | Sequeira et al. | |
| 7,183,321 | B2 | 2/2007 | Li et al. | |

FOREIGN PATENT DOCUMENTS

| | | |
|---|---|---|
| EP | 0 515 684 | 12/1992 |
| EP | 0 542 355 | 5/1993 |
| EP | 0 542 356 | 5/1993 |
| EP | 0 419 049 | 12/1995 |
| EP | 0 988 292 | 2/2003 |
| IN | 211/DEL/2005 | 2/2005 |
| IN | 1098/DEL/2005 | 5/2005 |
| JP | 11-071319 | 3/1999 |
| WO | WO 95/14680 | 6/1995 |
| WO | WO 95/14681 | 6/1995 |
| WO | WO 95/24398 | 9/1995 |
| WO | WO 01/90106 | 11/2001 |
| WO | WO 02/26723 | 4/2002 |
| WO | WO 02/32898 | 4/2002 |
| WO | WO 02/50070 | 6/2002 |
| WO | WO 02/081447 | 10/2002 |
| WO | WO 02/100332 | 12/2002 |
| WO | WO 2005/021515 | 3/2005 |
| WO | WO 2006/085212 | 8/2006 |
| WO | WO 2007/045979 | 4/2007 |
| WO | WO 2007/045980 | 4/2007 |

OTHER PUBLICATIONS

Co-pending U.S. Appl. No. 11/390,491, Mar. 2006, Palle, et al.*
Cited ref-STN-search-10930569.*
Vippagunta et al., Advanced Drug Delivery Reviews, vol. 48, p. 3-26 (p. 3), 2001.*
Sutherland and Roll, "The Relation of Adenosine-3',5'-Phosphate and Phosphorylase to the Actions of Catecholamines and Other Hormones", *Pharmacological Reviews*, 12:265-299 (1960).
Beavo and Reifsnyder, "Primary sequence of cyclic nucleotide phosphodiesterase isozymes and the design of selective inhibitors", *Trends in Pharmacological Sciences*, 11:150-155 (1990).
Nicholson et al., "Differential modulation of tissue function and theraputic potential of selective inhibitors of cyclic nucleotide phosphodiesterase isoenzymes", *Trends in Pharmacological Sciences*, 12:19-27 (1991).
Verghese et al, "Anti-Neutrophil Activity of Cyclic Nucleotide Phosphodiesterase Inhibitors with Varying Cardiotonic Potencies", *Journal of Molecular Cell Cardiology*, 12(suppl. II):S61 (1989).
Ashton et al., "Selective Type IV Phosphodiesterase Inhibitors as Antiasthmatic Agents. The Syntheses and Biological Activities of 3-(Cyclopentyloxy)-4-methoxybenzamides and Analogues", *Journal of Medicinal Chemistry*, 37:1696-1703 (1994).
DiSanto and Heaslip, "Identification and Stabilization of Large Molecular Weight PDE-IV from U937 Cells", *Biochemical and Biophysical Reasearch Communications*, 197(3):1126-1131 (1993).
Greene & Wuts, "Protecting Groups in Organic Synthesis", 3rd edition, 529-580 John Wiley & Sons, New York (1999).
Burnouf et al., "Synthesis, Structure-Activity Relationships, and Pharmacological Profile of 9-Amino-4-oxo-1-phenyl-3,4,6,7-tetrahydro[1,4]diazepino[6,7,1-*hi*]indoles: Discovery of Potent, Selective Phosphodiesterase Type 4 Inhibitors", *Journal of Medicinal Chemistry*, 43:4850-4867 (2000).•.

Fihi et al., "Reaction of methylene-.gamma.-butyrolactones with arly nitrile oxides. Unexpected bisadduct from 5-methylene-5H-furan-2-one", *Bulletin des Societes Chimiques Beiges*, 104(1):55-62 (1995) [Abstract].
Tian et al., "1,3-Dipolar Cycloaddition Reactions of Nitrile Oxides to Prop-1-ene-1,3- sultone" *Journal of Heterocyclic Chemistry*, 40(6):1071-1074 (2003).
Salgado-Zamora et al., "Oxidative degradation of arylfuro-1,2-oxazoles to arylnitriles by potassium permanganate" *Heterocyclic Communications House*, 7(3):209-212 (2001).
Hassikou et al., "Synthèse de nouveaux polyhétérocycles" *Tetrahedron Letters*, 42(34):5857-5861 (2001).
Syassi et al., "Nouvelle méthode de synthèse des 4,5-dihydroisoxazoles en milieu biphasique solide-liquide et par activation ultrasonique" *Tetrahedron Letters*, 40(40):7250-7209 (1999).
Subramanian et al., "Facile Synthesis of 3-Aroyl-3-Sulfolenes Through Cycloadditions of Arylnitrile Oxides & 3-Sulfolene" *Synthetic Communications*, 27(15):2557-2562 (1997).
Brahmeshwari et al., "Synthesis of 3-arylnaphth[2,3-*d*]-isoxazole-4,9-diones from Lawsone" *Indian Journal of Chemistry*, Section B, 34B(2):139-140 (1995).
Gaboury and Sibi, "Enantiocontrolled Synthesis of Burseran, Brassilignan, Dehydroxycubebin, and Other Tetrahydrofuran Lignans in Both Enantiomeric Forms. Application of Intermolecular Nitrile Oxide Cycloadditions and Lipase Mediated Kinetic Resolutions" *Journal of Organic Chemistry*, 58(8):2173-2180 (1993).
Brahmeshwari et al., "Synthesis and biological acivity of fused heterocycles derived from embelin" *Indian Journal of Chemistry*, Section B, 30B(3):369-370 (1991).
Awad and Sobhy, "1,3-Dipolar cycloaddition of nitrile oxides. II. Reactions with *o*-quinoid structures" *Canadian Journal of Chemistry*, 47(9):1473-1477 (1969).
Syassi et al., "Addition Dipolaire-1,3 des Arylnitriloxydes avec quelques Dipolarophiles Oléfiniques sur Alumine en Milieu sec et sous Micro-ondes", *Tetrahedron Letters*, 38(51):8855-8858 (1997).
Descacq et al., "Arylpyrazolines nitrofuraniques: synthèse et propriétés antibactériennes", *European Journal of Medicinal Chemistry*, 25(3):285-290 (1990).
Bisagni et al, "Synthesis of 3-aryl-4-acetyl-1H-pyrazolo[3,4-b]pyridines and 3-aryl-4-acetyl-1H-pyrazolo[4,3-c]pyridines" *Heterocycles*, 29(9):1815-1824 (1989).
Haiza, "Synthesis of some new 3,5-bisaryl-2-pyrazoline derivatives of expected antimicrobial activities", *Al-Azhar Bulletin of Science*, 8(2):445-454 (1997) [Abstract].
Varache-Beranger et al., "Thienylbenzofurans and arylthienylpyrazolines: synthesis and inhibitory effects on platelet aggregation in vitro", *Bulletin de la Societe de Pharmacie de Bordeaux*, 127(1-2-3-4):37-48 (1988) [Abstract].
Vanden Eynde and Mailleux, "Quaternary ammonium salt-assisted organic reactions in water: alkylation of phenols", *Synthetic Communications*, 31(1):1-7, (2001).
Guay et al., "Discovery of L-791,943: A Potent, Selective, Non Emetic and Orally Active Phosphodiesterase-4 Inhibitor", *Bioorganic and Medicinal Chemistry Letters*, 12(11):1457-1461 (2002).
Chauret et al., "Improving Metabolic Stability of Phosphodiesterase-4 Inhibitors Containing a Substituted Catechol: Prevention of Reactive Intermediate Formation and Covalent Binding", *Bioorganic and Medicinal Chemistry Letters*, 12(16):2149-2152 (2002).
Langlois, "Improvement of the synthesis of aryl difluoromethyl ethers and thioethers by using a solid-liquid phase-transfer technique", *Journal of Fluorine Chemistry*, 41(2):247-261 (1988).
Raju et al., "Conformationally restricted analogs of deoxynegamycin", *Bioorganic and Medicinal Chemistry Letters*, 14(12):3103-3107 (2004).
Vinick et al., "An Efficient Synthesis of 1-Phenyl-1-Piperidino-trans-4-Methylcyclohexane: Unanticipated Total Stereoselectivity in the Catalytic Hydrogenation of an Olefin", *Tetrahedron Letters*, 28(7):741-744 (1987).
King et al., "(±) 3-Amino-6-carboxamido-1,2,3,4-tetrahydrocarbazole: A Conformationally Restricted Analogue of 5-Carboxamidotryptamine with Selectivity for the Serotonin 5-HT$_{1D}$ Receptor", *Journal of Medicinal Chemistry*, 36(13):1918-1919 (1993).

Noguchi et al., "Total Synthesis and Absolute Configuration of Radiosumin, a Strong Trypsin Inhibitor From the blue-green Alga *Plectonema radiosum*", *Heterocycles*, 58:471-504 (2002).

U.S. Appl. No. 60/598,621. filed Aug. 4, 2004, Palle, et al.

U.S. Appl. No. 60/630,517, filed Nov. 23, 2004, Palle, et al.

Molina and de Aguiar, "Synthesis of new 4,5-dihydroisoxazoles with potential anti-inflammatory activity," *Heterocyclic Communications*, 9(5):535-538 (2003).

Rai and Hassner, "Intermolecular 1,3-dipolar cycloaddition of nitrile oxides with vinyl acetate and acrylonitrile," *Indian Journal of Chemistry, Section B: Organic Chemistry Including Medicinal Chemistry*, 36B(3):242-245 (1997)—Abstract Only.

Rai et al., "A Convenient Method of the Generation of Nitrile Oxide and its Application to the Synthesis of 2-Isoxazolines", *Organic Preparations and Procedures International*, 24(1):91-94 (1992).

Al-Timari and Fišera, "Regioselective Synthesis of *C*-nucleosides by 1,3-dipolar Cycloaddition of Arylnitrile Oxides to 5,6-dideoxy-1,2-*O*-isopropylidene-α-D-*xylo*-hex-5-enofuranose", *Carbohydrate Research*, 218:121-127 (1991).

Clerici et al., "Isothiazole Dioxides: Synthesis and Inhibition of *Trypanosoma brucei* Protein Farnesyltransferase", *Bioorganic & Medicinal Chemistry Letters*, 12(16):2217-2220 (2002).

Hafez et al., "New pyrazolines, isoxazolines and sulfides from 4,7-dimethoxy-5-acetyl-6-hydroxybenzofuran (Khellinone) and their antimicrobial activities", *Pakistan Journal of Scientific and Industrial Research*, 33(5-6):197-200 (1990)—Abstract Only.

Khalil et al., "Synthesis and microbial activity of 5-heterocyclo-8-hydroxyquinolines", *Journal of the Indian Chemical Society*, 67(10):821-823 (1990)—Abstract Only.

Koroleva et al., "Cycloreversion of 5-(4-pyridyl)-2-isoxazolines in reactions with bases", *Russian Journal of Organic Chemistry*, 33(1):108-112 (1997) (Translation of Zhurnal Organicheskoi Khimii—Abstract Only).

Zhang et al., "Phosphodiesterase-4 as a potential drug target", *Expert Opinion on Therapeutic Targets*, 9(6):1283-1305 (2005).

Houslay et al., "Keynote Review: Phosphodiesterase-4 as a therapeutic target", *Drug Discovery Today*, 10(22):1503-1519 (2005).

Lambrecht et al., "Pharmacology of Hexahydro-difeniodol Hexahydro-sila-difeniodol and Related Selective Muscarinic Antagonists", *Trends in Pharmaceutical Sciences*, 10, 60-65 (1989).

Birdsall et al., "Muscarinic Receptor Subclasses", *Trends in Pharmaceutical Sciences*, 4, 459-464 (1983).

Coruzzi, et al., "Gastric Antisecretory Activity of Telenzepine, A New $M_1$-Selective Muscarinic Antagonist: Comparison with Pirenzepine", *Arch Int Pharmacodyn Ther*, 302, 232-241 (1989).

Kawashima et al., Pharmacological Differentiation of Presynaptic $M_1$ Muscarinic Receptors Modulating Acetylcholine Release from Postsynaptic Muscarinic Receptors in guinea-Pig Ileum:, *Gen. Pharma.*, 21(1), 17-21 (1990).

Vippagunta et al., "Crystalline solids", *Advanced Drug Delivery Reviews*, 48:3-26 (2000).

Chawla and Bansal, "Challenges in Polymorphism of Pharmaceuticals", *CRIPS*, 5(1):9-12 (2004).

Newman and Byrn, "Solid-state Analysis of the Active Pharmaceutical Ingredient in Drug Products", *Drug Discovery Today*, 8(19):898-905 (2003).

Ankhiwala, et al., "A Facile Synthesis of Isoxazolines and Their Antimicrobial Activity", *Journal of the Institution of Chemists*, 61(5), 165-166 (1989) Abstract Only.

* cited by examiner

INHIBITORS OF PHOSPHODIESTERASE TYPE-IV

FIELD OF INVENTION

The present invention relates to isoxazoline derivatives, which can be used as selective inhibitors of phosphodiesterase (PDE) type IV. In particular, compounds disclosed herein can be useful in the treatment of AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases in a patient, particularly in humans. The present invention also relates to processes for the preparation of disclosed compounds, as well as pharmaceutical compositions thereof, and their use as phosphodiesterase (PDE) type IV inhibitors.

BACKGROUND OF INVENTION

It is known that cyclic adenosine-3',5'-monophosphate (cAMP) exhibits an important role of acting as an intracellular secondary messenger. The intracellular hydrolysis of cAMP to adenosine 5'-monophosphate (AMP) causes a number of inflammatory conditions, which include, but are not limited to, psoriasis, allergic rhinitis, shock, atopic dermatitis, Crohn's disease, adult respiratory distress syndrome (ARDS), eosinophilic granuloma, allergic conjunctivitis, osteoarthritis, and ulcerative colitis. Cyclic nucleotide phosphodiesterases (PDE), a biochemically and functionally, highly variable superfamily of the enzyme, is the most important factor in the control of cAMP (as well as of cGMP) levels. Eight distinct families with more than 15 gene products are currently recognized. Although PDE I, PDE II, PDE III, PDE IV, and PDE VII all use cAMP as a substrate, only the PDE IV and PDE VII types are highly selective for hydrolysis of cAMP. Accordingly, inhibitors of PDE, particularly the PDE IV inhibitors, such as rolipram or Ro-1724, are known as cAMP-enhancers. Immune cells contain PDE IV and PDE III, of which PDE IV is prevalent in human mononuclear cells. Thus, the inhibition of phosphodiesterase type IV has been a target for modulation and, accordingly, for therapeutic intervention in a range of disease processes.

The initial observation that xanthine derivatives, theophylline and caffeine inhibit the hydrolysis of cAMP led to the discovery of the required hydrolytic activity in the cyclic nucleotide phosphodiesterase (PDE) enzymes. More recently, distinct classes of PDE have been recognized, and their selective inhibition has led to improved drug therapy. Thus, it was recognized that inhibition of PDE IV could lead to inhibition of inflammatory mediator release and airway smooth muscle relaxation.

3-aryl-2-isoxazoline derivatives are known as anti-inflammatory agents and isoxazoline compounds are known as inhibitors of TNF release. However, there remains a need for new selective inhibitors of phosphodiesterase (PDE) type IV.

SUMMARY OF INVENTION

The present invention provides isoxazoline derivatives, which can be used for the treatment of AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases, and the processes for the synthesis of these compounds.

Pharmaceutically acceptable salts, pharmaceutically acceptable solvates, enantiomers, diastereomers or N-oxides of these compounds having the same type of activity are also provided.

Pharmaceutical compositions containing the compounds, which may also contain pharmaceutically acceptable carriers or diluents, can be used for the treatment of AIDS, asthma, arthritis, bronchitis, chronic obstructive pulmonary disease (COPD), psoriasis, allergic rhinitis, shock, atopic dermatitis, Crohn's disease, adult respiratory distress syndrome, eosinophilic granuloma, allergic conjunctivitis, osteoarthritis, ulcerative colitis and other inflammatory diseases.

The present invention encompasses a compound having the structure of Formula I,

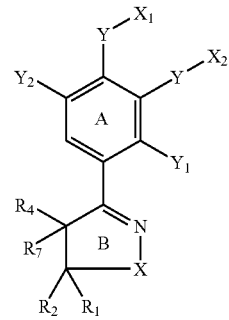

Formula I and its pharmaceutically acceptable salts, pharmaceutically acceptable solvates, enantiomers, diastereomers or N-oxides, wherein X can be oxygen;

$R_1$ can be hydrogen; alkyl; heterocyclyl; $(CH_2)_{1-4}$ OR', provided that $R_2$ also is $(CH_2)_{1-4}$OR'; —C(=O)$NR_xR_y$, provided that $R_2$ also is —C(=O)$NR_xR_y$; or —$(CH_2)_n$—C(=O)$R_3$;

$R_2$ can be —$(CH_2)_m$—C(=O)$R_3$; —$(CH_2)_{1-4}$ OR', provided $R_1$ also is $(CH_2)_{1-4}$OR'; —C(=O)$NR_xR_y$, provided $R_1$ also is —C(=O)$NR_xR_y$, or $R_1$ and $R_2$ together forms an optionally substituted cycloalkyl or heterocyclyl ring wherein the optional substituent is oxo, alkyl, alkenyl, alkynyl, halogen, nitro, —NH$_2$, —C(=O)$NR_xR_y$, —NHCOOR$_6$, cyano, hydroxy, alkoxy, or substituted amino;

$R_4$ can be hydrogen; alkyl; —OR$_5$; halogen; —NH$_2$, substituted amino; cyano; carboxy; or —C(=O)$NR_xR_y$; or $R_2$ and $R_4$ forms an optionally substituted 4-12 membered saturated or unsaturated monocyclic or bicyclic ring system fused to ring B having 0-4 heteroatom(s) selected from the group consisting of N, O and S, wherein the substituents is one or more of alkyl, halogen, hydroxy, alkoxy, —NH$_2$ or substituted amino, with the proviso that $R_2$ and $R_4$ together does not form —CH$_2$—O—CH$_2$—O—CH$_2$—;

$R_7$ can be hydrogen, alkyl, alkenyl, alkynyl, —OR$_5$, halogen, cyano, —NH$_2$ or substituted amino;

$X_1$ and $X_2$ each independently can be hydrogen, alkyl, alkaryl, cycloalkyl, heterocyclyl, heteroaryl, heterocyclylalkyl or heteroarylalkyl;

Y can be an oxygen atom; a sulphur atom; or —NR;

$Y_1$ and $Y_2$ each independently can be hydrogen; alkyl; —OR; —SR; or —NHR;

wherein any of $Y_1$ and $X_2$ & $X_1$ and $Y_2$ together optionally form a cyclic ring fused with the ring A, the ring containing 3-5 carbon atoms within the ring and having 1-3 heteroatoms such as N, O and S;

$X_1$ and $X_2$ can together optionally forms a cyclic ring fused with the ring A, the ring containing 3-5 carbon atoms within the ring and having 2-3 heteroatoms such as N, O and S, wherein the halogen can be F, Cl, Br, or I; R' can be alkyl, alkenyl, alkynyl, saturated or unsaturated cycloalkyl, aryl, heterocyclyl or heteroaryl; $R_x$ and $R_y$ each independently can be hydrogen, alkyl, $C_3$-$C_6$ alkenyl, $C_3$-$C_6$ alkynyl, cycloalkyl, —$SO_2R_5$, aryl, alkaryl, heteroaryl, heterocyclyl, heteroarylalkyl, and heterocyclylalkyl; m can be an integer between 0-2; $R_3$ can be optionally substituted $R_p$ or $R_q$; $R_6$ can be alkyl, alkenyl, alkynyl, cycloalkyl, alkaryl, heteroarylalkyl or heterocyclylalkyl; and R can be hydrogen, acyl, aryl, or alkyl; and wherein $R_5$ can be hydrogen, alkyl, alkenyl, alkynyl, aryl, cycloalkyl, alkaryl, heteroaryl, heteroarylalkyl, heterocyclyl or heterocyclylalkyl; $R_p$ can be heterocyclyl or heteroaryl ring, wherein the rings are attached to $(CH_2)_mC(=O)$ through N, and $R_q$ can be heterocyclyl or heteroaryl ring wherein the said rings are attached to —$(CH_2)_mC(=O)$ through C.

In some embodiments, Y can be oxygen or —NR; $Y_1$ and $Y_2$ are each independently hydrogen, alkyl or —OR. $X_1$ and $X_2$ are each independently methyl, ethyl, butyl, propyl, isopropyl, isobutyl, morpholinylmethyl, difluoromethyl, cyclopropylmethyl, cyclopentyl, cyclohexyl, cycloheptyl, indanyl, adamantyl and benzyl. In another embodiment, X and Y each independently can be oxygen, $X_1$ and $X_2$ are independently optionally substituted alkyl, cycloalkyl, heterocyclylalkyl or alkaryl; $R_1$ and $R_2$ each independently can be alkyl or —$(CH_2)_mC(=O)R_3$, wherein $R_3$ is $R_p$, or $R_1$ and $R_2$ can together join to form optionally substituted cycloalkyl and heterocyclyl ring; and $Y_1$, $Y_2$, $R_4$ and $R_7$ are each hydrogen.

$R_p$ can be an optionally substituted heterocyclyl ring selected from piperazinyl, piperidinyl, pyrrolidinyl, homopiperazinyl, or diaza-bicycloheptane. In another embodiment, $X_1$ and $X_2$ can together form a cycloalkyl ring selected from the group consisting of cyclohexyl, cyclobutyl and cyclopentyl; or a heterocyclyl ring selected from the group consisting of tetrahydrofuran, piperidine, pyrrolidine and tetrahydropyranyl. The optional substituents on $R_1$ and $R_2$ can be —$NH_2$, difluorophenylaminocarbonyl, dichlorophenylaminocarbonyl, indanedione, tertbutylcarbamate, carboxy, tert-butoxycarbonyl or chlorophenylsulphonamide-carbonyl.

In another embodiment, $X_1$ and $X_2$ may together form a cyclic ring fused with the ring A containing 3-5 carbon atoms within the ring and having 2-3 heteroatoms such as N and S.

The present invention also encompasses a compound having the structure of Formula I,

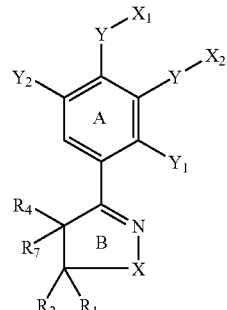

Formula I and its pharmaceutically acceptable salts, pharmaceutically acceptable solvates, enantiomers, diastereomers or N-oxides, wherein X can be $NR_7$ or S;

$R_7$ can be hydrogen or ($C_1$-$C_6$)-alkyl;

$R_1$ and $R_2$ each independently can be alkyl; alkenyl; alkynyl; alkoxy; hydroxy; cyano; nitro; halogen; heteroaryl; heterocyclyl; heteroarylalkyl; heterocyclylalkyl; —$NH_2$; substituted amino; carboxy; —$(CH_2)_m(C=O)R_3$; —$C(=O)NR_xR_y$; or —$(CH_2)_{1-4}OR'$, or $R_1$ and $R_2$ may together form optionally substituted cycloalkyl or heterocyclyl ring wherein the substituents of such a joint $R_1$-$R_2$ ring(s) can be oxo, alkyl, alkenyl, alkynyl, halogen, nitro, —$NH_2$, —$C(=O)NR_xR_y$, —$NHCOOR_6$, cyano, hydroxy, alkoxy, or substituted amino;

$R_4$ can be hydrogen; alkyl; halogen; —$OR_5$; cyano; carboxy; —$NH_2$, substituted amino, or —$C(=O)NR_xR_y$, or $R_2$ and $R_4$ may together form an optionally substituted 4-12 membered saturated or unsaturated monocyclic or bicyclic ring system fused to ring B having 0-4 heteroatoms, wherein the heteroatom is N, O or S, with the proviso that $R_2$ and $R_4$ together does not form —$CH_2$—O—$CH_2$—O—$CH_2$—, and wherein the substituents is one or more of alkyl, halogen, hydroxy, alkoxy, or amino;

$R_7$ can be hydrogen, alkyl, alkenyl, alkynyl, —$OR_5$, halogen, cyano, —$NH_2$ or substituted amino;

$X_1$ and $X_2$ each independently can be alkyl, cycloalkyl, alkaryl, heteroaryl, heterocyclyl, heteroarylalkyl or heterocyclylalkyl;

Y can be an oxygen atom; a sulphur atom; or —NR;

$Y_1$ and $Y_2$ each independently can be hydrogen; alkyl; —OR; —SR; or —NHR;

any of $Y_1$ and $X_2$ & $X_1$ and $Y_2$ optionally together form a cyclic ring fused with the ring A, the ring containing 3-5 carbon atoms within the ring and having 1-3 heteroatoms selected from the group consisting of N, O and S; and $X_1$ and $X_2$ can optionally together form a cyclic ring fused with the ring A shown in Formula I, the ring containing 3-5 carbon atoms within the ring and having 2-3 heteroatoms selected from the group consisting of N, O and S;

wherein the halogen can be F, Cl, Br, or I; $R_3$ can be optionally substituted $R_p$ or $R_q$; $R_6$ can be alkyl, alkenyl, alkynyl, cycloalkyl, alkaryl, heteroarylalkyl or heterocyclylalkyl; R can be hydrogen, acyl, aryl or alkyl; m can be an integer between 0-2; $R_3$ can be optionally substituted $R_p$ or $R_q$; R' can be alkyl, alkenyl, alkynyl, saturated or unsaturated cycloalkyl, aryl, heterocyclyl or heteroaryl; and $R_x$ and $R_y$ each independently can ve hydrogen, alkyl, $C_3$-$C_6$ alkenyl, $C_3$-$C_6$ alkynyl, cycloalkyl, —$SO_2R_5$, aryl, alkaryl, heteroaryl, heterocyclyl, heteroarylalkyl, and heterocyclylalkyl;

wherein $R_5$ can be hydrogen, alkyl, alkenyl, alkynyl, aryl, cycloalkyl, alkaryl, heteroaryl, heteroarylalkyl, heterocyclyl or heterocyclylalkyl; $R_p$ can be heterocyclyl or heteroaryl ring, wherein the rings are attached to $(CH_2)_mC(=O)$ through N, and $R_q$ can be heterocyclyl or heteroaryl ring wherein the said rings are attached to —$(CH_2)_mC(=O)$ through C.

The present invention further encompasses a compound which is selected from:

[3-(3-Cyclopentyloxy-4-methoxy phenyl)-5-(4-carboxylic acid tert butyl-ester-piperazin-1-yl-carbonyl)-4,5-dihydroisoxazol-5-yl)-({4-carboxylic-acid-tert butyl ester piperazine-1-yl)ethanone (Compound No. 1), 1-{1-[5-(4-Acetyl-4-phenyl-piperidine-1-carbonyl)-3-(3-cyclopentyloxy-4-methoxy-phenyl)-4,5-dihydro-isoxazole-5-yl]-4-acetyl-4-phenyl-piperidin-4-yl]-ethanone (Compound No. 2),

[3-(3-Cyclopentyloxy-4-methoxy-phenyl)-5-(pyrrolidine-1-carbonyl)-4,5-dihydro-isoxazol-5-yl]-pyrrolidin-1-yl-ethanone (Compound No. 3)

[3-(3-Cyclopentyloxy-4-methoxy-phenyl)-5-(piperidine-1-carbonyl)-4,5-dihydro-isoxazol-5-yl]-piperidin-1-yl-ethanone (Compound No. 4), 3-(3-Cyclopentyloxy-4-methoxy phenyl)-5-(pyrrolidin-2-carboxylic acid methyl ester-1-carbonyl)-4,5-dihydro-isoxazol-5-yl)-[{pyrrolidine-2-carboxylic acid methyl ester-5-yl]ethanone (Compound No 5),

[5-[4-(4-Chlorophenyl)-4-hydroxy-piperidine-1-carbonyl]-3-(3-cyclopentyloxy-4-methoxy-phenyl)-4,5-dihydro-isoxazol-5-yl]-[4-(4-chlorophenyl)-4-hydroxy-piperidin-1-yl]-ethanone (Compound No. 6),

[3-(3-Cyclopentyloxy-4-methoxy-phenyl)-5-(hydroxymethyl-piperidine-1-carbonyl)-4,5-dihydro-isoxazol-5-yl]-(4-hydroxymethyl-piperidin-1-yl)-ethanone (Compound No. 7),

[5-(5-Benzyl-2,5-diazabicyclo[2.2.1]heptane-2-(carbonyl)-3-(3-cyclopentyloxy-4-methoxy-phenyl]-,5-dihydro-isoxozol-5-yl]-5-benzyl-2,5-diazabicylo-[2.2.1]hept-2-yl-ethanone (Compound No 8),

[3-(3-Cyclopentyloxy-4-methoxy-phenyl)-5-methyl-4,5-dihydro-isoxazol-5-yl]-piperidin-1-yl-methanone (Compound No. 9), 4-[3-(3-Cyclopentyloxy-4-methoxy-phenyl)-5-methyl-4,5-dihydro-isoxazole-5-carbonyl]-piperazine-1-carboxylic acid tert-butyl ester (Compound No. 10), 1-[3-(3-Cyclopentyloxy-4-methoxy-phenyl)-5-methyl-4,5-dihydro-isoxazole-carbonyl]-pyrrolidin-2-carboxylic acid (Compound No. 11), 1-[3-(3-Cyclopentyloxy-4-methoxy-phenyl)-5-methyl-4,5-dihydro-isoxazol-5-carbonyl]-pyrrolidine-2-carboxylic acid methyl ester (Compound No. 12),

[3-(3-Cyclopentyloxy-4-methoxy-phenyl)-5-methyl-4,5-dihydro-isoxazole-5-yl]-pyrrolidin-1-yl-methanone (Compound No. 13),

[1-4]-Bipiperidinyl-1-yl-[3-(3-cyclopentyloxy-4-methoxy-phenyl)-5-methyl-4-,5-dihydro-isoxazol-5-yl]-methanone (Compound No. 14), 1-[3-(3-Cyclopentyloxy-4-methoxy-phenyl)-5-methyl-4,5-dihydro-isoxazole-5-carbonyl]-4-phenyl-piperidine-4-yl}-ethanone (Compound No. 15),

[3-(3-Cyclopentyloxy-4-methoxy-phenyl)-5-methyl-4,5-dihydro-isoxazol-5-yl]-(4-methyl-piperazin-1-yl)-methanone (Compound No. 16),

[3-(3-Cyclopentyloxy-4-methoxy-phenyl)-5-methyl-4,5-dihydro-isoxazol-5-yl]-piperazin-1-yl-methanone (Compound No. 17),

[4-(4-Chloro-phenyl)-4-hydroxy-piperidin-1-yl]-[3-(3-cyclopentyloxy-4-methoxy-phenyl)-5-methyl-4,5-dihydroisoxazol-5-yl]-methanone (Compound no. 18), {4-[3-(3-Cyclopentyloxy-4-methoxy-phenyl)-5-methyl-4,5-dihydro-isoxazole-5-carbonyl]-[1,4]diazepan-1-yl}-[3-(3-cyclopentyloxy-4-methoxy-phenyl)-5-methyl-4,5-dihydro-isoxazol-5-yl]-methanone (Compound No. 19),

[3-(3-Cyclopentyloxy-4-methoxy-phenyl)-5-methyl-4,5-dihydro-isoxazol-5-yl]-(4-cyclopropylmethyl-piperazin-1-yl)-methanone (Compound No. 20)

[3-(3-Cyclopentyloxy-4-methoxy-phenyl)-5-methyl-4,5-dihydro-isoxazol-5-yl]-(4-isobutyl-1-piperazin-1-yl)-methanone (Compound No. 21),

[3-Hydroxymethyl-piperidin-1-yl]-[3-(3-cyclopentyloxy-4-methoxy-phenyl)-5-methyl-4,5-dihydro-isoxazol-5-yl]-methanone (Compound No. 22),

[3-(3-Cyclopentyloxy-4-methoxy-phenyl)-5-methyl-4,5-dihydro-isoxazol-5-yl]-(4-hydroxy-piperidin-1-yl)-methanone (Compound No 23), (4-Benzyl-piperidin-1-yl)-[3-(3-cyclopentyloxy-4-methoxy-phenyl)-5-methyl-4,5-dihydro-isoxazol-5-yl]-methanone (Compound No 24), 1-[3-(3-Cyclopentyloxy-4-methoxy-phenyl)-5-methyl-4,5-dihydro-isoxazole-5-carbonyl]-piperidin-4-one (Compound No. 25),

[4-(4-Bromophenyl)-4-hydroxy-piperidin-1-yl]-[3-(3-cyclopentyloxy-4-methoxy-phenyl)-5-methyl-4,5-dihydroisoxazol-5-yl]-methanone (Compound No 26), (5-Benzyl-2,5-diaza-bicyclo[2.2.1]hept-2-yl-[3-(3-cyclopentyloxy-4-methoxy-phenyl)-5-methyl-4,5-dihydroisoxazol-5-yl]-methanone (Compound No. 27)

(4-Benzyl-piperazin-1-yl)-[3-(3-cyclopentyloxy-4-methoxy-phenyl)-5-methyl-4,5-dihydro-isoxazol-5-yl)-methanone (Compound No. 28), 1-[3-(3-Cyclopentyloxy-4-methoxy-phenyl)-5-methyl-4,5-dihydro-isoxazole-5-carbonyl]-pyrrolidin-2-carboxylic acid methyl amide (Compound No. 29), 1-[3-(3-Cyclopentyloxy-4-methoxy-phenyl)-5-methyl-4,5-dihydro-isoxazole-5-carbonyl]-pyrrolidine-2-carboxylic acid diethyl amide (Compound No. 30),

[3-(3-Cyclopentyloxy-4-methoxy-phenyl)-5-methyl-4,5-dihydro-isoxazol-5-yl]-(2-hydroxymethyl-pyrrolidin-1-yl)-methanone (Compound No. 31), 1-[3-(3-Cyclopentyloxy-4-methoxy-phenyl)-5-methyl-4,5-dihydroisoxazole-5-carbonyl]-piperidine-2-carboxylic acid methyl ester (Compound No. 32)

[3-(3-Cyclopentyloxy-4-methoxy-phenyl)-5-methyl-4,5-dihydro-isoxozole-5-carboxyl]-pyrrolidine-2-carboxylic acid amide (Compound No. 33), 3-[3-(3-Cyclopentyloxy-4-methoxy-phenyl)-5-methyl-4,5-dihydro-isoxazole-5-carbonyl]-bicyclo[2.2.1]heptan-2-one (Compound No. 34), 3-[3-Cyclopentyloxy-4-methoxy-phenyl)-1,7-dioxa-2-azaspiro[4.4]non-2-en-6-one (Compound No. 35), 3-[3-Cyclopentyloxy-4-methoxy-phenyl)-7-methyl-1-oxa-2,7-diaza-spiro[4.4]non-2-ene-6,9-dione (Compound No. 36),

[3-(3-Cyclopentyloxy-4-methoxy-phenyl)-5-methyl-4,5-dihydro-isoxazol-5-yl-(2-methoxymethyl-pyrrolidin-1-yl)-methanone (Compound No. 37)

3-(3-Cyclopentyloxy-4-methoxy-phenyl)-1,7-dioxa-2-aza-spiro[4.4]non-2-ene (Compound No. 38), 3-(3-Cyclopropylmethoxy-4-methoxy-phenyl)-1,7-dioxa-2-aza-spiro[4.4]non-2-ene (Compound No. 39), 3-(4-Difluoromethoxy-3-propoxy-phenyl)-1,7-dioxa-2-aza-spiro[4.4]non-2-ene (Compound No. 40), 3-(4-Difluoro-3-butoxy-phenyl)-1,7-dioxa-2-aza-spiro[4.4]non-2-ene (Compound No. 41), 3-(4-Difluoromethoxy-3-isobutoxy-phenyl)-1,7-dioxa-2-aza-spiro[4.4]non-2-ene (Compound No. 42), 3-(3-Cyclopropylmethoxy-4-difluoromethoxy-phenyl)-1,7-dioxa-2-aza-spiro[4.4]non-2-ene (Compound No. 43), 3-(3-Benzyloxy-4-difluoromethoxy-phenyl)-1,7-dioxa-2-aza-spiro[4.4]non-2-ene (Compound No. 44), 3-(4-Difluoromethoxy-3-cyclopentyloxy-phenyl)-1,7-dioxa-2-aza-spiro[4.4]non-2-ene (Compound No. 45), 3-(3,4-Bis-difluoromethoxy-phenyl)-1,7-dioxa-2-aza-spiro[4.4]non-2-ene (Compound No. 46), 3-(3-Butoxy-4-difluoromethoxy-phenyl)-1,7-dioxa-2-aza-spiro[4,4]non-2-ene (Compound No. 47), 3-[3-(Bicyclo[2.2.1]hept-2-yloxy)-4-difluoromethoxy-phenyl]-1,7-dioxo-2-aza-spiro[4.4]non-2-ene (Compound No. 48), 3-(4-Difluoromethoxy-3-methoxy-phenyl)-1,7-dioxa-2-aza-spiro[4,4]non-2-ene (Compound No. 49), 3-(4-Benzyloxy-3-methoxy-phenyl)-1,7-dioxa-2-aza-spiro[4.4]non-2-ene (Compound No. 50), 3-(3-Cycloheptyloxy-4-difluoromethoxy-phenyl)-1,7-dioxa-2-aza-spiro[4.4]non-2-ene (Compound No. 51), 4-(1,7-Dioxa-2-aza-spiro[4.4]non-2-en-3-yl)-2-methoxy-phenol (Compound No. 52), 3-[3-(indan-2-yloxy)-4-methoxy-phenyl]-1,7-dioxa-2-aza-spiro[4.4]non-2-ene (Compound No. 53)

3-(4-Ethoxy-3-methoxy-phenyl)-1,7-dioxa-2-aza-spiro[4.4]non-2-ene (Compound No. 54), 3-(3-Methoxy-4-propoxy-phenyl)-1,7-dioxa-2-aza-spiro[4.4]non-2-ene (Compound No. 55), 3-(4-Isopropoxy-3-methoxy-phenyl)-1,7-dioxa-2-aza-spiro[4.4]non-2-ene (Compound No. 56), 3-(4-Butoxy-3-methoxy-phenyl)-1,7-dioxa-2-aza-spiro[4.4]non-2-ene (Compound No. 57), 3-(4-Cyclopentyloxy-3-methoxy-phenyl)-1,7-dioxa-2-aza-spiro[4.4]non-2-ene (Compound No. 58), 3-(4-(Isobutoxy-3-methoxy-phenyl)-1,7-dioxa-2-aza-spiro[4.4]non-2-ene (Compound No. 59), 3-(4-Cyclohexyloxy-3-methoxy-phenyl)-1,7-dioxa-2-aza-spiro[4.4]non-2-ene (Compound No. 60), 3-(4-Cyclopropylmethoxy-3-methoxy-phenyl)-1,7-dioxa-2-aza-spiro[4.4]non-2-ene (Compound No. 61), 3-(3,4-Dimethoxy-phenyl)-1,7-dioxa-2-aza-spiro[4.4]non-2-ene (Compound No. 62), 3-(3-Ethoxy-4-methoxy-phenyl)-1,7-dioxa-2-aza-spiro[4.4]non-2-ene (Compound No. 63), 3-(4-Methoxy-3-propoxy-phenyl)-1,7-dioxa-2-aza-spiro[4.4]non-2-ene (Compound No. 64), 3-(3-Isopropoxy-4-methoxy-phenyl)-1,7-dioxa-2-aza-spiro[4.4]non-2-ene (Compound No. 65), 3-(3-Butoxy-4-methoxy-phenyl)-1,7-dioxa-2-aza-spiro[4.4]non-2-ene (Compound No. 66), 3-(3-Isobutoxy-4-methoxy-phenyl)-1,7-dioxa-2-aza-spiro[4.4]non-2-ene (Compound No. 67), 3-[4-Methoxy-3-(3-methyl-butoxy)-phenyl-1,7-dioxa-2-aza-spiro[4.4]non-2-ene (Compound No. 68), 3-(3-Cyclohexyloxy-4-methoxy-phenyl)-1,7-dioxa-2-aza-spiro[4.4]non-2-ene (Compound No. 69), 3-(3-Cycloheptyloxy-4-methoxy-phenyl)-1,7-dioxa-2-aza-spiro[4.4]non-2-ene (Compound No. 70), 3-[4-Methoxy-3-(2-morpholin-4-yl-ethoxy)-phenyl]-1,7-dioxa-2-aza-spiro[4.4]non-2-ene (Compound No. 71), 3-(3-Benzyloxy-4-methoxy-phenyl)-1,7-dioxa-2-aza-spiro[4.4]non-2-ene (Compound No. 72), 5-(1,7-Dioxa-2-aza-spiro[4.4]non-2-en-3-yl)-2-methoxy-phenol (Compound No. 73), 3-(3-Cyclopentyloxy-4-methoxy-phenyl)-1-oxa-2,8-diaza-spiro[4.5]dec-2-ene-8-carboxylic acid isopropyl ester (Compound No. 74), Hydrochloride salt of 3-(3-cyclopentyloxy-4-methoxy-phenyl)-1-oxa-2,8-diaza-spiro[4.5]dec-2-ene (Compound No. 75), 4-Chloro-N-[3-(3-cyclopentyloxy-4-methoxy-phenyl)-1-oxa-2,8-diaza-spiro[4.5]dec-2-ene-8-carbonyl]-benzene sulfonamide (Compound No. 76), 3-(3-Cyclopentyloxy-4-methoxy-phenyl)-1-oxa-2,8-diaza-spiro[4.5]dec-2-ene-8-carboxylic acid-(2,6-difluoro-phenyl)-amide (Compound No. 77), 3-(3-Cyclopentyloxy-4-methoxy-phenyl)-1-oxa-2,8-diaza-spiro[4.5]dec-2-ene-8-carboxylic acid-(2,4-dichloro-phenyl)-amide (Compound No. 78),

[3-(3-Cyclopentyloxy-4-methoxy-phenyl)-1-oxa-2-aza-spiro[4.5]dec-2-en-8-yl]-carbamic acid isopropyl ester (Compound No. 79), Hydrochloride salt of 3-(3-cyclopentyloxy-4-methoxy-phenyl)-1-oxa-2-aza-spiro[4.5]dec-2-en-8-ylamine (Compound No. 80), 2-[3-(3-Cyclopentyloxy-4-methoxy-phenyl)-1-oxa-2-aza-spiro[4.5]dec-2-en-8-yl]-isoindole-1,3-dione (Compound No. 81), 7-(3-Cyclopentyloxy-4-methoxy-phenyl)-5-oxa-6-aza-spiro[3.4]oct-6-ene (Compound No. 82), 3-(3-Cyclopentyloxy-4-methoxy-phenyl)-1-oxa-2-aza-spiro[4.5]dec-2-ene (Compound No. 83), 3-(3-Cyclopentyloxy-4-methoxy-phenyl)-1-oxa-2,7-diaza-spiro[4.4]non-2-ene-7-carboxylic acid tert-butyl ester (Compound No. 84), Hydrochloride salt of 3-(3-cyclopentyloxy-4-methoxy-phenyl)-1-oxa-2,7-diaza-spiro[4.4]non-2-ene (Compound No. 85).

The present invention also encompasses a pharmaceutical composition comprising a therapeutically effective amount of a compound of the present invention, together with a pharmaceutically acceptable carrier, excipient or diluent.

The present invention also encompasses a method of treating AIDS, asthma, arthritis, bronchitis, chronic obstructer pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis or other inflammatory diseases in an animal or human comprising administering to said animal or human a therapeutically effective amount of a compound of the present invention.

The present invention further encompasses a method of preventing, inhibiting or suppressing inflammatory condition in an animal or human comprising administering to said animal or human a therapeutically effective amount of a compound of the present invention.

The present invention encompasses a method for preparing a compound of Formula XI, its pharmaceutically acceptable salts, pharmaceutically acceptable solvates, enantiomers, diastereomers or N-oxides wherein the method comprises the steps of:

a. reacting a compound of Formula II with hydroxylamine hydrochloride in the presence of an acetate to form a compound of Formula III;

b. reacting the compound of Formula III with a compound of Formula IV to form a compound of Formula V;
c. hydrolyzing the compound of Formula V to form a compound of Formula VI;
d. reacting the compound of Formula VI with a compound of Formula VII, wherein Rp is

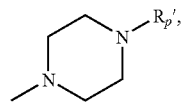

to form a compound of Formula IX; or reacting the compound of Formula VI with thionyl chloride to give a compound of Formula VIII, which can be reacted with a compound of Formula VII to form a compound of Formula IX;
e. deprotecting the compound of Formula IX to form Formula X; and
f. reacting the compound of Formula X with Hal-Rp', wherein Rp' is alkyl or acyl and Hal is halogen, to form a compound of Formula XI.

Preferably, the acetate is sodium acetate. In one embodiment, the compound of Formula V can be hydrolyzed in the presence of basic hydrolyzing agent. In another embodiment, the basic hydrolyzing agent is selected from the group consisting of sodium hydroxide, lithium hydroxide, potassium hydroxide and a mixture thereof. In another embodiment, the compound of Formula VI can be reacted with the compound of Formula VII in the presence of a condensing agent and in the presence of a base. In yet another embodiment, the condensing agent is selected from the group consisting of 1-(3-dimethylaminopropyl)-3-ethyl carbodiimide, dicyclohexyl carbodiimide and a mixture thereof, and the base is selected from the group consisting of 1,8-diazabicyclo[5.4.0]undec-7-ene, N-methylmorpholine, triethylamine, diisopropylamine, pyridine, and a mixture thereof. In another embodiment, the compound of Formula IX can be deprotected in the presence of a deprotecting agent, such as, for example, trifluoro acetic acid. In another embodiment, the compound of Formula VIII can be reacted with a compound of Formula VII in the presence of a base, such as, for example, triethylamine, diisopropylethylamine, pyridine, and a mixture thereof.

The present invention encompasses a method for preparing a compound of Formula XV or Formula XVI and its pharmaceutically acceptable salts, pharmaceutically acceptable solvates, enantiomers, diastereomers or N-oxides comprising the steps of:
a. reacting a compound of Formula III with a compound of Formula XII to form a compound of Formula XIII;
b. hydrolyzing the compound of Formula XIII to form a compound of Formula XIV; and
c. reacting the compound of Formula XIV with a compound of Formula VII to form a compound of Formula XVI, or
  reacting the compound of Formula XIV with methylamine to form a compound of Formula XVI.

In one embodiment, the hydrolysis of the compound of Formula XIII can be carried out in the presence of a basic hydrolyzing agent, such as, for example, sodium hydroxide, lithium hydroxide, potassium hydroxide, and a mixture thereof. In another embodiment, the reacting of the compound of Formula XIV with the compound of Formula VII can be carried out in the presence of an organic base, such as, for example, 1,8-diazabicyclo[5.4.0]undec-7-ene, N-methylmorpholine, diisopropylamine, pyridine, and a mixture thereof, and a condensing agent, such as, for example, 1-(3-dimethylaminopropyl)-3-ethyl carbodiimide hydrochloride, dicyclohexylcarbodiimide, and a mixture thereof.

The present invention also encompasses a method for preparing a compound of Formula XVIII and its pharmaceutically acceptable salts, pharmaceutically acceptable solvates, enantiomers, diastereomers or N-oxides comprising the step of reacting a compound of Formula III with a compound of Formula XVII to form a compound of Formula XVIII.

The present invention also encompasses a method for preparing a compound of Formula XXI and a compound of Formula XXII and its pharmaceutically acceptable salts, pharmaceutically acceptable solvates, enantiomers, diastereomers or N-oxides comprising the step of reacting a compound of Formula XIX with a compound of Formula XX, wherein Rz can be alkyl optionally substituted with halogen, to form a compound of Formula XXI and a compound of Formula XXII.

In one embodiment, the reaction of the compound of Formula XIX with the compound of Formula XX can be carried out in the presence of a phase transfer catalyst, such as, for example, benzyl triethyl ammonium chloride.

The present invention further encompasses a method of preparing a compound of Formula XXXI and a compound of XXXII and its pharmaceutically acceptable salts, pharmaceutically acceptable solvates, enantiomers, diastereomers or N-oxides comprising the steps of:
a. reacting a compound of Formula XXII, wherein Rz is alkyl optionally substituted with halogen, with a compound of Formula XXIII, wherein $Rz_1$ is alkyl, alkaryl, or cycloalkyl, to form a compound of Formula XXIV;
b. reacting the compound of Formula XXIV with hydroxylamine hydrochloride to form a compound of Formula XXV;
c. reacting the compound of Formula XXV with a compound of Formula XXVI, wherein P is alkyl or alkaryl, to form a compound of Formula XXVII;
d. hydrolyzing the compound of Formula XXVII to form a compound of Formula XXVIII;
e. reducing the compound of Formula XXVIII to form a compound of Formula XXIX;
f. cyclization of the compound of Formula XXIX to form a compound of Formula XXX; and
g. debenzylation of the compound of Formula XXX to form the compound of Formula XXXI, wherein Rz is benzyl and $Rz_1$ is alkyl optionally substituted with halogen, or debenzylation of the compound of Formula XXX to form the compound of Formula XXXII, wherein Rz is benzyl and $Rz_1$ is alkyl or cycloalkyl.

In one embodiment, the reaction of a compound of Formula XXII with a compound of Formula XXIII can be carried out in the presence of a base, such as, for example, potassium carbonate, sodium carbonate, sodium bicarbonate, and a mixture thereof. In another embodiment, the compound of Formula XXVII can be hydrolysed in the presence of a base, such as, for example, lithium hydroxide, sodium hydroxide, potassium hydroxide, and a mixture thereof. In yet another embodiment, the compound of Formula XXVIII can be reduced in the presence of a reducing agent, such as, for example, sodium borohydride, sodium cyanoborohydride, and a mixture thereof. In one embodiment, the compound of Formula XXIX undergoes cyclisation in the presence of a catalyst, such as, for example, triphenylphosphine, tri-tertbutyl phosphine, tri-cyclohexyl phosphine, and a mixture thereof.

In another embodiment, the compound of Formula XXX can be debenzylated to form the compound of Formula XXXI, wherein $Rz_1$ is benzyl and $R_z$ is alkyl optionally substituted with halogen, or Formula XXXII, wherein $Rz_1$ is benzyl and $R_z$ is alkyl or cycloalkyl, in the presence of a deprotecting agent, wherein the deprotecting agent is palladium on carbon.

The present invention also encompasses a method of preparing a compound of Formula XXXIIa and its pharmaceutically acceptable salts, pharmaceutically acceptable solvates, enantiomers, diastereomers or N-oxides comprising the step of debenzylation of a compound of Formula XXXII to form a compound of Formula XXXIIa, wherein $Z_3$ is benzyl and $R_x$ is alkyl or cycloalkyl.

In one embodiment, the debenzylation of the compound of Formula XXXII can be carried out in the presence of a deprotecting agent or under hydrogenation transfer conditions, including hydrogen and palladium on carbon and under ammonium formate and palladium on carbon.

The present invention also encompasses a method of preparing a compound of Formula XXXIV and its pharmaceutically acceptable salts, pharmaceutically acceptable solvates, enantiomers, diastereomers or N-oxides comprising the step of reacting a compound of Formula XXXI with a compound of Formula XXXIII to form a compound of Formula XXXIV.

In one embodiment, the reaction of a compound of Formula XXXI with a compound of Formula XXXIII can be carried out in the presence of base, such as, for example, potassium carbonate, sodium carbonate, sodium bicarbonate, and a mixture thereof.

The present invention further encompasses a method of preparing a compound of Formula XXXV and its pharmaceutically acceptable salts, pharmaceutically acceptable solvates, enantiomers, diastereomers or N-oxides comprising the step of reacting a compound of Formula XXXIIa with a compound of Formula XXXIII to form a compound of Formula XXXV.

In one embodiment, the reaction of a compound of Formula XXXIIa with a compound of Formula XXXIII can be carried out in the presence of a base, such as, for example, potassium carbonate, sodium carbonate, sodium bicarbonate, and a mixture thereof.

The present invention encompasses a method of preparing a compound of formula XXXIX and its pharmaceutically acceptable salts, pharmaceutically acceptable solvates, enantiomers, diastereomers or N-oxides comprising the steps of:

Scheme IX

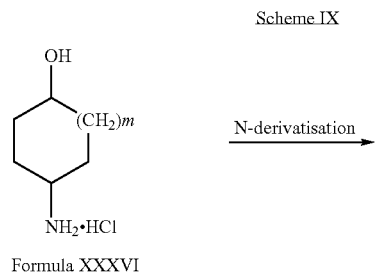

Formula XXXVI

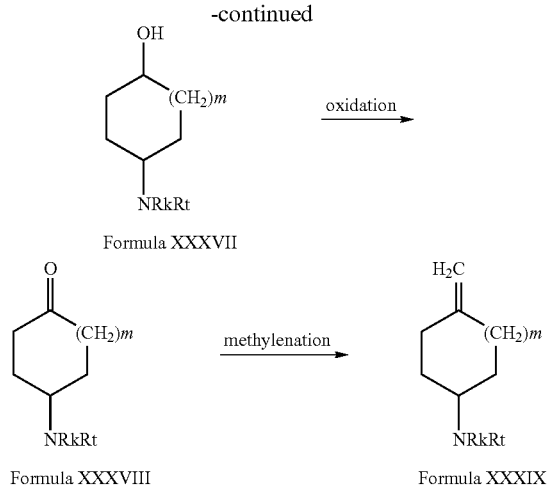

a. N-derivatization of a compound of Formula XXXVI to form a compound of Formula XXXVII, wherein Rk is hydrogen and Rt is —C(=O)OC(CH$_3$)$_3$ or Rk and Rt together joins to form

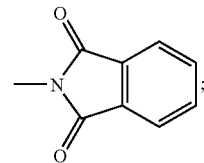

b. oxidation of the compound of Formula XXXVII to form a compound of Formula XXXVIII, wherein and Rt is —C(=O)OC(CH$_3$)$_3$; and c. methylenation of the compound of Formula XXXVIII to form a compound of Formula XXXIX.

In one embodiment, the compound of Formula XXXVI can be N-derivatised to form a compound of Formula XXXVII with tert-butyl dicarbonate and in the presence of a base, wherein the base is selected from the group consisting of triethylamine, diisopropylethylamine, N-methylmorpholine, pyridine, and a mixture thereof.

In one embodiment, the compound of Formula XXXVI can be N-derivatised to form a compound of Formula XXXVII (wherein Rk) with phthalic anhydride in an organic solvent. In another embodiment, the compound of Formula XXXVI can be N-derivatised to give a compound of Formula XXXVII in the presence of a base selected from the group consisting of triethylamine, diisopropylethylamine, N-methylmorpholine, pyridine, and a mixture thereof. In yet another embodiment, the oxidation of a compound of Formula XXXVII can be carried out in the presence of an oxidizing agent, wherein the oxidizing agent is selected from the group consisting of pyridinium chlorochromate, manganese dioxide, potassium permanganate, Jones reagent (CrO$_3$/H$_2$SO$_4$), and a mixture thereof.

In another embodiment, the methylenation of a compound of Formula XXXVIII can be carried out in the presence of Wittig salt, wherein the Wittig salt is selected from the group consisting of triphenylmethylphosphonium iodide, triphenylmethylphosphonium bromide, and a mixture thereof.

The present invention also encompasses a method of preparing a compound of Formula XLII and its pharmaceutically acceptable salts, pharmaceutically acceptable solvates, enantiomers, diastereomers or N-oxides comprising the steps of:
- a. reacting a compound of Formula XL with a compound of Formula XXV to form a compound of Formula XLI; and
- b. deprotecting the compound of Formula XLI to form a compound of Formula XLII.

In one embodiment, the reaction of a compound of Formula XL with a compound of Formula XXV can be carried out in the presence of a base, wherein the base is selected from the group consisting of pyridine, N-methylmorpholine, triethylamine, diisopropylethylamine, and a mixture thereof.

The present invention also encompasses a method of preparing a compound of Formula L and its pharmaceutically acceptable salts, pharmaceutically acceptable solvates, enantiomers, diastereomers or N-oxides comprising the steps of:
- a. N-protecting a compound of Formula XLIII to form a compound of Formula XLIV;
- b. oxidizing the compound of Formula XLIV to form a compound of Formula XLV;
- c. methylenation of the compound of Formula XLV to form a compound of Formula XLVI;
- d. reacting the compound of Formula XLVI with a compound of Formula XXV to form a compound of Formula XLVII;
- e. deprotecting the compound of Formula XLVII to form a compound of Formula XLVIII; and
- f. reacting the compound of XLVIII with a compound of Formula XLIX to form a compound of Formula L.

In one embodiment, the N-protection of the compound of Formula XLIII can be carried out in the presence of a base, wherein the base is selected from the group consisting of triethylamine, diisopropylethylamine, N-methylmorpholine, pyridine, and a mixture thereof.

In another embodiment, the oxidation of a compound of Formula XLIV can be carried out using an oxidizing agent, wherein the oxidizing agent is selected from the group consisting of pyridinium chlorochromate, manganese dioxide, potassium permanganate, Jones reagent ($CrO_3/H_2SO_4$), and a mixture thereof.

In yet another embodiment, the methylenation of a compound of Formula XLV can be carried out in the presence of a Wittig salt, wherein the Wittig salt is selected from the group consisting of triphenylmethyl-phosphonium iodide, triphenylmethylphosphonium bromide, and a mixture thereof.

In another embodiment, the reaction of a compound of Formula XLVI with a compound of Formula XXV can be carried out in the presence of a base, wherein the base is selected from the group consisting of pyridine, N-methylmorpholine, diisopropylethylamine, triethylamine, and a mixture thereof.

DETAILED DESCRIPTION OF THE INVENTION

In accordance with one aspect, the present invention encompasses a compound having the structure of Formula I

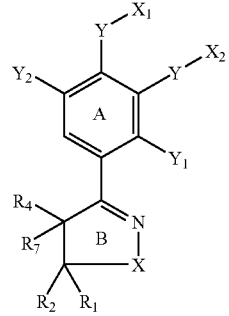

Formula I its pharmaceutically acceptable salts, pharmaceutically acceptable solvates, enantiomers, diastereomers or N-oxides wherein X can be oxygen;

$R_1$ can be hydrogen; alkyl; heterocyclyl; $(CH_2)_{1-4}$ OR', provided that $R_2$ is also $(CH_2)_{1-4}$ OR'; or —C(=O)$NR_xR_y$, provided that $R_2$ is also —C(=O)$NR_xR_y$; —$(CH_2)_m$—C(=O)$R_3$;

$R_2$ can be —$(CH_2)_m$C(=O)$R_3$; —$(CH_2)_{1-4}$ OR', provided $R_1$ is also $(CH_2)_{1-4}$OR'; —C(=O)$NR_xR_y$, provided $R_1$ is also —C(=O)$NR_xR_y$; or $R_1$ and $R_2$ may together form optionally substituted cycloalkyl or heterocyclyl ring wherein the substituents of such a joint $R_1$-$R_2$ ring(s) can be oxo, alkyl, alkenyl, alkynyl, halogen (e.g., F, Cl, Br, or I), nitro, —$NH_2$, —C(=O)$NR_xR_y$, —NHCOO$R_6$, cyano, hydroxy, alkoxy, or substituted amino;

$R_4$ can be hydrogen; alkyl; —OR$_5$; halogen (e.g., F, Cl, Br, or I); —$NH_2$, substituted amino; cyano; carboxy; or —C(=O)$NR_xR_y$, or $R_2$ and $R_4$ may together form optionally substituted 4-12 membered (un)saturated monocyclic or bicyclic ring system fused to ring B having 0-4 heteroatom(s) selected from N, O and S with the proviso that $R_2$ and $R_4$ together does not form —$CH_2$—O—$CH_2$—O—$CH_2$—, wherein the substituents can be one or more of alkyl, halogen (e.g., F, Cl, Br, or I), hydroxy, alkoxy, —$NH_2$ or substituted amino;

$R_7$ can be hydrogen, alkyl, alkenyl, alkynyl, —OR$_5$, halogen (e.g., F, Cl, Br, I), cyano, —$NH_2$ or substituted amino;

$X_1$ and $X_2$ each independently can be hydrogen, alkyl, alkaryl, cycloalkyl, heterocyclyl, heteroaryl, heteroarylalkyl or heterocyclylalkyl;

Y can be an oxygen atom; a sulphur atom; or —NR;

$Y_1$ and $Y_2$ independently can be hydrogen; alkyl; —OR; —SR; or —NHR;

any of $Y_1$ and $X_2$ & $X_1$ and $Y_2$ may together form a cyclic ring fused with the ring A shown in Formula I, the ring containing 3-5 carbon atoms within the ring and having 1-3 heteroatoms, such as N, O and S; and $X_1$ and $X_2$ can together form a cyclic ring fused with the ring A shown in Formula I, the ring containing 3-5 carbon atoms within the ring and having 2-3 heteroatoms, such as N, O and S, wherein R' can be alkyl, alkenyl, alkynyl, (un)saturated cycloalkyl, aryl, heterocyclyl or heteroaryl; $R_x$ and $R_y$ can be hydrogen, alkyl, alkenyl of three to six carbon atoms, alkynyl of three to six carbon atoms, cycloalkyl, —$SO_2R_5$, aryl, alkaryl, heteroaryl, heterocyclyl, heteroarylalkyl, and heterocyclylalkyl; m can be an integer in the range of 0-2; $R_3$ can be optionally substituted $R_p$ or $R_q$, wherein $R_p$ can be heterocyclyl or heteroaryl ring wherein the said rings are attached to $(CH_2)_m C(=O)$ through N, and $R_q$ can be heterocyclyl or heteroaryl ring, wherein the said rings can be attached to $-(CH_2)_m C(=O)$ through C; $R_6$ can be alkyl, alkenyl, alkynyl, cycloalkyl, alkaryl, heteroarylalkyl or heterocyclylalkyl; R can be hydrogen, acyl, aryl, or alkyl; and $R_5$ can be hydrogen, alkyl, alkenyl, alkynyl, aryl, cycloalkyl, alkaryl, heteroaryl, heteroarylalkyl, heterocyclyl or heterocyclylalkyl.

In accordance with another aspect, the present invention encompasses a compound having the structure of Formula I

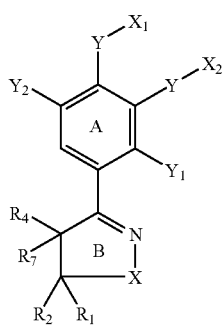

Formula I its pharmaceutically acceptable salts, pharmaceutically acceptable solvates, enantiomers, diastereomers or N-oxides wherein X can be $NR_7$ or S, wherein $R_7$ can be hydrogen or $(C_1$-$C_6)$-alkyl, i.e., lower alkyl;

$R_1$ and $R_2$ each independently can be alkyl; alkenyl; alkynyl; alkoxy; hydroxy; cyano; nitro; halogen (e.g., F, Cl, Br, I); heteroaryl; heterocyclyl; heteroarylalkyl; heterocyclylalkyl; $-NH_2$; substituted amino; carboxy; $-(CH_2)_m(C=O)R_3$; $-C(=O)NR_xR_y$; or $-(CH_2)_{1-4}OR'$; or $R_1$ and $R_2$ may together form optionally substituted cycloalkyl or heterocyclyl ring wherein the substituents of such a joint $R_1$-$R_2$ ring(s) can be oxo, alkyl, alkenyl, alkynyl, halogen (e.g., F, Cl, Br, I), nitro, $-NH_2$, $-C(=O)NR_xR_y$, $-NHCOOR_6$, cyano, hydroxy, alkoxy or substituted amino;

$R_4$ can be hydrogen; alkyl; halogen (e.g., F, Cl, Br, I); $-OR_5$; cyano; carboxy; $-NH_2$; substituted amino; or $-C(=O)NR_xR_y$, or $R_2$ and $R_4$ may together form optionally substituted 4-12 membered (un)saturated monocyclic or bicyclic ring system fused to ring B having 0-4 heteroatom(s), such as N, O and S, with the proviso that $R_2$ and $R_4$ together does not form $-CH_2-O-CH_2-O-CH_2-$, wherein the substituents can be one or more of alkyl, halogen (e.g., F, Cl, Br, I), hydroxy, alkoxy, or amino;

$R_7$ can be hydrogen, alkyl, alkenyl, alkynyl, $-OR_5$, halogen (e.g., F, Cl, Br, I), cyano, $-NH_2$ or substituted amino;

$X_1$ and $X_2$ each independently can be alkyl, cycloalkyl, alkaryl, heteroaryl, heterocyclyl, heteroarylalkyl or heterocyclylalkyl;

Y can be an oxygen atom; a sulphur atom; or $-NR$;

$Y_1$ and $Y_2$ each independently can be hydrogen; alkyl; $-OR$; $-SR$; or $-NHR$;

any of $Y_1$ and $X_2$ & $X_1$ and $Y_2$ may together form a cyclic ring fused with the ring A, the ring containing 3-5 carbon atoms within the ring and having 1-3 heteroatoms, such as N, O and S; and $X_1$ and $X_2$ may together form a cyclic ring fused with the ring A, the ring containing 3-5 carbon atoms within the ring and having 2-3 heteroatoms, such as N, O and S, wherein m can be an integer in the range of 0-2; $R_3$ can be optionally substituted $R_p$ or $R_q$, wherein $R_p$ can be heterocyclyl or heteroaryl ring wherein the said rings are attached to $(CH_2)_m C(=O)$ through N, and $R_q$ can be heterocyclyl or heteroaryl ring, wherein the said rings can be attached to $-(CH_2)_m C(=O)$ through C; $R_x$ and $R_y$ can be hydrogen, alkyl, alkenyl of three to six carbon atoms, alkynyl of three to six carbon atoms, cycloalkyl, $-SO_2R_5$, aryl, alkaryl, heteroaryl, heterocyclyl, heteroarylalkyl, and heterocyclylalkyl; R' can be alkyl, alkenyl, alkynyl, (un)saturated cycloalkyl, aryl, heterocyclyl or heteroaryl; $R_6$ can be alkyl, alkenyl, alkynyl, cycloalkyl, alkaryl, heteroarylalkyl or heterocyclylalkyl; $R_5$ can be hydrogen, alkyl, alkenyl, alkynyl, aryl, cycloalkyl, alkaryl, heteroaryl, heteroarylalkyl, heterocyclyl or heterocyclylalkyl; R can be group hydrogen, acyl, aryl or alkyl;

The following definitions apply to terms as used herein.

The term "alkyl," unless otherwise specified, refers to a monoradical branched or unbranched saturated hydrocarbon having from 1 to about 20 carbon atoms. This term is exemplified by groups, such as methyl, ethyl, n-propyl, iso-propyl, n-butyl, iso-butyl, t-butyl, n-hexyl, n-decyl, tetradecyl, and the like. The alkyl groups may be further substituted with one or more substituents such as alkenyl, alkynyl, alkoxy, cycloalkyl, acyl, acylamino, acyloxy, amino, aminocarbonyl, alkoxycarbonylamino, azido, cyano, halogen, hydroxy, oxo, thiocarbonyl, carboxy, arylthio, thiol, alkylthio, aryloxy, aminosulfonyl, aminocarbonylamino, hydroxyamino, alkoxyamino, nitro, $-S(O)_n R_5$ (wherein n can be 0, 1 or 2 and $R_5$ can be hydrogen, alkyl, alkenyl, alkynyl, aryl, cycloalkyl, alkaryl, heteroaryl, heteroarylalkyl, heterocyclyl or heterocyclylalkyl), heterocyclyl or heteroaryl. Unless otherwise constrained by the definition, all substituents may optionally be further substituted by 1-3 substituents chosen from alkyl, carboxy, aminocarbonyl, hydroxy, alkoxy, halogen, $-CF_3$, amino, substituted amino, cyano, and $-S(O)_n R_5$ (wherein n and $R_5$ are the same as defined earlier) or an alkyl group as defined above that is interrupted by 1-5 atoms or groups independently chosen from oxygen, sulfur and $-NR_a$-(where $R_a$ can be hydrogen, alkyl, cycloalkyl, alkenyl, alkynyl, or aryl). Unless otherwise constrained by the definition, all substituents may optionally be further substituted by 1-3 substituents chosen from alkyl, carboxy, aminocarbonyl, hydroxy, alkoxy, halogen, $CF_3$, amino, substituted amino, cyano, and $-S(O)_n R_5$ (wherein n and $R_5$ are the same as defined earlier); or an alkyl group as defined above that has both substituents as defined above and is also interrupted by 1-5 atoms or groups as defined above.

The term "alkenyl," unless otherwise specified, refers to a monoradical of a branched or unbranched unsaturated hydrocarbon group preferably having from 2 to 20 carbon atoms with cis or trans geometry. Preferred alkenyl groups include ethenyl or vinyl($CH=CH_2$), 1-propylene or allyl($-CH_2CH=CH_2$), or iso-propylene ($-C(CH_3)=CH_2$), bicyclo[2.2.1]heptene, and the like. In the event that the alkenyl is attached to a heteroatom, the double bond cannot be alpha to the heteroatom. The alkenyl group may be further substituted with one or more substituents, such as alkyl, alkenyl, alkynyl, alkoxy, cycloalkyl, acyl, acylamino, acyloxy, amino, aminocarbonyl, alkoxycarbonylamino, azido, cyano, halogen, hydroxy, oxo, thiocarbonyl, carboxy, arylthio, thiol, alkylthio, aryl, aryloxy, aminosulfonyl, aminocarbonylamino, hydroxyamino, alkoxyamino, nitro, —S(O)$_n$R$_5$ (wherein n and R$_5$ are the same as defined earlier), heterocyclyl or heteroaryl. Unless otherwise constrained by the definition, all substituents may be optionally further substituted by 1-3 substituents, which can be alkyl, carboxy, aminocarbonyl, hydroxy, alkoxy, halogen, —CF$_3$, amino, substituted amino, cyano, or —S(O)$_n$R$_5$ (wherein R$_5$ and n are the same as defined earlier).

The term "alkynyl," unless otherwise specified, refers to a monoradical of an unsaturated hydrocarbon, preferably having from 2 to 20 carbon atoms. Preferred alkynyl groups include ethynyl, (—C≡CH), or -propargyl (or propynyl, —CH$_2$C≡CH), and the like. In the event that the alkynyl is attached to a heteroatom, the triple bond cannot be alpha to the heteroatom. The alkynyl group may be further substituted with one or more substituents, such as alkyl, alkenyl, alkynyl, alkoxy, cycloalkyl, acyl, acylamino, acyloxy, amino, aminocarbonyl, alkoxycarbonylamino, azido, cyano, halogen, hydroxy, oxo, thiocarbonyl, carboxy, arylthio, thiol, alkylthio, aryl, aryloxy, aminosulfonyl, aminocarbonylamino, hydroxyamino, alkoxyamino, nitro, or —S(O)$_n$R$_5$ (wherein R$_5$ is the same as defined earlier). Unless otherwise constrained by the definition, all substituents may be optionally further substituted by 1-3 substituents, which can be alkyl, carboxy, aminocarbonyl, hydroxy, alkoxy, halogen, CF$_3$, amino, substituted amino, cyano, or —S(O)$_n$R$_5$ (wherein R$_5$ and n are the same as defined earlier).

The term "cycloalkyl," unless otherwise specified, refers to saturated or unsaturated cyclic alkyl groups of from 3 to 20 carbon atoms having a single cyclic ring or multiple condensed rings, which contains an optional olefinic bond. Such cycloalkyl groups include, by way of example, single ring structures, such as cyclopropyl, cyclobutyl, cyclopentyl, cyclooctyl, cyclopropylene, cyclobutylene and the like, or multiple ring structures, such as adamantanyl, and bicyclo[2.2.1]heptane, or cyclic alkyl groups to which is fused an aryl group, for example, indane and the like. The cycloalkyl may be further substituted with one or more substituents such as alkyl, alkenyl, alkynyl, alkoxy, cycloalkyl, acyl, acylamino, acyloxy, amino, aminocarbonyl, alkoxycarbonylamino, azido, cyano, halogen, hydroxy, oxo, thiocarbonyl, carboxy, arylthio, thiol, alkylthio, aryl, aryloxy, aminosulfonyl, aminocarbonylamino, hydroxyamino, alkoxyamino, nitro, —S(O)$_n$R$_5$ (wherein R$_5$ is the same as defined earlier), heteroaryl or heterocyclyl. Unless otherwise constrained by the definition, all substituents may be optionally further substituted by 1-3 substituents, which can be alkyl, carboxy, aminocarbonyl, hydroxy, alkoxy, halogen, CF$_3$, —NH$_2$, substituted amino, cyano, or —S(O)$_n$R$_5$ (wherein R$_5$ and n are the same as defined earlier).

The term "alkoxy" denotes the group O-alkyl, wherein alkyl is the same as defined above.

The term "alkaryl" refers to alkyl-aryl linked through alkyl portion (wherein alkyl is the same as defined earlier) and the alkyl portion contains carbon atoms from 1-6 and aryl is same as defined below.

The term "aryl," unless otherwise specified, refers to phenyl or naphthyl ring, and the like, optionally substituted with 1 to 3 substituents selected from the group consisting of halogen (such as F, Cl, Br, I), hydroxy, alkyl, alkenyl, alkynyl, cycloalkyl, alkoxy, aryloxy, —S(O)$_n$R$_5$ (wherein R$_5$ is the same as defined earlier), cyano, nitro, carboxy, heterocyclyl, heteroaryl, heterocyclylalkyl, heteroarylalkyl, acyl and (CH$_2$)$_{0-3}$C(=O)NR$_x$R$_y$ (wherein R$_x$ and R$_y$ are same as defined earlier).

The term "carboxy," unless otherwise specified, refers to —C(=O)O—R$_6$, wherein R$_6$ can be, for example, hydrogen, alkyl, alkenyl, alkynyl, cycloalkyl, alkaryl, heteroarylalkyl or heterocyclylalkyl.

The term "heteroaryl," unless otherwise specified, refers to an aromatic ring structure containing 5 or 6 carbon atoms, or a bicyclic aromatic group having 8 to 10 carbon atoms, with one or more heteroatom(s) independently selected from the group consisting of N, O and S, optionally substituted with 1 to 3 substituent(s), such as halogen (F, Cl, Br, I), hydroxy, alkyl, alkenyl, alkynyl, cycloalkyl, aryl, —S(O)$_n$R$_5$ (wherein n and R$_5$ are the same as defined earlier), alkoxy, alkaryl, cyano, nitro, acyl or C(=O)NR$_x$R$_y$ (wherein R$_x$ and R$_y$ are the same as defined earlier). Examples of heteroaryl groups include, but are not limited to, pyridinyl, pyridazinyl, pyrimidinyl, pyrrolyl, oxazolyl, thiazolyl, thienyl, isoxazolyl, triazinyl, furanyl, benzofuranyl, indolyl, benzothiazolyl, benzoxazolyl, and the like, including analogous oxygen, sulphur, and mixed hetero atom containing groups.

The term "heterocyclyl," unless otherwise specified, refers to a saturated or unsaturated monocyclic or polycyclic ring having 5 to 10 atoms, in which 1 to 3 carbon atoms in a ring are replaced by heteroatoms selected from the group consisting of O, S and N, and optionally are benzofused or fused heteroaryl of 5-6 ring members and/or optionally are substituted, wherein the substituents can be halogen (F, Cl, Br, I), hydroxy, alkyl, alkenyl, alkynyl, hydroxyalkyl, cycloalkyl, carboxy, aryl, alkoxy, alkaryl, heteroaryl, heterocyclyl, heteroarylalkyl, heterocyclylalkyl, oxo, alkoxyalkyl or —S(O)$_n$R$_5$ (wherein n and R$_5$ are the same as defined earlier), cyano, nitro, —NH$_2$ substituted amino, acyl or —C(=O)NR$_x$R$_y$ (wherein R$_x$ and R$_y$ are the same as defined earlier). Examples of heterocyclyl groups include, but are not limited to, tetrahydrofuranyl, dihydrofuranyl, azabicyclohexane dihydropyridinyl, piperidinyl, isoxazoline, piperazinyl, dihydrobenzofuryl, isoindole-dione, dihydroindolyl,

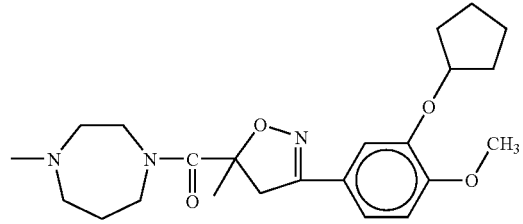

and the like.

"Heteroarylalkyl," unless otherwise specified, refers to an alkyl-heteroaryl group, wherein the alkyl and heteroaryl portions are the same as defined earlier.

"Heterocyclylalkyl," unless otherwise specified, refers to an alkyl-heterocyclyl group, wherein the alkyl and heterocyclyl portions of the group are the same as defined earlier.

The term "acyl" as defined herein refers to —C(=O)R", wherein R" is the same as defined earlier.

The term "substituted amino," unless otherwise specified, refers to a group —N(Rk)$_2$ wherein each R$_k$ can be hydrogen [provided that both R$_k$ groups are not hydrogen (defined as "—NH$_2$")], alkyl, alkenyl, alkynyl, alkaryl, cycloalkyl, aryl, heteroaryl, heterocyclyl, heterocyclylalkyl, heteroarylalkyl, acyl, S(O)$_m$R$_5$ (wherein m and R$_5$ is the same as defined above), —C(=O)NR$_x$R$_y$, —C(=O)OR$_x$ (wherein R$_x$ and R$_y$ are the same as defined earlier) or —NHC(=O)NR$_y$R$_x$ (wherein R$_y$ and R$_x$ are the same as defined earlier).

Unless otherwise constrained by the definition, all substituents optionally may be further substituted by 1-3 substituents, which can be alkyl, alkaryl, cycloalkyl, aryl, heteroaryl, heterocyclyl, carboxy, hydroxy, alkoxy, halogen, —CF$_3$, cyano, —C(=O)NR$_x$R$_y$, —O(C=O)NR$_x$R$_y$ (wherein R$_x$ and R$_y$ are the same as defined earlier) and —OC(=O)NR$_x$R$_y$, or —S(O)$_m$R$_5$ (where R$_5$ is the same as defined above and m is 0, 1 or 2).

The compounds of the present invention can be used for treating AIDS, asthma, arthritis, bronchitis, chronic obstructive pulmonary disease, psoriasis, allergic rhinitis, shock, atopic dermatitis, crohn's disease, adult respiratory distress syndrome, eosinophilic granuloma, allergic conjunctivitis, osteoarthritis, ulcerative colitis and other inflammatory diseases. Accordingly, the present invention encompasses a method of treating AIDS, asthma, arthritis, bronchitis, chronic obstructive pulmonary disease, psoriasis, allergic rhinitis, shock, atopic dermatitis, crohn's disease, adult respiratory distress syndrome, eosinophilic granuloma, allergic conjunctivitis, osteoarthritis, ulcerative colitis or other inflammatory diseases, which comprises administering to a patient in need thereof a therapeutically effective amount of an isoxazoline derivative compound of the present invention, and particularly an isoxazoline derivative compound of the present invention together a pharmaceutically acceptable carrier, excipient or diluent.

In accordance with yet another aspect, there are provided processes for the preparation of the compounds as described herein.

The compounds of the present invention may be prepared by techniques well known in the art. In addition, the compounds of the present invention may be prepared following a reaction sequence as depicted below.

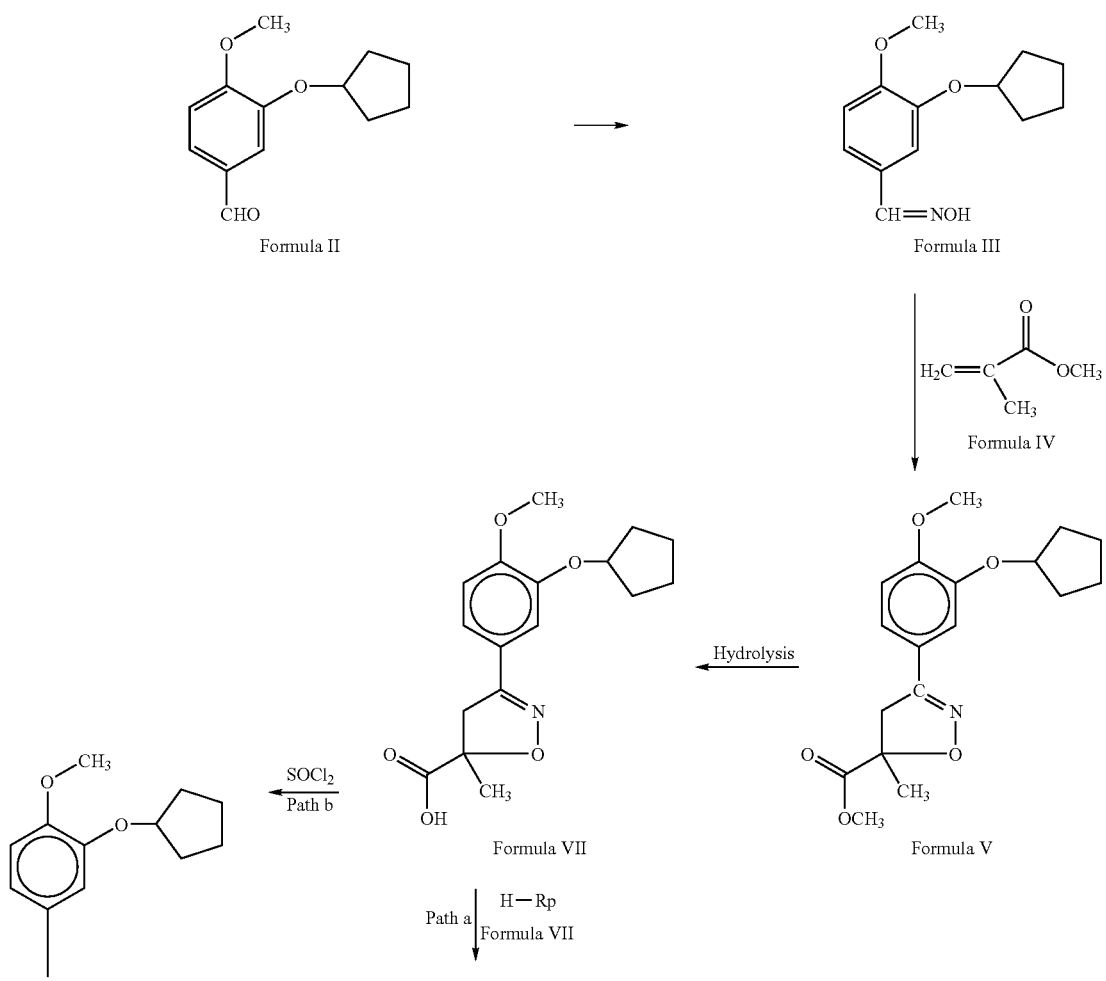

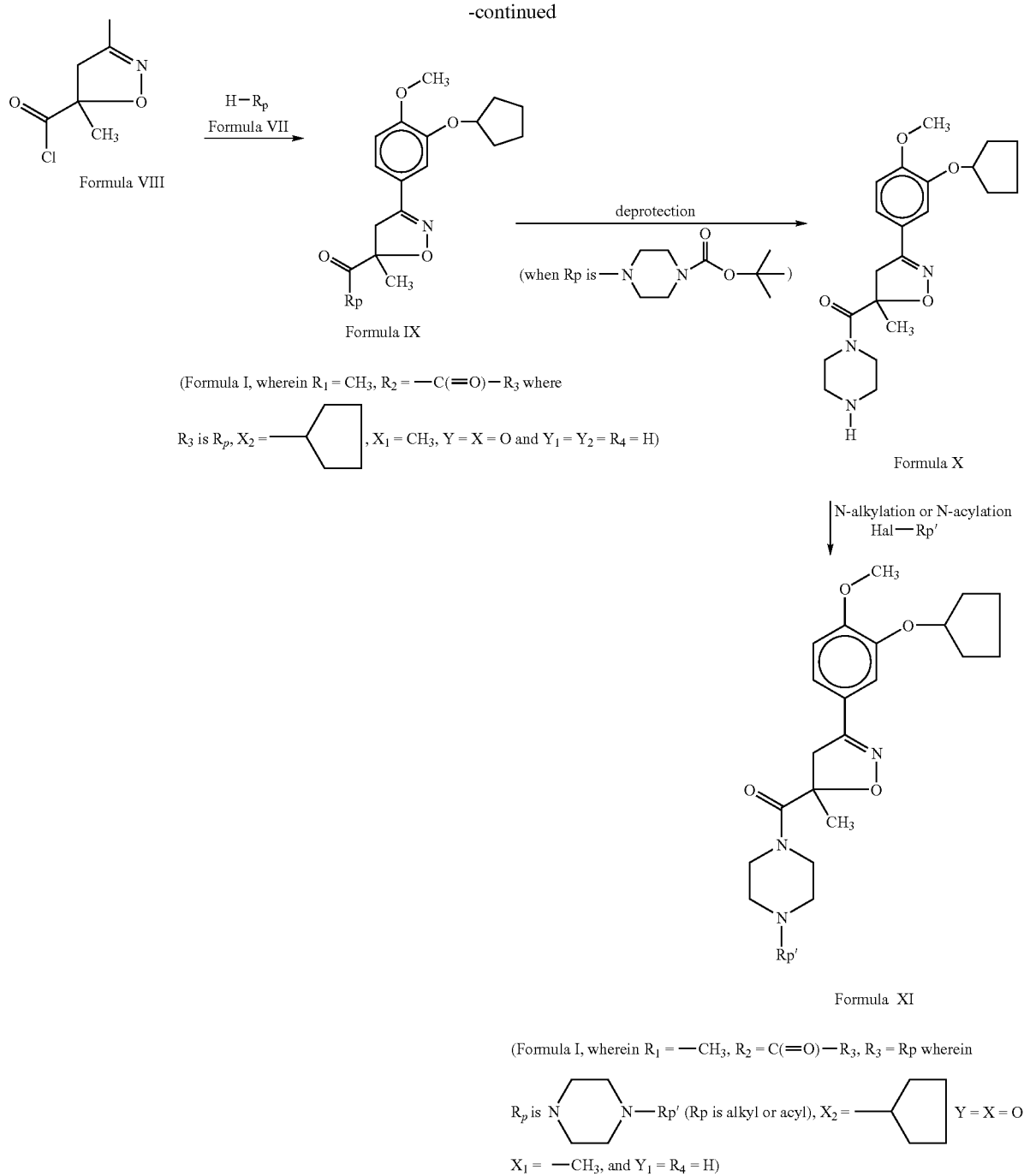

Compounds of Formula XI can be prepared by methods shown in Scheme I. Thus, a compound of Formula II is reacted with hydroxylamine hydrochloride in the presence of an acetate, such as sodium acetate, to yield the compound of Formula III, which can be further reacted with a compound of Formula IV to give a compound of Formula V, which can be hydrolysed to give a compound of Formula VI.

A compound of Formula VI (Path a) can be condensed with a compound of Formula VII to give a compound of Formula IX (Formula I, wherein $R_1$=$CH_3$, $R_2$=—C(=O)$R_3$ wherein $R_3$ can be $R_p$, Y and X can be O, $X_2$ can be cyclopentyl ring, $X_1$ can be —$CH_3$, and $Y_1$, $Y_2$, and $R_4$ can be H), which can be deprotected to give a compound of Formula X, which can be N-alkylated or acylated with a compound of Formula Hal-$R_p$, (wherein $R_p$, can be alkyl or acyl, for example, t-butylcarbonyl, and Hal is halogen) to furnish a compound of Formula XI (Formula I, $R_1$ can be —$CH_3$, $R_2$ can be —C(=O)$R_3$ where $R_3$ is $R_p$ ($R_p$ is

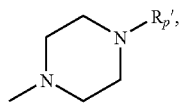

$X_2$ can be cyclopentyl ring, $X_1$ can be —$CH_3$ and $Y_1$, $Y_2$, and $R_4$ can be H).

Alternatively, a compound of Formula VI can be reacted with thionyl chloride (Path b) to give a compound of Formula VIII, which can be condensed with a compound of Formula VII to give a compound of Formula IX (Formula I, wherein $R_1$ can be $CH_3$, $R_2$ can be —C(=O)$R_3$, wherein $R_3$ can be $R_p$, Y and X can be O, $X_2$ can be cyclopentyl ring, $X_1$ can be —$CH_3$ and $Y_1$, $Y_2$ and $R_4$ can be H).

The reaction of compound of Formula III with a compound of Formula IV to give a compound of Formula V can be carried out in an organic solvent, such as, for example, tetrahydrofuran, dimethylformamide or dimethylsulphoxide. The hydrolysis of compound of Formula V to give a compound of Formula VI can be carried out in the presence of a basic hydrolyzing agent, such as, for example, sodium hydroxide, lithium hydroxide or potassium hydroxide. Alternatively, the hydrolysis of compound of Formula V to give a compound of Formula VI also can be carried out in the presence of acidic hydrolyzing agents, such as, for example dilute sulphuric acid, dilute hydrochloric acid or acetic acid.

The hydrolysis of compound of Formula V to give a compound of Formula VI can be carried out in an organic solvent, such as, for example, methanol, ethanol, propanol or isopropyl alcohol. The condensation of compound of Formula VI (Path a) with a compound of Formula VII to give a compound of Formula IX can be carried out in the presence of a condensing agent, such as, for example, 1-(3-dimethylaminopropyl)-3-ethyl carbodiimide hydrochloride (EDC.HCl) or dicyclohexyl carbodiimide (DCC).

The condensation of compound of Formula VI with a compound of Formula VII to give a compound of Formula IX can be carried out in the presence of a base, such as, for example 1,8-diazabicyclo[5.4.0]undec-7-ene (DBU), N-methylmorpholine (NMM), triethylamine, diisopropylethylamine or pyridine. The condensation of compound of Formula VI with a compound of Formula VII to give a compound Formula IX can be carried out in a organic solvent, such as, for example, dimethyl formamide, dimethylsulphoxide or tetrahydrofuran.

The compound of Formula IX can be deprotected to give a compound of Formula X with deprotecting agent, such as, for example, trifluoroacetic acid and in an organic solvent, such as, for example, dichloromethane, dichloroethane, chloroform or carbon tetrachloride. The compound of Formula X can be N-alkylated or acylated with a Compound of Formula Hal-$R_{p'}$ to give compound Formula XI in an organic solvent, such as, for example, dry acetone.

The compound of Formula VI (Path b) can be reacted with thionyl chloride to give a compound of Formula VIII in an organic solvent, such as, for example, dichloromethane, chloroform or carbon tetrachloride. The compound of Formula VIII can be condensed with a compound of Formula VII to give a compound of Formula IX in an organic solvent, such as, for example, tetrahydrofuran, dimethylformamide, or dimethylsulphoxide. The compound of Formula VIII can be condensed with a compound of Formula VII to give a compound of Formula IX in an organic base, such as, for example, triethylamine, diisopropylamine or pyridine.

Typical compounds prepared following the procedure as described in Scheme I, Path a include:

[3-(3-Cyclopentyloxy-4-methoxy-phenyl)-5-methyl-4,5-dihydro-isoxazol-5-yl]-piperdin-1-yl-methanone (Compound No. 9), 4-[3-(3-Cyclopentyloxy-4-methoxy-phenyl)-5-methyl-4,5-dihydro-isoxazole-5-carbonyl]-piperazine-1-carboxylic acid tert-butyl ester (Compound No. 10), 1-[3-(3-Cyclopentyloxy-4-methoxy-phenyl)-5-methyl-4,5-dihydro-isoxazole-carbonyl]-pyrrolidin-2-carboxylic acid (Compound No. 11), 1-[3-(3-Cyclopentyloxy-4-methoxy-phenyl)-5-methyl-4,5-dihydro-isoxazol-5-carbonyl]-pyrrolidine-2-carboxylic acid methyl ester (Compound No. 12),

[3-(3-Cyclopentyloxy-4-methoxy-phenyl)-5-methyl-4,5-dihydro-isoxazole-5-yl]-pyrrolidin-1-yl-methanone (Compound No. 13), 1-[3-(3-Cyclopentyloxy-4-methoxy-phenyl)-5-methyl-4,5-dihydro-isoxazole-5-carbonyl]-4-phenyl-piperidine-4-yl}-ethanone (Compound No. 15),

[3-(3-Cyclopentyloxy-4-methoxy-phenyl)-5-methyl-4,5-dihydro-isoxazol-5-yl]-(4-methyl-piperazin-1-yl)-methanone (Compound No. 16),

[3-(3-Cyclopentyloxy-4-methoxy-phenyl)-5-methyl-4,5-dihydro-isoxazol-5-yl]-piperazin-1-yl-methanone (Compound No. 17),

[4-(4-Chloro-phenyl)-4-hydroxy-piperidin-1-yl]-[3-(3-cyclopentyloxy-4-methoxy-phenyl)-5-methyl-4,5-dihydroisoxazol-5-yl]-methanone (Compound no. 18), {4-[3-(3-Cyclopentyloxy-4-methoxy-phenyl)-5-methyl-4,5-dihydro-isoxazole-5-carbonyl]-[1,4]diazepan-1-yl}-[3-(3-cyclopentyloxy-4-methoxy-phenyl)-5-methyl-4,5-dihydro-isoxazol-5-yl]-methanone (Compound No. 19),

[3-(3-Cyclopentyloxy-4-methoxy-phenyl)-5-methyl-4,5-dihydro-isoxazol-5-yl]-(4-cyclopropylmethyl-piperazin-1-yl)-methanone (Compound No. 20),

[3-(3-Cyclopentyloxy-4-methoxy-phenyl)-5-methyl-4,5-dihydro-isoxazol-5-yl]-(4-isobutyl-1-piperazin-1-yl)-methanone (Compound No. 21),

[3-Hydroxymethyl-piperidin-1-yl]-[3-(3-cyclopentyloxy-4-methoxy-phenyl)-5-methyl-4,5-dihydro-isoxazol-5-yl]-methanone (Compound No. 22),

[3-(3-Cyclopentyloxy-4-methoxy-phenyl)-5-methyl-4,5-dihydro-isoxazol-5-yl]-(4-hydroxy-piperidin-1-yl)-methanone (Compound No 23), (4-Benzyl-piperidin-1-yl)-[3-(3-cyclopentyloxy-4-methoxy-phenyl)-5-methyl-4,5-dihydro-isoxazol-5-yl]-methanone (Compound No 24), 1-[3-(3-Cyclopentyloxy-4-methoxy-phenyl)-5-methyl-4,5-dihydro-isoxazole-5-carbonyl]-piperidin-4-one (Compound No. 25),

[4-(4-Bromophenyl)-4-hydroxy-piperidin-1-yl]-[3-(3-cyclopentyloxy-4-methoxy-phenyl)-5-methyl-4,5-dihydro-isoxazol-5-yl]-methanone (Compound No 26), (5-Benzyl-2,5-diaza-bicyclo[2.2.1]hept-2-yl)-[3-(3-Cyclopentyloxy-4-methoxy-phenyl)-5-methyl-4,5-dihydro-isoxazol-5-yl]-(4-hydroxy-piperidin-1-yl)-methanone (Compound No. 27), (4-Benzyl-piperazin-1-yl)-[3-(3-cyclopentyloxy-4-methoxy-phenyl)-5-methyl-4,5-dihydro-isoxazol-5-yl)-methanone (Compound No. 28), 1-[3-(3-Cyclopentyloxy-4-methoxy-phenyl)-5-methyl-4,5-dihydro-isoxazole-5-carbonyl]-pyrrolidin-2-carboxylic acid methyl amide (Compound No. 29), 1-[3-(3-Cyclopentyloxy-4-methoxy-phenyl)-5-methyl-4,5-dihydroisoxazole-5-carbonyl]-pyrrolidine-2-carboxylic acid diethyl amide (Compound No. 30),

[3-(3-Cyclopentyloxy-4-methoxy-phenyl)-5-methyl-4,5-di-hydro-isoxazol-5-yl]-(2-hydroxymethyl-pyrrolidin-1-yl)-methanone (Compound No. 31), 1-[3-(3-Cyclopentyloxy-4-methoxy-phenyl)-5-methyl-4,5-dihydroisoxazole-5-carbonyl]-piperidine-2-carboxylic acid methyl ester (Compound No. 32),

[3-(3-Cyclopentyloxy-4-methoxy-phenyl)-5-methyl-4,5-di-hydro-isoxozole-5-carboxyl]-pyrrolidine-2-carboxylic acid amide (Compound No. 33), and

[3-(3-Cyclopentyloxy-4-methoxy-phenyl)-5-methyl-4,5-di-hydro-isoxazol-5-yl-(2-methoxy methyl-pyrrolidin-1-yl)-methanone (Compound No. 37).

Typical compounds prepared following the procedure as described in Scheme I, Path b include:

[1-4]-Bipiperidinyl-1-yl-[3-(3-cyclopentyloxy-4-methoxy-phenyl)-5-methyl-4-,5-dihydro-isoxazol-5-yl]-methanone (Compound No. 14).

Compounds of Formula XV can also be prepared by following the reaction sequence of Scheme II. Thus, a compound of Formula III can be reacted with a compound of Formula XII to give a compound of Formula XIII, which can be further hydrolysed to give a compound of Formula XIV. The compound of Formula XIV (Path a) either can be condensed with a compound of Formula VII to furnish a compound of Formula XV (Formula I, wherein $R_1$ can be $CH_3$, $R_2$ can be —$CH_2$—C(=O)$R_3$, wherein $R_3$ can be $R_p$, X and Y can be O, XI can be $CH_3$, $X_2$ can be cyclopentyl, and $Y_1$, $Y_2$ and $R_4$ can be H) in the presence suitable condensing agent and a suitable organic base or the compound of Formula XIV (Path b) is reacted with methylamine to furnish a compound of Formula XVI (Formula I, $R_1$ and $R_2$ together form

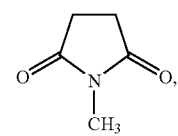

Y and X can be O, $Y_1$, $Y_2$ and $R_4$ can be H, $X_1$ can be $CH_3$, $X_2$ can be cyclopentyl).

Scheme II

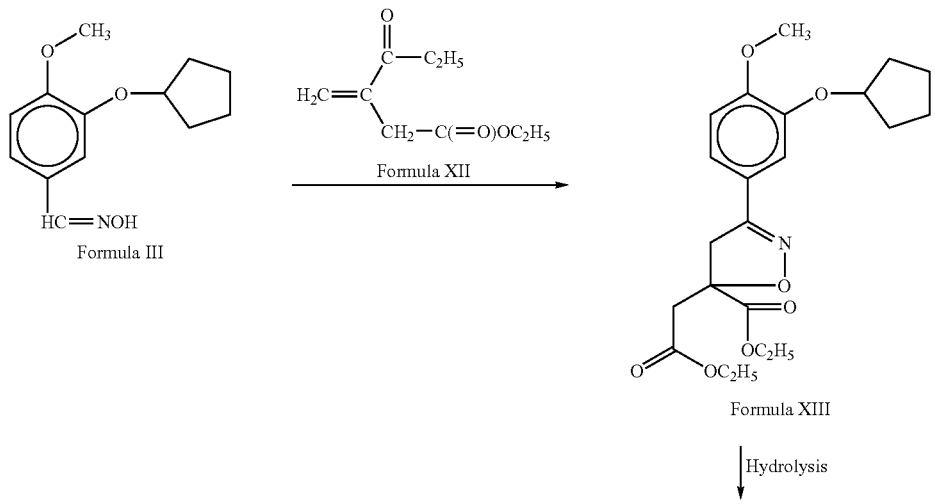

Formula XIII

↓ Hydrolysis

-continued

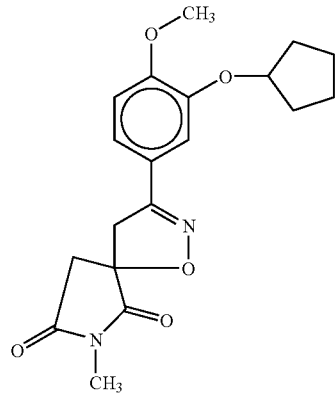

Formula XVI

Formula I, R₁ & R₂ together form , Y = X = O, $Y_1 = Y_2 = R_4 = H, X_1 = CH_3, X_2 = $ 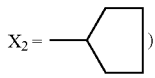 )

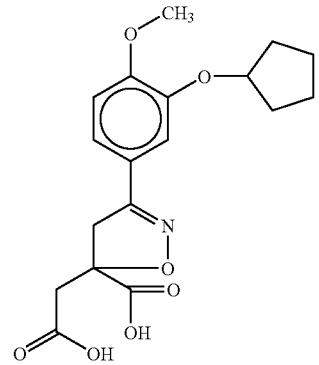

Formula XIV $\xleftarrow{\text{CH}_3\text{NH}_2}{\text{Path b}}$

Path a $\Big| \begin{array}{l} \text{H}-\text{R}_p \\ \text{Formula VII} \end{array}$

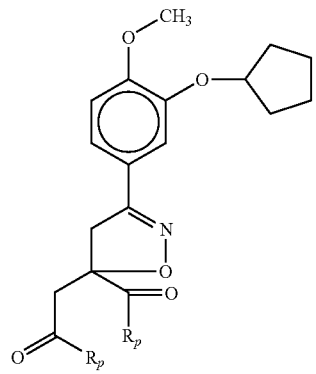

Formula XV (Formula I, $R_1 = $ —C(=O)—$R_3$, $R_2 = $ —CH₂—C(=O)—$R_3$ where $R_3$ is $R_p$ and m = 1, $Y_1 = Y_2 = R_4 = H$, Y = X = O, $X_1 = $ —CH₃ and $X_2 = $ 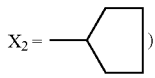 )

The reaction of compound of Formula III with compound of Formula XII to give a compound of Formula XIII can be carried out in an organic solvent, such as, for example, tetrahydrofuran, dimethylformamide or dimethylsulphoxide. The hydrolysis of compound of Formula XIII to give a compound of Formula XIV can be carried out in the presence of a basic hydrolyzing agent, such as, for example sodium hydroxide, lithium hydroxide or potassium hydroxide. The hydrolysis of compound of Formula XIII to give a compound of Formula XIV can be carried out in an suitable organic solvent, such as, for example methanol, ethanol, propanol or isopropyl alcohol.

Alternatively, hydrolysis of compound of Formula XIII to give a compound of Formula XIV can be carried out in the presence of a suitable acidic hydrolyzing agent, such as, for example, dilute sulfuric acid, dilute hydrochloric acid or acetic acid. The condensation of compound of Formula XIV with the compound of Formula VII (Path a) to give a compound of Formula XV can be carried out in the presence of a condensing agent, such as, for example, 1-(3-dimethylaminopropyl)-3-ethyl-carbodiimide-hydrochloride (EDC.HCl), dicyclohexyl carbodiimide (DCC). The condensation of compound of Formula XIV with the compound of Formula VII to give a compound of Formula XV can be carried out in the presence of an organic base, such as, for example 1,8-diazabicyclo [5.4.0]undec-7-ene (DBU), N-methylmorpholine, triethylamine, diisopropylamine or pyridine.

The condensation of compound of Formula XIV with the compound of Formula VII to give a compound of Formula XV can be carried out in an organic solvent, such as, for example, tetrahydrofuran, dimethylsulphoxide or dimethylformamide. The condensation of compound of Formula XIV with amino methyl (Path b) to give a compound of Formula XVI can be carried out in an organic solvent, such as, for example, tetrahydrofuran, dimethylsulphoxide or dimethylformamide.

The compounds prepared following the procedure as described in Scheme II Path a include:

[3-(3-Cyclopentyloxy-4-methoxy phenyl)-5-(4-carboxylic acid tert butyl-ester-piperazin-1-yl-carbonyl)-4,5-dihydroisoxazol-5-yl)-({4-carboxylic-acid-tert butyl ester piperazine-1-yl) ethanone (Compound No. 1), 1-{1-[5-(4-Acetyl-4-phenyl-piperidine-1-carbonyl)-3-(3-cyclopentyloxy-4-methoxy-phenyl)-4,5-dihydro-isoxazole-5-yl]-4-acetyl-4-phenyl-piperidin-4-yl]-ethanone (Compound No. 2),

[3-(3-Cyclopentyloxy-4-methoxy-phenyl)-5-(pyrrolidine-1-carbonyl)-4,5-dihydro-isoxazol-5-yl]-pyrrolidin-1-yl-ethanone (Compound No. 3),

[3-(3-Cyclopentyloxy-4-methoxy-phenyl)-5-(piperidine-1-carbonyl)-4,5-dihydro-isoxazol-5-yl]-piperidin-1-yl-ethanone (Compound No. 4), 3-(3-Cyclopentyloxy-4-methoxy phenyl)-5-(pyrrolidin-2-carboxylic acid methyl ester-1-carbonyl)-4,5-dihydro-isoxazol-5-yl)-[{pyrrolidine-2-carboxylic acid methyl ester-5-yl]ethanone (Compound No 5),

[5-[4-(4-Chlorophenyl)-4-hydroxy-piperidine-1-carbonyl]-3-(3-cyclopentyloxy-4-methoxy-phenyl)-4,5-dihydro-isoxazol-5-yl]-[4-(4-chlorophenyl)-4-hydroxy-piperidin-1-yl]-ethanone (Compound No. 6),

[3-(3-Cyclopentyloxy-4-methoxy-phenyl)-5-(hydroxymethyl-piperidine-1-carbonyl)-4,5-dihydro-isoxazol-5-yl]-(4-hydroxymethyl-piperidin-1-yl)-ethanone (Compound No. 7), and

[5-(5-Benzyl-2,5-diazabicyclo[2.2.1]heptane-2-(carbonyl)-3-(3-cyclopentyloxy-4-methoxy-phenyl]-,5-dihydro-isoxozol-5-yl]-5-benzyl-2,5-diazabicylo-[2.2.1]hept-2-yl-ethanone (Compound No 8).

The compounds prepared following the procedure as described in Scheme II Path b include:

3-[3-Cyclopentyloxy-4-methoxy-phenyl)-7-methyl-1-oxa-2,7-diaza-spiro[4.4]non-2-ene-6,9-dione (Compound No. 36).

Scheme III

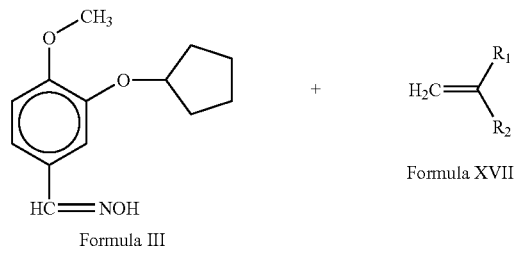

Formula III

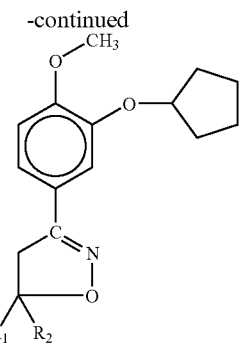

Formula XVIII (Formula I where $R_1$ and $R_2$ together forms a monocyclic or bicyclic ring system having 0-4 heteroatoms optionally substitited by one or more oxo, $Y = X = O$, $X_1 = CH_3$, $X_2 =$ cyclopentyl ring, $Y_1 = Y_2 = R_4 = H$)

Compounds of Formula I can also be prepared by following the reaction sequence of Scheme III. Thus, the compound of Formula III can be reacted with the compound of Formula XVII to give a compound of Formula XVIII (Formula I, wherein $R_1$ and $R_2$ together form a monocyclic or bicyclic ring system having 0-4 heteroatoms optionally substituted by one or more of oxo, X and Y can be O, XI can be $CH_3$, $X_2$ can be cyclopentyl ring, $Y_1$, $Y_2$, and $R_4$ can be H).

The reaction of compound of Formula III with a compound of Formula XVII to give a compound of Formula XVIII can be carried out in an organic solvent, such as, for example tetrahydrofuran, dimethylformamide or dimethylsulphoxide.

The compounds prepared following the procedure as described in Scheme III include:

3-[3-(3-Cyclopentyloxy-4-methoxy-phenyl)-5-methyl-4,5-dihydro-isoxazole-5-carbonyl]-bicyclo[2.2.1]heptan-2-one (Compound No. 34), and 3-[3-Cyclopentyloxy-4-methoxy-phenyl)-1,7-dioxa-2-aza-spiro[4.4]non-2-en-6-one (Compound No. 35).

Scheme IV

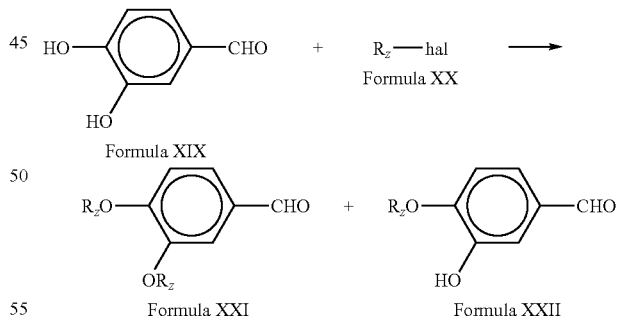

Compounds of Formulae XXI and XXII can also be prepared by following the reaction sequence of Scheme IV. Thus, the compound of Formula XIX can be reacted with a compound of Formula XX (wherein $R_z$ represents alkyl optionally substituted with halogen) to give a compound of Formula XXI and XXII.

The compound of Formula XIX can be reacted with a compound of Formula XX to give compounds of Formulae XXI and XXII in an organic solvent, such as, for example dimethylformamide, tetrahydrofuran, dioxane or diethylether in the presence of a phase transfer catalyst, such as, for example, benzyl triethylammonium chloride.

The compounds prepared following the procedure as described in Scheme IV include:
4-Difluoromethoxy-3-hydroxy-benzaldehyde, and
3,4-Bis-difluoromethoxy-benzaldehyde.

undergo ring cyclisation to give a compound of Formula XXX, which can undergo debenzylation to give a compound of Formula XXXI.

The reaction of compound of Formula XXII with a compound of Formula XXIII to give a compound of Formula XXIV can be carried out in an organic solvent, such as, for

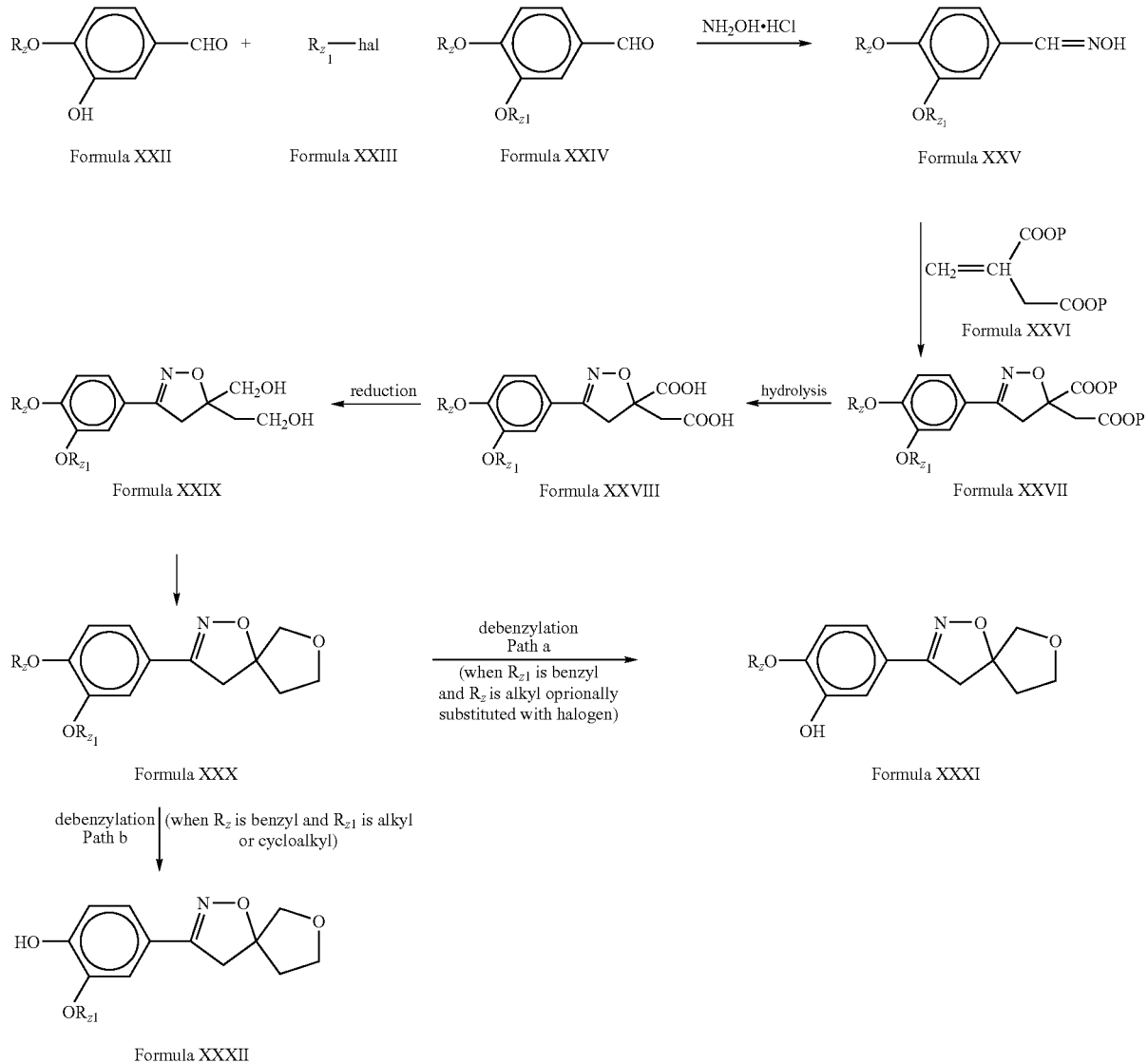

Compounds of Formulae XXX and XXXI can be prepared by following the reaction sequence of Scheme V. Thus, the compound of Formula XXII (wherein $R_z$ is the same as defined earlier) can be reacted with a compound of Formula XXIII (wherein $R_{z1}$ can be alkyl, alkaryl or cycloalkyl) to give a compound of Formula XXIV, which can be reacted with hydroxylamine hydrochloride to give a compound of Formula XXV, which can be reacted with a compound of Formula XXVI (wherein P can be alkyl or alkaryl) to give a compound of Formula XXVII, which can undergo hydrolysis to give a compound of Formula XXVIII, which can undergo reduction to give a compound of Formula XXIX, which can example, dimethylformamide, tetrahydrofuran, diethylether or dioxane, in the presence of base, such as, for example, potassium carbonate, sodium carbonate or sodium bicarbonate. The compound of Formula XXIV can be reacted with hydroxylamine hydrochloride to give a compound of Formula XXV in an organic solvent, such as, for example, ethanol, methanol, propanol or isopropyl alcohol. The compound of Formula XXV can be reacted with a compound of Formula XXVI to give a compound of Formula XXVII in an organic solvent, such as, for example, tetrahydrofuran, dimethylformamide, dioxane or diethylether. The hydrolysis of a compound of Formula XXVII to give a compound of Formula XXVIII can be carried out in a solvent system, such as, for example, tetrahydrofuran, methanol, dioxane or ethanol, in water in the presence of base, such as, for example, lithium hydroxide, sodium hydroxide or potassium hydroxide. The compound of Formula XXVIII can undergo reduction to give a compound of Formula XXIX in an organic solvent, such as, for example, tetrahydrofuran, dimethylformamide, dioxane or diethyl ether, with reducing agent, such as, for example, sodium borohydride or sodium cyanoborohydride. The compound of Formula XXIX can undergo ring cyclisation to give a compound of Formula XXX in an organic solvent, such as, for example tetrahydrofuran, dimethylformamide, dioxane or diethyl ether, with reagents, such as, for example, diisopropyldiazadicarboxylate (DIAD) or diethyldiazadicarboxylate (DEAD), in the presence of catalyst, such as, for example, triphenyl phosphine, tri-tertbutyl phosphine or tricyclohexyl phosphine. The compound of Formula XXX can be debenzylated (when $R_{z1}$ can be benzyl) to give a compound of Formula XXXI in an organic solvent, such as, for example, methanol, ethanol, propanol or isopropylalcohol, with a deprotecting agent, such as, for example, palladium on carbon.

The compounds prepared following the procedure as described in Scheme V include:

3-(3-Cyclopentyloxy-4-methoxy-phenyl)-1,7-dioxa-2-aza-spiro[4.4]non-2-ene (Compound No. 38), 3-(3-Cyclopropylmethoxy-4-methoxy-phenyl)-1,7-dioxa-2-aza-spiro[4.4]non-2-ene (Compound No. 39), 3-(4-Difluoromethoxy-3-propoxy-phenyl)-1,7-dioxa-2-aza-spiro[4.4]non-2-ene (Compound No. 40), 3-(4-Difluoro-3-butoxy-phenyl)-1,7-dioxa-2-aza-spiro[4.4]non-2-ene (Compound No. 41), 3-(4-Difluoromethoxy-3-isobutoxy-phenyl)-1,7-dioxa-2-aza-spiro[4.4]non-2-ene (Compound No. 42), 3-(3-Cyclopropylmethoxy-4-difluoromethoxy-phenyl)-1,7-dioxa-2-aza-spiro[4.4]non-2-ene (Compound No. 43), 3-(3-Benzyloxy-4-difluoromethoxy-phenyl)-1,7-dioxa-2-aza-spiro[4.4]non-2-ene (Compound No. 44), 3-(4-Difluoromethoxy-3-cyclopentyloxy-phenyl)-1,7-dioxa-2-aza-spiro[4.4]non-2-ene (Compound No. 45), 3-(3,4-Bis-difluoromethoxy-phenyl)-1,7-dioxa-2-aza-spiro[4.4]non-2-ene (Compound No. 46), 3-(3-Benzyloxy-4-methoxy-phenyl)-1,7-dioxa-2-aza-spiro[4.4]non-2-ene (Compound No. 72), and 5-(1,7-Dioxa-2-aza-spiro[4.4]non-2-en-3-yl)-2-methoxy-phenol (Compound No. 73).

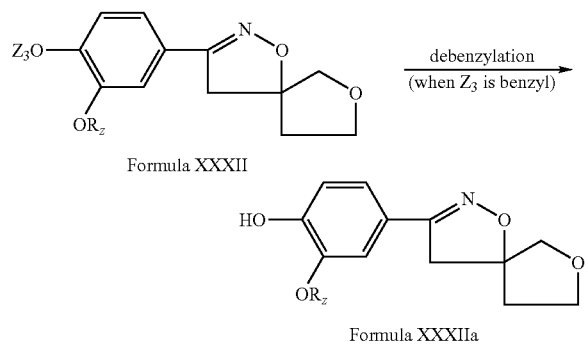

Formula XXXII

Formula XXXIIa

The compound of Formula XXXIIa can be prepared, for example, by reaction sequence as depicted in Scheme VI.

Thus, a compound of Formula XXXII can be debenzylated (wherein $Z_3$ can be benzyl) to give a compound of Formula XXXIIa.

The debenzylation of a compound of formula XXXII to give a compound of formula XXXIIa can be carried out in an organic solvent, such as, for example, methanol, ethanol, propanol or isopropylalcohol, with a deprotecting agent, such as, for example, using hydrogen and palladium on carbon or under catalytic hydrogenation transfer conditions of ammonium formate and palladium on carbon.

Particular compounds formed following the procedure described in Scheme VI include:

3-(4-Benzyloxy-3-methoxy-phenyl)-1,7-dioxa-2-aza-spiro[4.4]non-2-ene (Compound No. 50), and 4-(1,7-dioxa-2-aza-spiro[4.4]non-2-en-3-yl)-2-methoxy phenol (Compound No. 52).

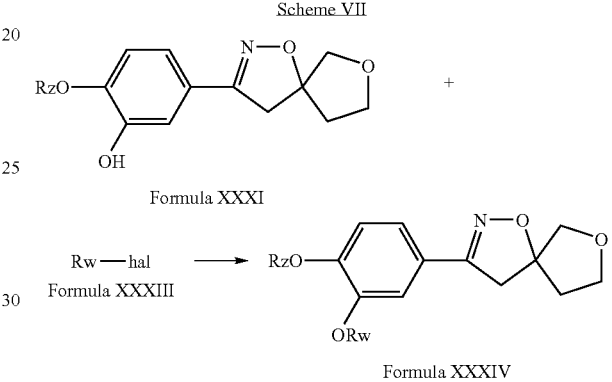

The compound of Formula XXXIV can be prepared by following the reaction sequence as depicted in Scheme VII. Thus, the compound of Formula XXXI can be reacted with a compound of Formula XXXIII (wherein $R_w$ can be alkyl or cycloalkyl and hal can be Br, Cl or I) to give a compound of Formula XXXIV.

The reaction of a compound of Formula XXXI with a compound of Formula XXXIII to give a compound of Formula XXXIV can be carried out in an organic solvent, such as, for example, dimethylformamide, tetrahydrofuran, diethyl-ether or dioxane, in the presence of base, such as, for example, potassium carbonate, sodium carbonate or sodium bicarbonate.

Particular compounds formed following the procedure shown in Scheme VII include:

3-(3-Butoxy-4-difluoromethoxy-phenyl)-1,7-dioxa-2-aza-spiro[4,4]non-2-ene (Compound No. 47), 3-[3-(Bicyclo[2.2.1]hept-2-yloxy)-4-difluoromethoxy-phenyl]-1,7-dioxo-2-aza-spiro[4.4]non-2-ene (Compound No. 48), 3-(4-Difluoromethoxy-3-methoxy-phenyl)-1,7-dioxa-2-aza-spiro[4.4]non-2-ene (Compound No. 49), 3-(3-Cycloheptyloxy-4-difluoromethoxy-phenyl)-1,7-dioxa-2-aza-spiro[4.4]non-2-ene (Compound No. 51), 3-[3-(indan-2-yloxy)-4-methoxy-phenyl]-1,7-dioxa-2-aza-spiro[4.4]non-2-ene (Compound No. 53)

3-(3,4-Dimethoxy-phenyl)-1,7-dioxa-2-aza-spiro[4.4]non-2-ene (Compound No. 62), 3-(3-Ethoxy-4-methoxy-phenyl)-1,7-dioxa-2-aza-spiro[4.4]non-2-ene (Compound No. 63), 3-(4-Methoxy-3-propoxy-phenyl)-1,7-dioxa-2-aza-spiro[4.4]non-2-ene (Compound No. 64), 3-(3-Isopropoxy-4-methoxy-phenyl)-1,7-dioxa-2-aza-spiro [4.4]non-2-ene (Compound No. 65), 3-(3-Butoxy-4-methoxy-phenyl)-1,7-dioxa-2-aza-spiro[4.4] non-2-ene (Compound No. 66), 3-(3-Isobutoxy-4-methoxy-phenyl)-1,7-dioxa-2-aza-spiro [4.4]non-2-ene (Compound No. 67), 3-[4-Methoxy-3-(3-methyl-butoxy)-phenyl-1,7-dioxa-2-aza-spiro[4.4]non-2-ene (Compound No. 68), 3-(3-Cyclohexyloxy-4-methoxy-phenyl)-1,7-dioxa-2-aza-spiro[4.4]non-2-ene (Compound No. 69), 3-(3-Cycloheptyloxy-4-methoxy-phenyl)-1,7-dioxa-2-aza-spiro[4.4]non-2-ene (Compound No. 70), 3-[4-Methoxy-3-(2-morpholin-4-yl-ethoxy)-phenyl]-1,7-dioxa-2-aza-spiro[4.4]non-2-ene (Compound No. 71), and 5-(1,7-Dioxa-2-aza-spiro[4.4]non-2-en-3-yl)-2-methoxy-phenol (Compound No. 73).

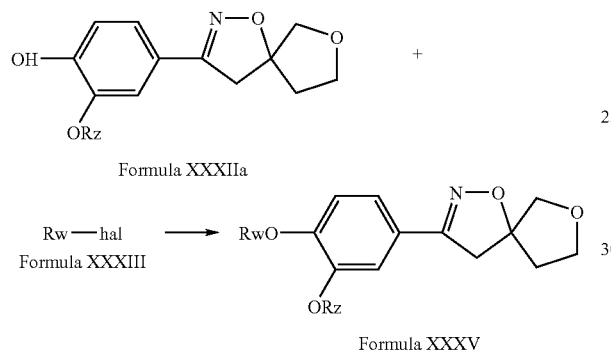

Formula XXXIIa

Formula XXXIII

Formula XXXV

The compound of Formula XXXV can be prepared by following the reaction sequence as depicted in Scheme VIII. Thus, a compound of Formula XXXIIa can be reacted with a compound of Formula XXXIII to give a compound of Formula XXXV.

The reaction of a compound of Formula XXXIIa with a compound of Formula XXXIII to give a compound of Formula XXXV can be carried out in an organic solvent, such as, for example, dimethylformamide, tetrahydrofuran, diethyl ether or dioxane, in the presence of a base, such as, for example, potassium carbonate, sodium carbonate or sodium bicarbonate.

Particular compounds formed following the procedure shown in Scheme VIII include:

3-(4-Ethoxy-3-methoxy-phenyl)-1,7-dioxa-2-aza-spiro[4.4] non-2-ene (Compound No. 54), 3-(3-Methoxy-4-propoxy-phenyl)-1,7-dioxa-2-aza-spiro [4.4]non-2-ene (Compound No. 55), 3-(4-Isopropoxy-3-methoxy-phenyl)-1,7-dioxa-2-aza-spiro [4.4]non-2-ene (Compound No. 56), 3-(4-Butoxy-3-methoxy-phenyl)-1,7-dioxa-2-aza-spiro[4.4] non-2-ene (Compound No. 57), 3-(4-Cyclopentyloxy-3-methoxy-phenyl)-1,7-dioxa-2-aza-spiro[4.4]non-2-ene (Compound No. 58), 3-(4-(Isobutoxy-3-methoxy-phenyl)-1,7-dioxa-2-aza-spiro [4.4]non-2-ene (Compound No. 59), 3-(4-Cyclohexyloxy-3-methoxy-phenyl)-1,7-dioxa-2-aza-spiro[4.4]non-2-ene (Compound No. 60), and 3-(4-Cyclopropylmethoxy-3-methoxy-phenyl)-1,7-dioxa-2-aza-spiro[4.4]non-2-ene (Compound No. 61).

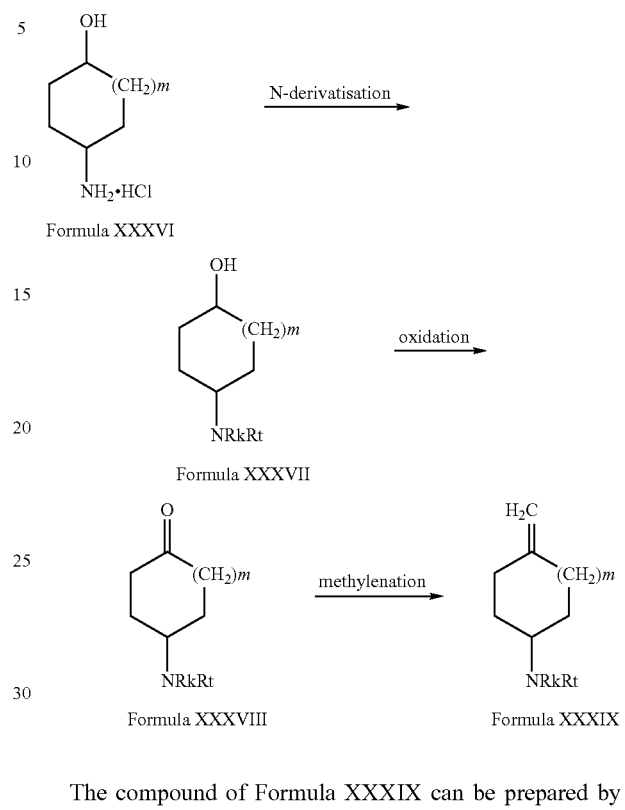

The compound of Formula XXXIX can be prepared by following the reaction sequence as depicted in Scheme IX. Thus, a compound of Formula XXXVI (wherein m can be 0 or 1) undergoes N-derivatization to give a compound of Formula XXXVII (wherein Rk can be hydrogen and Rt can be —C(=O)OC(CH$_3$)$_3$ or Rk and Rt together with nitrogen joins to form

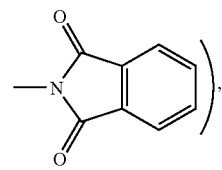

which can be oxidized to give a compound of Formula XXXVIII, which can further undergo methylenation reaction to give a compound of Formula XXXIX.

The compound of Formula XXXVI can be N-derivatised to give a compound of Formula XXXVII [wherein Rk can be hydrogen and Rt can be —C(=O)OC(CH$_3$)$_3$] with tert-butyl dicarbonate in an organic solvent, such as, for example, dichloromethane, carbon tetrachloride or chloroform, in the presence of a base, such as, for example, triethylamine, diisopropylethylamine, N-methylmorpholine or pyridine.

The compound of Formula XXXVI can be N-derivatised to give a compound of Formula XXXVII (when Rk and Rt together joins to form

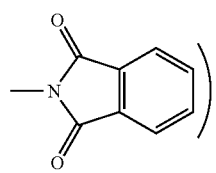

with phthalic anhydride in an organic solvent, such as, for example toluene, dioxane, diethyl ether or benzene, in the presence of a base, such as, for example, triethylamine, diisopropylethylamine, N-methylmorpholine or pyridine.

The oxidation of a compound of Formula XXXVII to give a compound of Formula XXXVIII can be carried out using an oxidizing agent, such as, for example, pyridinium chlorochromate, manganese dioxide, potassium permanganate or Jones reagent ($CrO_3/H_2SO_4$).

The methylenation of a compound of Formula XXXVIII to give a compound of Formula XXXIX can be carried out in an organic solvent, such as, for example, tetrahydrofuran, dimethylformamide, dioxane or diethylether, in the presence of Wittig salt, such as, for example, triphenylmethylphosphonium iodide or triphenylmethylphosphonium bromide.

Alternatively, the methylenation of a compound of Formula XXXVIII to give a compound of Formula XXXIX can be carried out using $Zn/CH_2Br_2/TiCl_4$ in an organic solvent, such as, for example tetrahydrofuran, dimethylformamide, dioxane or diethylether.

Particular compounds formed following the procedure shown in Scheme IX include:
4-(methylene-cyclohexyl)-carbamic acid tert-butyl ester, and
2-(4-methylene-cyclohexyl)-isoindole-1,3-dione.

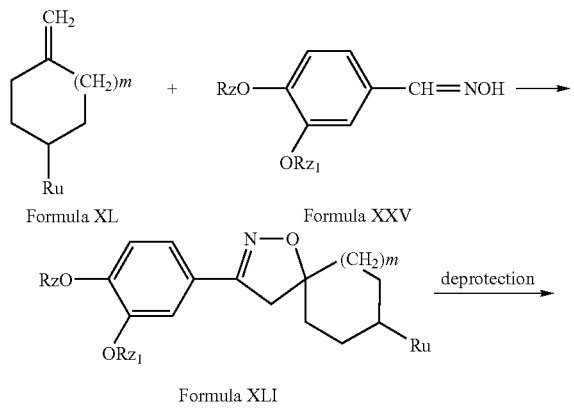

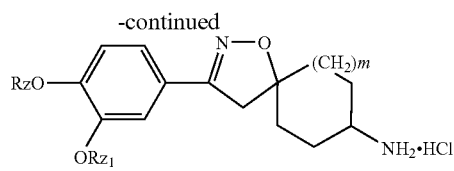

Formula XLII

[when Ru is —NRkRt (wherein Rk is hydrogen and Rt is —C(═O)OC(CH$_3$)$_3$]

The compound of Formula XLII can be prepared by following the reaction sequence as depicted in Scheme X. Thus, a compound of Formula XL (wherein m can be 0 or 1 and Ru can be —NRkRt or no atom) can be reacted with a compound of Formula XXV to give a compound of Formula XLI, which can be deprotected [wherein Ru can be —NRkRt, wherein Rk can be hydrogen and Rt can be —C(═O)OC(CH$_3$)$_3$] to give a compound of Formula XLII.

The reaction of a compound of Formula XL with a compound of Formula XXV to give a compound of Formula XLI can be carried out in an organic solvent, such as, for example, chloroform, dichloromethane, carbon tetrachloride or dichloroethane, in the presence of a base, such as, for example, pyridine, N-methylmorpholine, triethylamine or diisopropylethylamine.

The deprotection of a compound of Formula XLI to give a compound of Formula XLII [wherein Ru can be —NRkRt, wherein Rk can be hydrogen and Rt can be —C(═O)OC(CH$_3$)$_3$] can be carried out in an organic solvent, such as, for example, methanol in hydrochloric acid or ethanol in hydrochloric acid.

Particular compounds formed following the procedure shown in Scheme X include:
[3-(3-Cyclopentyloxy-4-methoxy-phenyl)-1-oxa-2-aza-spiro[4.5]dec-2-en-8-yl]-carbamic acid isopropyl ester (Compound No. 79), Hydrochloride salt of 3-(3-cyclopentyloxy-4-methoxy-phenyl)-1-oxa-2-aza-spiro[4.5]dec-2-en-8-ylamine (Compound No. 80), 2-[3-(3-Cyclopentyloxy-4-methoxy-phenyl)-1-oxa-2-aza-spiro[4.5]dec-2-en-8-yl]-isoindole-1,3-dione (Compound No. 81), 7-(3-Cyclopentyloxy-4-methoxy-phenyl)-5-oxa-6-aza-spiro[3.4]oct-6-ene (Compound No. 82), and 3-(3-Cyclopentyloxy-4-methoxy-phenyl)-1-oxa-2-aza-spiro[4.5]dec-2-ene (Compound No. 83).

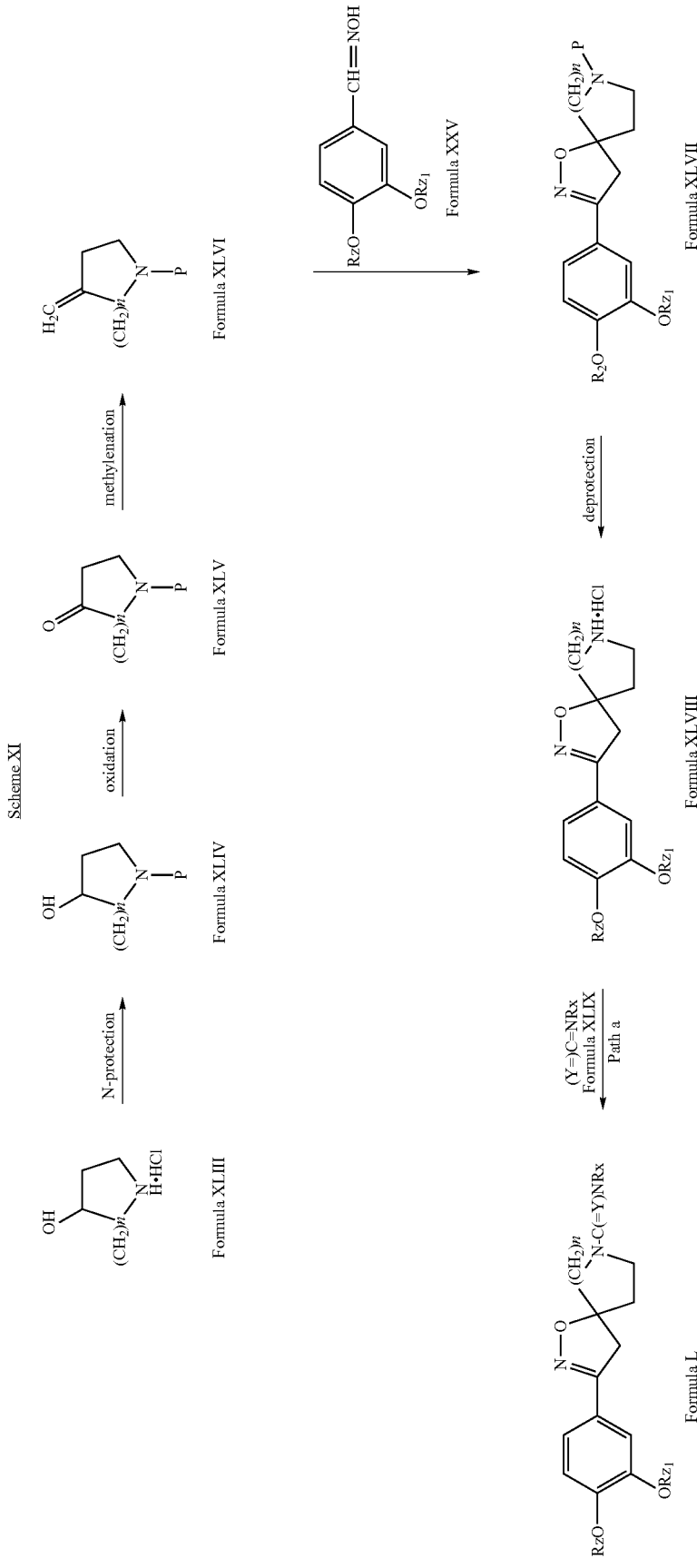

The compounds of Formula L can be prepared by following the reaction sequence as depicted in Scheme XI. Thus, a compound of Formula XLIII (wherein n can be 1, 2 or 3) can be N-protected to give a compound of Formula XLIV (wherein P can be —C(=O)OC($CH_3$)$_3$, —C(=O)OC($CH_3$)$_2$CHBr$_2$ or —C(=O)OC($CH_3$)$_2$CCl$_3$) to give a compound of Formula XLIV, which can be oxidized to give a compound of Formula XLV, which can undergo methylenation to give a compound of Formula XLVI, which can be reacted with a compound of Formula XXV to give a compound of Formula XLVII, which can be deprotected to give a compound of Formula XLVIII, which can be reacted with a compound of Formula XLIX (wherein Y can be oxygen or sulfur and $R_x$ can be the same as defined earlier) to give a compound of Formula L.

The N-protection of a compound of Formula XLIII to give a compound of Formula XLIV [wherein P can be —C(=O)OC($CH_3$)$_3$] can be carried out in an organic solvent, such as, for example, dichloromethane, dichloroethane form or carbon tetrachloride, in the presence of a base, such as, for example triethylamine, diisopropylethylamine, N-methylmorpholine or pyridine.

The N-protection of a compound of Formula XLIII to give a compound of Formula XLIV [when P can be —C(=O)OC($CH_3$)$_2$CHBr$_2$ or —C(=O)OC($CH_3$)$_2$CCl$_3$] can be carried out following the procedure, as described in Theodora W. Greene and Peter G. M. Wuts, "Protecting Groups In Organic Synthesis," 3$^{rd}$ edition, John Wiley and Sons, New York 1999.

The oxidation of a compound of Formula XLIV to give a compound of Formula XLV can be carried out using an oxidizing agent, such as, for example, pyridinium chlorochromate, manganese dioxide, potassium permanganate or Jones reagent ($CrO_3$/$H_2SO_4$).

The methylenation of a compound of Formula XLV to give a compound of Formula XLVI can be carried out in an organic solvent, such as, for example, tetrahydrofuran, dimethylformamide, dioxane or diethylether, in the presence of a Wittig salt for example, triphenylmethyl-phosphonium iodide or triphenylmethylphosphonium bromide.

Alternatively, the methylenation of a compound of Formula XLV to give a compound of Formula XLVI can be carried out using Zn/$CH_2Br_2$/$TiCl_4$ in an organic solvent, such as, for example, tetrahydrofuran, dimethylformamide, dioxane or diethylether.

The reaction of a compound of Formula XLVI with a compound of Formula XXV to give a compound of Formula XLVII can be carried out in an organic solvent, such as, for example, dichloromethane, chloroform, carbon tetrachloride or dichloromethane, in the presence of a base, such as, for example, pyridine, N-methylmorpholine, diisopropylethylamine or triethylamine.

The deprotection of a compound of Formula XLVII (wherein P can be —C(=O)OC($CH_3$)$_3$) to give a compound of Formula XLVIII can be carried out in an organic solvent, such as, for example, methanol, ethanol, propanol or isopropylalcohol, in the presence of an alcoholic acid solution, such as, for example, ethanolic hydrochloric acid or methanolic hydrochloric acid.

The deprotection of a compound of Formula XLVII (wherein P can be —C(=O)OC($CH_3$)$_2$CHBr$_2$) can be carried out in an organic solvent, such as, for example, ethanol, methanol, propanol or isopropylalcohol, or by hydrobromide in acetic acid.

The deprotection of a compound of Formula XLVII (wherein P can be —C(=O)OC($CH_3$)$_2$CCl$_3$) can be carried out by a supernucleophile, such as, for example, lithium cobalt (I) phthalocyanine, zinc and acetic acid or cobalt phthalocyanine.

The compound of Formula XLVIII can be reacted with a compound of Formula XLIX in an organic solvent, such as, for example, dichloroethane, dichloromethane, chloroform or carbon tetrachloride, to give a compound of Formula L.

Particular compounds formed following the procedure shown in Scheme XI include:

3-(3-Cyclopentyloxy-4-methoxy-phenyl)-1-oxa-2,8-diaza-spiro[4.5]dec-2-ene-8-carboxylic acid isopropyl ester (Compound No. 74), Hydrochloride salt of 3-(3-cyclopentyloxy-4-methoxy-phenyl)-1-oxa-2,8-diaza-spiro[4.5]dec-2-ene (Compound No. 75), 4-Chloro-N-[3-(3-cyclopentyloxy-4-methoxy-phenyl)-1-oxa-2,8-diaza-spiro[4.5]dec-2-ene-8-carbonyl]-benzene sulfonamide (Compound No. 76), 3-(3-Cyclopentyloxy-4-methoxy-phenyl)-1-oxa-2,8-diaza-spiro[4.5]dec-2-ene-8-carboxylic acid-(2,6-difluoro-phenyl)-amide (Compound No. 77), 3-(3-Cyclopentyloxy-4-methoxy-phenyl)-1-oxa-2,8-diaza-spiro[4.5]dec-2-ene-8-carboxylic acid-(2,4-dichloro-phenyl)-amide (Compound No. 78), 3-(3-Cyclopentyloxy-4-methoxy-phenyl)-1-oxa-2,7-diaza-spiro[4.4]non-2-ene-7-carboxylic acid tert-butyl ester (Compound No. 84), and Hydrochloride salt of 3-(3-cyclopentyloxy-4-methoxy-phenyl)-1-oxa-2,7-diaza-spiro[4.4]non-2-ene (Compound No. 85).

In the above schemes, specific bases, condensing agents, hydrolyzing agents, solvents, and the like, known to those skilled in the art, may be used. Similarly, the reaction temperature and duration of the reaction may be adjusted according to the desired needs.

The Examples set forth below demonstrate the general synthetic procedure for the preparation of representative compounds. The examples are provided to illustrate particular aspects of the disclosure and do not limit the scope of the claims.

EXAMPLES

General Procedure

Synthesis of
3-Cyclopentyloxy-4-methoxy-benzaldehyde
(Formula II)

The title compound was prepared according to the method described in J. Med. Chem., 1994, 37, 1696-1703.

Synthesis of
3-Cyclopentyloxy-4-methoxy-benzaldehyde Oxime
(Formula III)

Hydroxylamine hydrochloride (0.473 g, 6.8181 mmol) and sodium acetate (0.56 g, 6.8181 mmol) was added to a stirred solution of compound of Formula II (0.5 g, 2.2727 mmol) in ethanol (8 mL). The reaction mixture was stirred at room temperature for 50 minutes. Ethanol was evaporated under reduced pressure, which was diluted with water (20 mL) and the organic compound was extracted with ethyl acetate (2×15 mL). The ethyl acetate layer was dried over anhydrous sodium sulphate, filtered and concentrated under reduced pressure to afford compound of Formula III. Analysis by $^1$H NMR spectroscopy gave the following peaks ($CDCl_3$): 9.84

(s, 1H), 8.07 (s, 1H), 6.84-7.24 (m, 3H), 4.79-4.83 (m, 1H), 3.87 (s, 3H), 1.62-2.18 (m, 8H).

Synthesis of 2-(3-Cyclopentyloxy-4-methoxy-phenyl)-4-methyl-4,5-dihydro-isoxazol-5-carboxylic Acid Methyl Ester (Formula V)

Methyl methacrylate (42.5 g, 0.42 mol, 10 eq) was added to the solution of compound of Formula III (10 g, 0.042 mol, 1 eq) in tetrahydrofuran (70 mL), and the resulting reaction mixture was stirred at room temperature. Sodium hypochlorite (100 mL) was added slowly to the mixture thus obtained over the period of 20 minutes and the reaction mixture was allowed to stir at room temperature overnight. A second lot of sodium hypochlorite (100 mL) was again added to it and stirred for 2 hours at room temperature. Tetrahydrofuran was evaporated off and the organic compound was extracted with ethyl acetate twice. The organic layer was concentrated to yield the title compound with a yield of 14 g. The melting point of the compound was 107-108° C. Analysis by $^1$H NMR spectroscopy gave the following peaks (CDCl$_3$): δ 7.38-7.39 (d, 1H), 7.02-7.06 (dd, 1H), 6.85-6.88 (d, 1H), 4.82-4.85 (m, 1H), 3.80-3.83 (s, 6H, 2×OCH$_3$), 3.63 (s, 1H), 3.2-3.25 (d, 1H), 1.92-2.07 (m, 8H), 1.79 (S, 3H). Mass spectroscopy gave the following peaks (m/z): 333 (M)$^+$, 334.3 (M+1)$^+$.

Synthesis of 2-(3-Cyclopentyloxy-4-methoxy-phenyl)-4-methyl-4,5-dihydro-isoxazol-5-carboxylic Acid (Formula VI)

The compound of Formula V (0.07, 0.2102 mmole, 1 eq.) was dissolved in tetrahydrofuran (1.5 mL) and lithium hydroxide in water solution (0.48 mL of 0.5 M aqueous solution, 0.24 mmoles, 1.2 eq) was added. The mixture was stirred for 1 hour at room temperature and an additional amount of lithium hydroxide in water solution (0.19 mL, 0.5 M, 0.004 g) was added. The mixture was stirred for 2 hour 35 minutes. Solvent was removed under reduced pressure and the residue thus obtained was diluted with water and acidified with drop of concentrated hydrochloric acid. The organic compound was extracted with ethyl acetate, washed with brine, dried over anhydrous sodium sulphate and finally concentrated under reduced pressure to afford title organic compound with a yield of 0.066 g, and a melting point of 142-144° C. Analysis by $^1$H NMR spectroscopy gave the following peaks (C$_3$D$_6$O): 7.31-7.32 (d, 1H), 7.15-7.18 (dd, 1H), 6.69-7.00 (d, 1H) 4.85-4.87 (m, 1H), 3.83-6.89 (s, 3H, OCH$_3$), 3.60 (s, 1H), 3.30-3.31 (d, 1H), 1.96-2.06 (m, 8H), 1.64 (s, 3H, 1×CH$_3$). Mass spectroscopy gave the following peaks (m/z): 319 (M)$^+$, 320.2 (M+1)$^+$.

Synthesis of 3-(3-Cyclopentyloxy-4-methoxy-phenyl)-5-ethoxycarbonylmethyl-4,5-dihydro-isoxazol-5-yl]-acetic Acid Ethyl Ester (Formula XIII)

The compound of Formula III (3 g, 0.0127 moles, 1 eq) was dissolved in tetrahydrofuran and 2-methylene succinic acid diethyl ester (4.74 g, 0.0255M) was added. The resulting reaction mixture was heated to 60° C. with constant stirring. Solution of sodium hypochlorite (24.0 mL) was added slowly to the mixture at 60-65° C. and stirred for 20 hours. A second amount of sodium hypochlorite (2 mL) was added to the mixture and stirred for five hours. Tetrahydrofuran was evaporated off from the reaction mixture and to the residue thus obtained was added ethyl acetate (30 mL), washed with water (40 mL), dried over sodium sulphate and concentrated under reduced pressure to afford the crude organic compound. The crude compound was purified by column chromatography using ethyl acetate and hexane solvent mixture as an eluent, with a yield of 2.52 gm, and a melting point of 85-86° C. Analysis by $^1$H NMR spectroscopy gave the following peaks (CDCl$_3$): 7.35 (s, 1H), 7.03-7.07 (d, 1H), 6.83-6.86 (d, 1H), 4.80-4.82 (m, 1H), 4.18-4.31 (m, 4H), 3.98-4.04 (d, 1H), 3.88 (s, 3H), 3.43-3.49 (d, 1H), 3.22-3.28 (d, 1H), 2.92-2.98 (d, 1H), 1.80-1.99 (m, 8H), 1.11-1.33 (m, 6H). Mass spectroscopy gave the following peaks (m/z): 419(M)$^+$, 420.6 (M+1)$^+$.

Synthesis of 5-Carboxymethyl-3-(3-cyclopentyloxy-4-methoxyphenyl)-4,5-dihydro-isoxazol-5-carboxylic Acid (Formula XIV)

The title compound was prepared following the procedure as described for the synthesis of compound of Formula VI, by using compound of Formula XIII in place of compound of Formula V. Analysis by $^1$H NMR spectroscopy gave the following peaks (DMSO-d$_6$): 6.98-7.21 (m, 3H), 4.83 (s, 1H), 3.78 (S, 3H), 3.49-3.55 (d, 1H), 2.89 (s, 2H), 2.50-2.73 (d, 1H), 1.70-1.99 (m, 8H). Mass spectroscopy gave the following peaks (m/z): 363 (M)$^+$, 364.1 (M+1)$^+$.

Example 1

1-1'-[3-(3-Cyclopentyloxy-4-methoxy-phenyl)-5-methyl-4,5-dihydro-isoxazole-5-carbonyl]-4-phenyl-piperidine-4-yl}-ethanone (Compound No. 15)

Hydroxybenzotriazole (0.0296 g, 0.2194 mmole) and N-methyl morpholine (48 μL, 0.4388 mmole) were added to a cooled (0-5° C.) solution of compound of Formula VI (0.07 gm, 0.2194 mmole) and 1-(4-phenyl-piperidin-4-yl)-ethanone (0.0789 g, 0.3291 mmole) in 0.6 mL dry dimethyl formamide. The resulting solution was allowed to stir at 0-5° C. for 1 hour. Thereafter, dicyclohexylcarbodiimide (0.0903 g, 0.4388 mmol) was added and the resulting mixture was allowed to stir at the same temperature for 30 minutes, followed by stirring at room temperature for 22.5 hours. The reaction was quenched by adding water (10 mL) to the reaction mixture. The resulting solution was extracted with ethyl acetate (2×15 mL). The white solid, which separated on keeping the ethyl acetate layer at room temperature, was filtered off. The filtrate was dried over anhydrous sodium sulphate and was concentrated under reduced pressure to afford the title organic compound with a yield of 0.1916 g. Analysis by $^1$H NMR spectroscopy showed the following peaks (CDCl$_3$): δ 6.82-7.26 (m, 8H), 4.79 (s, 1H), 4.06-4.08 (d, 1H), 3.86 (s, 3H), 3.06-3.12 (d, 1H), 1.158-1.836 (m, 22H).

Particular analogs of 1-{1-[3-(3-Cyclopentyloxy-4-methoxy-phenyl)-5-methyl-4,5-dihydro-isoxazole-5-carbonyl]-4-phenyl-piperidine-4-yl}ethanone (Compound No. 15), which are described below, can be prepared by substitution of the compound of Formula VI with corresponding cyclic amines.

1-[3-(3-Cyclopentyloxy-4-methoxy-phenyl)-5-methyl-4,5-dihydro-isoxazole-carbonyl]-pyrrolidin-2-carboxylic Acid (Compound No. 11)

Analysis by $^1$H NMR spectroscopy showed the following peaks (CDCl$_3$): δ 7.32-7.33 (d, 1H), 6.99-7.07 (dd, 1H), 6.83-6.83 (d, 1H), 4.80 (s, 1H), 3.87-4.56 (m, 5H), 3.18-3.31 (m, 1H), 1.25-2.23 (m, 14H), 1.25 (s, 3H). Mass spectroscopy showed the following peaks (m/z): 416 (M)$^+$, 417 (M+1)$^+$.

[3-(3-Cyclopentyloxy-4-methoxy-phenyl)-5-methyl-4,5-dihydro-isoxazol-5-yl]-piperidin-1-yl-methanone (Compound No. 9)

Analysis by $^1$H NMR spectroscopy showed the following peaks (CDCl$_3$): δ 7.3 (s, 1H), 7.07-7.09 (d, 1H), 6.83-6.86 (d, 1H), 4.80 (s, 1H), 3.86-3.93 (m, 7H), 3.07-3.35 (m, 2H), 1.52-2.01 (m, 17H). Mass spectroscopy showed the following peaks (m/z): 386 (M)$^+$, 387.6 (M+1)$^+$.

[3-(3-Cyclopentyloxy-4-methoxy-phenyl)-5-methyl-4,5-dihydro-isoxazol-5-yl]-(4-methyl-piperazin-1-yl)-methanone (Compound No. 16)

Analysis by $^1$H NMR spectroscopy showed the following peaks: 7.26-7.32 (d, 1H), 7.06-7.09 (d, 1H), 6.83-6.86 (d, 1H), 4.78-4.81 (m, 1H), 4.32-4.38 (d, 1H), 3.87 (s, 3H), 3.08-3.14 (d, 1H), 2.35-2.53 (m, 7H), 1.58-2.04 (m, 15H). Mass spectroscopy showed the following peaks (m/z): 401 (M)$^+$, 402.5 (M+1)$^+$.

[4-(4-Chloro-phenyl)-4-hydroxy-piperidin-1-yl]-[3-(3-cyclopentyloxy-4-methoxy-phenyl)-5-methyl-4,5-dihydroisoxazol-5-yl]-methanone (Compound No. 18)

Analysis by $^1$H NMR spectroscopy showed the following peaks (CDCl$_3$): 6.84-7.43 (m, 7H), 4.80 (s, 1H), 4.40-4.46 (d, 1H), 3.86 (s, 3H), 3.09-3.11 (1H), 1.71-2.34 (m, 19H). Mass spectroscopy showed the following peaks (m/z): 512.5 (M)$^+$, 513.2 (M+1)$^+$.

1-[3-(3-Cyclopentyloxy-4-methoxy-phenyl)-5-methyl-4,5-dihydro-isoxazol-5-carbonyl]-pyrrolidine-2-carboxylic Acid Methyl Ester (Compound No. 12)

Analysis by $^1$H NMR spectroscopy showed the following peaks (CDCl$_3$): 7.33-7.37 (d, 1H), 7.07-7.09 (d, 1H), 6.85-6.83 (d, 1H), 4.82 (s, 1H), 4.10-4.23 (d, 1H), 3.71-3.91 (m, 6H), 3.09-3.22 (d, 1H), 1.67-2.19 (m, 18H). Mass spectroscopy showed the following peaks (m/z): 430 (M)$^+$, 431.2 (M+1)$^+$.

[3-Hydroxymethyl-piperidin-1-yl]-[3-(3-cyclopentyloxy-4-methoxy-phenyl)-5-methyl-4,5-dihydro-isoxazol-5-yl]-methanone (Compound No. 22)

Analysis by $^1$H NMR spectroscopy showed the following peaks (CDCl$_3$): 7.32 (s, 1H), 7.07-7.10 (d, 1H), 6.83-6.86 (d, 1H), 4.80 (s, 1H), 3.82 (s, 3H), 3.41-3.52 (m, 2H), 2.84 (s, 2H), 1.47-2.08 (m, 20H). Mass spectroscopy showed the following peaks (m/z): 416 (M)$^+$, 417.3 (M+1)$^+$.

[3-(3-Cyclopentyloxy-4-methoxy-phenyl)-5-methyl-4,5-dihydro-isoxazol-5-yl]-pyrrolidin-1-yl-methanone (Compound No. 13)

Analysis by $^1$H NMR spectroscopy showed the following peaks (CDCl$_3$): 7.32 (s, 1H), 7.05-7.08 (d, 1H), 6.83-6.85 (d, 1H), 4.80-4.81 (m, 1H), 4.17-4.23 (d, 1H), 3.79 (s, 3H), 3.11-3.16 (d, 1H), 1.63-2.01 (m, 19H). Mass spectroscopy showed the following peaks (m/z): 372 (M)$^+$, 373.1. (M+1)$^+$.

[3-(3-Cyclopentyloxy-4-methoxy-phenyl)-5-methyl-4,5-dihydro-isoxazol-5-yl]-(4-isobutyl-1-piperazin-1-yl)-methanone (Compound No 21)

Analysis by $^1$H NMR spectroscopy showed the following peaks (CDCl$_3$): 7.28 (s, 1H), 7.01-7.04 (d, 1H), 6.78-6.81 (d, 1H), 4.75 (s, 1H), 4.27-4.32 (d, 1H), 3.02-3.08 (d, 1H), 3.82 (s, 3H), 1.56-2.03 (m, 18H), 1.20 (s, 3H), 0.84-0.86 (m, 7H). Mass spectroscopy showed the following peaks (m/z): 443 (M)$^+$, 444 (M+1)$^+$.

4-[3-(3-Cyclopentyloxy-4-methoxy-phenyl)-5-methyl-4,5-dihydro-isoxazole-5-carbonyl]-piperazine-1-carboxylic Acid Tert-butyl Ester (Compound No. 10)

Analysis by $^1$H NMR spectroscopy showed the following peaks (CDCl$_3$): 7.26-7.32 (d, 1H), 7.07-7.09 (d, 1H), 6.84-6.86 (d, 1H), 4.79-4.81 (m, 1H), 4.32-4.38 (d, 1H), 3.09-3.15 (d, 1H), 3.78 (s, 3H, OCH$_3$), 1.68-1.99 (m, 16H), 1.43 (s, 9H, 3×CH$_3$). Mass spectroscopy showed the following peaks (m/z): 487 (M)$^+$, 488.5 (M+1)$^+$.

1-[3-(3-Cyclopentyloxy-4-methoxy-phenyl)-5-methyl-4,5-dihydro-isoxazol-5-carbonyl]-pyrrolidin-3-carboxylic acid diethyl amide (Compound No. 30)

Analysis by $^1$H NMR spectroscopy showed the following peaks (CDCl$_3$): δ 7.320 (d, 1H) 7.047-7.078 (d, 1H), 6.828-6.849 (d, 1H) 4.816 (s, 1H) 4.80 (m, 1H), 4.25-4.31 (d, 1H), 3.90-3.96 (d, 1H), 3.86 (s, 3H), 3.5-3.6 (2H), 3.37-3.43 (m, 2H), 3.1-3.23 (m, 2H), 1.08-1.97 (m, 21H). Mass spectroscopy showed the following peaks (m/z): 471(M)$^+$, 472.700 (M+1)$^+$.

[3-(Cyclopentyloxy-4-methoxy-phenyl)-5-methyl-4,5-dihydro-isoxazole-5-carboxyl]-pyrrolidine-3-carboxylic Acid Amide (Compound No. 33)

Analysis by $^1$H NMR spectroscopy showed the following peaks (CDCl$_3$): 7.32 (s, 1H), 7.05-7.08 (d, 1H), 6.83-6.86 (d, 1H), 4.80-4.82 (s, 1H), 4.06-4.125 (d, 1H), 3.87-3.89 (s,3H), 3.35-3.40 (m, 2H), 3.35-3.40 (m, 1H), 2.84 (s, 3H), 1.6-2.0 (M, 13H). Mass spectroscopy showed the following peaks (m/z): 415 (m)+416.300 (M+1)$^+$.

[4-(4-Bromophenyl)-4-hydroxy-piperidin-1-yl]-[3-(3-cyclopentyloxy-4-methoxy-phenyl)-5-methyl-4,5-dihydro-isoxazol-5-yl]-methanone (Compound No 26)

Analysis by $^1$H NMR spectroscopy showed the following peaks (CDCl$_3$): δ 7.342-7.49 (m, 5H), 7.09-7.11 (d, 1H), 6.84-6.87 (d, 1H), 4.81 (s, 1H), 4.40-4.46 (d, 1H), 3.88 (s, 1H), 3.09-3.21 (m, 1H), 1.68-2.17 (m, 19H). Mass spectroscopy showed the following peaks: 557 (M)$^+$, 558 (M+1)$^+$.

1-[13-(3-Cyclopentyloxy-4-methoxy-phenyl)-5-methyl-4,5-dihydro-isoxazole-5-carbonyl]-piperidin-4-one (Compound No. 25)

Analysis by $^1$H NMR spectroscopy showed the following peaks (CDCl$_3$): 7.32-7.33 (d, 1H), 7.07-7.10 (d, 1H), 6.84-6.87 (d, 1H), 9.81-4.83 (m, 1H), 4.42-4.44 (d, 1H), 3.88 (s, 3H) 3.13-3.19 (d, 1H), 2.49-2.51 (m, 4H) 1.57-2.04 (m, 15H). Mass spectroscopy showed the following peaks (m/z): 400 (M)$^+$, 401.2 (M+1)$^+$.

(5-Benzyl-2,5-diaza-bicyclo[2.2.1 hept-2-yl-[3-(3-cyclopentyloxy-4-methoxy-phenyl)-5-methyl-4,5-dihydro-isoxazol-5-yl]-methanone (Compound No.

27)

Analysis by ¹H NMR spectroscopy showed the following peaks (CDCl₃): δ 7.303-7.35 (m, 6H) 7.06-7.08 (d, 1H) 6.83-6.88 (m, 1H), 4.8 (s, 1H), 3.87 (s, 3H, OCH₃), 3.70-3.78 (m, 3H), 3.33-3.5 (m, 2H), 2.8 (s, 2H), 1.6-2.04 (m, 16H). Mass spectroscopy showed the following peaks (m/z): 489(M)⁺, 490.500 (M+1)⁺.

(4-Benzyl-piperazin-1-yl)-[3-(3-cyclopentyloxy-4-methoxy-phenyl)-5-methyl-4,5-dihydro-isoxazol-5-yl)-methanone (Compound No. 28)

Analysis by ¹H NMR spectroscopy showed the following peaks (CDCl₃): δ 7.26-7.32 (m, 6H) 7.06-7.08 (d, 1H), 6.83-6.86 (d, 1H) 4.8 (s, 1H) 4.31-3.37 (d, 1H) 3.87 (s, 3H), 3.36-3.4 (m, 2H), 3.13 (d, 1H) 2.35-2.55 (m, 8H), 1.61-2.04 (m, 11H). Mass spectroscopy showed the following peaks (m/z): 477(M)⁺, 478.500 (M+1)⁺.

1-[3-(3-Cyclopentyloxy-4-methoxy-phenyl)-5-methyl-4,5-dihydro-isoxazole-5-carbonyl]-pyrrolidin-3-carboxylic Acid Methyl Amide (Compound No 29)

Analysis by ¹H NMR spectroscopy showed the following peaks (CDCl₃): δ 7.33 (d, 1H), 7.05-7.07 (d, 1H), 6.84-6.87 (d, 1H), 4.80-4.81 (d, 1H); 4.18-4.23 (d, 1H), 3.87 (s, 3H), 3.10-3.22 (m, 1H), 2.72-2.82 (m, 3H), 1.62-2.10 (m, 18H). Mass spectroscopy showed the following peaks (m/z): 429 (M)⁺, 430.500 (M+1)⁺.

1-[3-(3-Cyclopentyloxy-4-methoxy-phenyl)-5-methyl-4,5-dihydroisoxazole-5-carbonyl]-piperidine-2-carboxylic Acid Methyl Ester (Compound No. 32)

Analysis by ¹H NMR spectroscopy showed the following peaks (CDCl₃): δ 7.33-7.35 (d, 1H), 7.07-7.10 (d, 1H), 6.83-6.86 (m, 1H), 4.79-9.8 (d, 1H), 4.36-4.42 (d, 1H), 3.8 (s, 3H), 3.71-3.79 (m, 3H), 3.0-3.16 (d, 1H), 1.23-2.04 (m, 20H). Mass spectroscopy showed the following peaks (m/z): 444 (M)⁺, 445.5 (M+1)⁺.

(4-Benzyl-piperidin-1-yl)-[3-(3-cyclopentyloxy-4-methoxy-phenyl)-5-methyl-4,5-dihydro-isoxazol-5-yl]-methanone (Compound No. 24)

Analysis by ¹H NMR spectroscopy showed the following peaks (CDCl₃): δ 6.8-7.34 (m, 8H), 4.8 (d, 1H), 4.54-4.48 (d, 1H), 9.36-4.41 (d, 1H), 3.87 (s, 3H), 3.06-3.15 (m, 2H), 2.53-2.63 (m, 4H), 1.64-2.04 (m, 16H). Mass spectroscopy showed the following peaks (m/z): 476 (M+), 477.3 (M+1)⁺.

[3-(3-Cyclopentyloxy-4-methoxy-phenyl)-5-methyl-4,5-dihydro-isoxazol-5-yl]-(4-hydroxy-piperidin-1-yl)-methanone (Compound No 23)

Analysis by ¹H NMR spectroscopy showed the following peaks (CDCl₃): δ 7.33 (s, 1H), 6.86-7.13 (d, 2H), 4.8 (s, 1H), 4.37 (d, 1H) 3.87 (s, 3H), 3.1 (d, 1H), 1.85-2.01 (m, 8H) 1.25-1.56 (m, 12H). Mass spectroscopy showed the following peaks (m/z): 402.4 (M)⁺, 403.4 (M+1)⁺.

{4-[3-(3-Cyclopentyloxy-4-methoxy-phenyl)-5-methyl-4,5-dihydro-isoxazole-5-carbonyl]-[1,4]diazepan-1-yl}-[3-(3-cyclopentyloxy-4-methoxy-phenyl)-5-methyl-4,5-dihydro-isoxazol-5-yl]-methanone (Compound No. 19)

Analysis by mass spectroscopy showed the following peaks (m/z): 702 (M+), 703.4 (M+1)⁺.

[3-(3-Cyclopentyloxy-4-methoxy-phenyl)-5-methyl-4,5-dihydro-isoxazol-5-yl-(2-methoxy methyl-pyrrolidin-1-yl)-methanone (Compound No. 37)

Analysis by ¹H NMR spectroscopy showed the following peaks (CDCl₃): δ 7.33 (s, 1H), 7.05-7.08 (d, 1H), 6.83-6.86 (d, 1H), 4.80 (s, 1H), 4.11-4.20 (d, 2H), 3.87 (s, 3H), 3.55-3.84 (m, 1H), 3.35-3.40 (d, 1H), 3.18 (s, 3H), 3.06-3.12 (d, 1H), 1.54-2.00 (m, 17H). Mass spectroscopy showed the following peaks (m/z): (416) (M)⁺, 417.50 (M+1)⁺.

[3-(3-Cyclopentyloxy-4-methoxy-phenyl)-5-methyl-4,5-dihydro-isoxazol-5-yl]-(3-hydroxymethyl-pyrrolidin-1-yl)-methanone (Compound No. 31)

Analysis by ¹H NMR spectroscopy showed the following peaks (CDCl₃): δ 7.307 (d, 1H), 7.036-7.064 (d, 1H), 6.820-6.848 (d, 1H), 4.783 (s, 1H), 4.14-4.28 (m, 3H), 3.85 (s, 3H), 3.6-3.66 (m, 3H), 3.13-3.19 (m, 1H), 1.54-2.02 (m, 15H). Mass spectroscopy showed the following peaks (m/z): 402 (M)⁺, 403.400 (M+1)⁺.

Example 2

[3-(3-Cyclopentyloxy-4-methoxy-phenyl]-5-methyl-4,5-dihydro-isoxazol-5-yl]-piperazin-1-yl-methanone (Compound No. 17)

Trifluoroacetic acid (0.13 mL, 1.6825 mmole) was added to a solution of Compound No. 1 (0.1639 g, 0.3365 mmole) in dichloromethane (3 mL) and the reaction mixture was stirred at room temperature for 4.5 hour. The reaction was quenched by adding water (10 mL) and the reaction mixture was made basic by adding sodium bicarbonate solution. The resulting mixture was extracted with ethyl acetate (2×10 mL). Ethyl acetate layer was washed with water, dried over anhydrous sodium sulphate, filtered and finally concentrated under reduced pressure to afford a semi-solid residue, which on treatment with hexane, afforded the title organic compound.

Analysis by ¹H NMR spectroscopy showed the following peaks (CDCl₃): δ 7.33 (d, 1H), 7.07-7.09 (d, 1H), 6.84-6.86 (d, 1H), 4.80 (s, 1H), 4.33-4.39 (d, 1H), 3.88 (s, 3H), 3.09-3.14 (d, 1H), 2.8-2.9 (m, 4H), 1.62-2.05 (m, 15H). Mass spectroscopy showed the following peaks (m/z): 387 (M)⁺, 388.1 (M+1)⁺.

Example 3

3-(3-Cyclopentyloxy-4-methoxy-phenyl)-5-methyl-4,5-dihydro-isoxazol-5-yl]-(4-cyclopropylmethyl-piperazin-1-yl)-methanone (Compound No. 20)

Anhydrous potassium carbonate (0.1368 g, 0.992 mmol) was added to a stirred solution of Compound No. 17 (0.048 g, 0.1240 mmol) and cyclopropyl methyl chloride (25 μL, 0.2728 mmol) in dry acetone (4 mL). The resulting mixture was refluxed in an oil bath and the temperature was maintained at 50-55° C. for 24 hour. The reaction was quenched by adding water (20 mL). The resulting mixture was extracted with ethyl acetate (2×10 mL). The ethyl acetate layer was washed with water and dried over anhydrous potassium carbonate. The organic layer was concentrated under reduced pressure to afford the title organic compound.

Analysis by $^1$H NMR spectroscopy showed the following peaks (CDCl$_3$): δ 7.33 (s, 1H), 7.07-7.09 (d, 1H), 6.83-6.86 (d, 1H), 3.8 (s, 3H), 3.08-3.14 (d, 1H), 1.33-1.85 (m, 21H), 0.07-0.56 (m, 5H).

Example 4

[1-4]-Bipiperidinyl-1-yl-[3-(3-cyclopentyloxy-4-methoxy-phenyl)-5-methyl-4-,5-dihydro-isoxazol-5-yl]-methanone (Compound No. 14)

Thionyl Chloride (0.186 g, 1.57 mmoles, 10 eq) was added to a solution of compound of Formula VI (0.05 g) in acetonitrile (1.5 mL) and the solution refluxed at 70-72° C. for 3 hours. The solvent was removed under reduced pressure and excess of thionyl chloride was azeotropically distilled off using toluene. The resulting product was taken in dichloromethane (2 mL) and to this was added 4-piperidino-piperazine (0.0526 g) and triethyl amine (0.13 mL). The reaction mixture was stirred for 19 hours at room temperature. The resulting reaction mixture was diluted with water and extracted with dichloromethane. The organic layer was washed with brine, dried over anhydrous sodium sulphate and concentrated. The crude organic compound was obtained and purified by column chromatography using methanol:ethyl acetate [1:10] solvent system as eluent. Yield=0.038 gm.

Analysis by $^1$H NMR spectroscopy showed the following peaks: 7.32-7.35 (d, 1H), 7.07-7.10 (d, 1H), 6.84-6.87 (d, 1H), 4.8 (s, 1H), 4.7 (m, 2H), 4.35-4.40 (m, 2H), 3.88 (s, 3H), 3.07-3.13 (m, 0.1H), 1.5-2.07 (m, 27H). Mass spectroscopy showed the following peaks (m/z): 469 (M)$^+$, 470.1 (M+1)$^+$.

Example 5

[3-(3-Cyclopentyloxy-4-methoxy-phenyl)-5-(pyrrolidine-1-carbonyl)-4,5-dihydro-isoxazol-5-yl]-pyrrolidin-1-yl-methanone (Compound No. 3)

The compound of Formula XIV (70 mg, 0.193 mmoles, 1 eq.) was taken in dimethyl formamide (0.7 mL) followed by the addition of pyrrolidine (0.035 mL, 0.424 mmoles, 2.2 eq). The reaction mixture was cooled to 0° C. and to this was added hydroxy benzotriazole (52 mg, 0.385 mmole, 2 eq) and N-methyl morpholine (0.84 mL, 0.77 mmoles, 4 eq) and stirred for 1 hour at 0° C. To this was added 1-(3-dimethylaminopropyl)-3-ethyl carbodiimide hydrochloride (EDCHCl) (81.33 mg, 0.424 mmoles, 22 eq) at 0° C. with constant stirring. The reaction was allowed to warm to room temperature followed by stirring for 24 hours. The reaction mixture was diluted with water (10 mL) and the organic compound was extracted with ethyl acetate. The organic layer was washed with brine and dried over anhydrous sodium sulphate and concentrated under reduced pressure. The crude compound thus obtained was purified by column chromatography.

Analysis by H$^1$ NMR spectroscopy showed the following peaks (CDCl$_3$) δ: 7.323-7.327 (d, 1H, Ar), 7.07-7.10 (dd, 1H), 6.83-6.86 (d, 1H, Ar), 4.79-4.81 (m, 1H), 3.84-3.98 (m, 5H, OCH$_3$, CH$_2$), 3.43-3.55 (m, 8H), 2.9-3.04 (d, 1H), 2.84-2.89 (d, 1H), 1.77-1.97 (m, 16H).

Mass spectroscopy showed the following peaks (m/z): 469 (M)$^+$, 470.1 (M+1)$^+$.

Particular analogs of [3-(3-cyclopentyloxy-4-methoxy-phenyl)-5-(pyroline-1-carbonyl)-4,5-dihydro-isoxazol-5-yl]-pyrrolidin-1-yl-methanone (Compound No. 3), which are described below, can be prepared by reaction of a compound of Formula VI with corresponding cyclic amines.

[3-(3-Cyclopentyloxy-4-methoxy-phenyl)-5-(piperidine-1-carbonyl)-4,5-dihydro-isoxazol-5-yl]-piperidin-1-yl-methanone (Compound No. 4)

Analysis by $^1$H NMR spectroscopy showed the following peaks (CDCl$_3$): δ 7.325 (d, 1H), 7.09-7.11 (d, 1H, Ar), 6.83-6.85 (d, 1H, Ar), 4.79-4.816 (m, 1H) 3.96-4.05 (m, 2H), 3.87 (s, 3H, —OCH$_3$), 3.44-3.60 (m, 8H), 2.99 (s, 2H), 1.49-2.01 (m, 20H). Mass spectroscopy showed the following peaks (m/z): 497 (M)$^+$, 498.2 (M+1)$^+$.

[3-(3-Cyclopentyloxy-4-methoxy phenyl)-5-(pyrrolidin-2-carboxylic Acid Methyl Ester-1-carbonyl)-4,5-dihydro-isoxazol-5-yl)-[{pyrrolidine-2-carboxylic Acid Methyl Ester-5-yl]-ethanone (Compound No. 5)

Analysis by $^1$H NMR spectroscopy showed the following peaks (CDCl$_3$): δ 7.26-7.32 (m, 1H), 7.02-7.11 (m, 1H), 6.8-6.86 (m, 1H), 4.79 (m, 1H), 4.56-4.58 (m, 2H), 3.8-8.6 (s, 3H, —OCH$_3$), 3.5-3.78 (m, 8H), 2.84-3.59 (m, 6H), 1.83-2.1 (m, 16H). Mass spectroscopy showed the following peaks (m/z): 585 (M+), 586.2 (M+1)$^+$.

[5-[4-(4-Chlorophenyl)-4-hydroxy-piperidine-1-carbonyl]-3-(3-cyclopentyloxy-4-methoxy-phenyl)-4,5-dihydro-isoxazol-5-yl]-[4-(4-chlorophenyl)-4-hydroxy-piperidin-1-yl]-methanone (Compound No. 6)

Analysis by $^1$H NMR spectroscopy showed the following peaks (CDCl$_3$): δ 7.27-7.44 (m, 11H, ArH), 7.08-7.11 (d, 1H, Ar), 6.84-6.87 (d, 1H, Ar), 4.73-4.81 (m, 1H), 4.51-4.54 (m, 2H), 4.08 (m, 5H, OCH$_3$, CH$_2$), 3.00-3.92 (m, 8H), 1.58-2.15 (m, 16H). Mass spectroscopy showed the following peaks (m/z): 749 (M)$^+$, 750.1 (M+1)$^+$.

1-{1-[5-(4-Acetyl-4-phenyl-piperidine-1-carbonyl)-3-(3-cyclopentyloxy-4-methoxy-phenyl)-4,5-dihydro-isoxazole-5-carbonyl]-4-phenyl-piperidin-4-yl]-ethanone (Compound No. 2)

Analysis by $^1$H NMR spectroscopy showed the following peaks (CDCl$_3$): δ 7.28-7.35 (m, 11H, ArH), 7.015-7.078 (d, 1H, ArH), 6.804-6.85 (d, 1H, ArH), 4.677-4.807 (m, 1H, CH), 4.184-4.22 (m, 2H), 3.861 (s, 1H, —OCH$_3$), 3.38-3.44 (m, 2H), 2.32-3.15 (m, 8H), 1.8-2.08 (m, 22H). Mass spectroscopy showed the following peaks (m/z): 733 (M)$^+$, 734.4 (M+1)$^+$.

[3-(3-Cyclopentyloxy-4-methoxy phenyl)-5-(4-carboxylic Acid Tert Butyl-ester-piperazin-1-yl-carbonyl)-4,5-dihydroisoxazol-5-yl)-({4-carboxylic-acid-tert Butyl Ester Piperazine-1-yl)ethanone (Compound No. 1)

Analysis by $^1$H NMR spectroscopy showed the following peaks (CDCl$_3$): δ 7.26-7.31 (d, 1H, ArH), 7.06-7.09 (d, 1H, Ar), 6.87-6.84 (d, 1H, Ar), 4.81 (m, 1H, CH$_2$), 4.11-4.13 (m, 1H, CH$_2$), 3.88 (s, 3H, —OCH$_3$), 3.48-3.68 (m, 16H, 8×NCH$_2$) 2.96-3.05 (m, 2H, 2×CH$_2$), 1.85-1.97 (m, 8H, 4×CH$_2$), 1.47 (s, 19H, 9×CH$_3$). Mass spectroscopy showed the following peaks (m/z): 699 (M)$^+$, 700.600 (M+1)$^+$.

[5-(5-Benzyl-2,5-diazabicyclo[2.2.1]heptane-2-(carbonyl)-3-(3-cyclopentyloxy-4-methoxy-phenyl]-,5-dihydro-isoxozol-5-yl]-5-benzyl-2,5-diazabicylo-[2.2.1]hept-2-yl-ethanone (Compound No 8)

Analysis by $^1$H NMR spectroscopy showed the following peaks (DMSO): δ 6.99-7.34 (m, 13H, Ar), 4.809 (m, 1H), 4.4-4.53 (d, 1H), 3.5-3.91 (m, 13H), 2.7-3.08 (m, 5H), 1.56-1.8 (m, 16H). Mass spectroscopy showed the following peaks (m/z): 703 (M)$^+$, 704.4 (M+1)$^+$.

[3-(3-Cyclopentyloxy-4-methoxy-phenyl)-5-(hydroxymethyl-piperidine-1-carbonyl)-4,5-dihydro-isoxazol-5-yl]-(4-hydroxymethyl-piperidin-1-yl)-ethanone (Compound No. 7)

Analysis by $^1$H NMR spectroscopy showed the following peaks (CDCl$_3$): δ 7.26-7.34 (m, 1H), 7.08-7.11 (d, 1H), 6.83-6.85 (d, 1H), 4.79 (s, 1H), 3.87-3.96 (m, 5H, 3×OCH$_3$, CH$_2$), 3.36-3.68 (m, 8H), 2.8-3.05 (m, 4H), 1.67-1.89 (m, 20H).

Example 6

3-[3-Cyclopentyloxy-4-methoxy-phenyl)-7-methyl-1-oxa-2,7-diaza-spiro[4.4]non-2-ene-6,9-dione (Compound No. 36)

To a solution of the compound of formula XIII (0.070 g, 0.016 mmole, 1.0 eq) in dimethylformamide (1.0 mL), was added methyl amine (0.015 g, 0.16 mmol, 10.0 eq) and stirred the reaction mixture at 100° C. overnight. The resulting reaction mixture was diluted with water (10.0 mL) and extracted with ethyl acetate. The organic layer was washed with brine and dried over anhydrous sodium sulfate and evaporated under reduced pressure. The residue thus obtained was purified by column chromatography to furnish the title compound.

Yield: 50%.
M.P. 169-170° C.
Mass (m/z): 359.0 (M$^+$+1).
$^1$H NMR (CDCl$_3$): δ 7.3545 (d, 1H, Ar), 6.99-7.02 (d, 1H, Ar), 6.84-6.86 (d, 1H, Ar), 4.80-4.82 (m, 1H), 3.94-4.00 (d, 1H), 3.88 (s, 1H, OCH$_3$), 3.36-3.41 (m, 1H), 3.18-3.24 (m, 1H), 3.09 (s, 3H, —NCH$_3$), 2.8-2.83 (m, 1H), 1.59-2.01 (m, 8H).

Example 7

3-[3-(3-Cyclopentyloxy-4-methoxy-phenyl)-5-methyl-4,5-dihydro-isoxazol-5-carbonyl]-bicyclo[2.2.1]heptan-2-one (Compound No. 34)

The title compound was prepared following the procedure as described for the synthesis of the compound of Formula V, by using 3-methylene-2-norbornenone in place of methyl methacrylate.

Analysis by $^1$H NMR spectroscopy showed the following peaks (CDCl$_3$): 7.34 (s, 1H), 7.0-7.03 (d, 1H), 6.82-6.85 (d, 1H), 4.80-4.81 (m, 1H), 3.82 (s, 3H), 3.24-3.43 (m, 2H), 2.68-2.75 (d, 2H), 2.40-2.43 (d, 1H), 1.43-2.01 (m, 12H). Mass spectroscopy showed the following peaks (m/z): 355 (M)$^+$, 356.5 (M+1)$^+$.

Example 8

3-[3-Cyclopentyloxy-4-methoxy-phenyl)-1,7-dioxa-2-aza-spiro[4.41 non-2-ene-6-one (Compound No. 35)

The title compound was synthesized following the procedure as described for the synthesis of compound of Formula V, by using α-methylene-γ-butyrolactone in place of methyl methacrylate. The product had a melting point of 152.5-152.7° C.

Analysis by $^1$H NMR spectroscopy showed the following peaks (CDCl$_3$): 7.36 (d, 1H), 7.05 (d, 1H), 6.84-6.87 (d, 1H), 4.81-4.82 (m, 1H), 4.44-4.54 (m, 2H), 3.86-3.91 (m, 4H), 3.32-3.38 (d, 1H), 2.69-2.71 (m, 1H), 2.37-2.41 (m, 1H), 1.78-1.79 (m, 8H). Mass spectroscopy showed the following peaks (m/z): 331 (M)$^+$, 332.3 (M+1)$^+$.

Example 9

4-Difluoromethoxy-3-hydroxy-benzaldehyde and 3,4-bis-difluoromethoxy-benzaldehyde To a solution of the compound 3,4-dihydroxy benzaldehyde (commercially available) (0.072 mole) in dimethylformamide (70 mL), benzyltriethyl ammonium chloride (0.036 mole) was added. To the resulting reaction mixture was added sodium hydroxide solution (0.0018 mole of 30% solution) dropwise for about 3 minutes with a continuous flow of chloro-difluoro methane. The reaction mixture was acidified with dilute hydrochloric acid and diluted with water. The reaction mixture was extracted with ethyl acetate, washed with saturated solution of sodium chloride and concentrated under reduced pressure. The residue thus obtained was purified by column chromatography to furnish the title compounds.

Example 10

3-(3-Cyclopentyloxy-4-methoxy-phenyl)-1,7-dioxa-2-aza-spiro[4.4]non-2-ene (Compound No. 38)

Step a: Synthesis of 3-cyclopentyloxy-4-methoxy-benzaldehyde

To a solution of 3-hydroxy-4-methoxy-benzaldehyde (commercially available) (1 eq) was taken in dimethylformamide (10 mL), was added potassium iodide (0.1 eq) and potassium carbonate (2 eq). The reaction mixture was stirred at 70° C. and cyclopentyl bromide (2 eq) was added dropwise. The resulting reaction mixture was stirred at 70-80° C. for 16 hours. The reaction mixture was cooled and diluted with water, extracted with ethyl acetate and washed with saturated solution of sodium chloride. The organic solvent was removed under reduced pressure. The residue thus obtained was purified by column chromatography to furnish the title compound.

Step b: Synthesis of 3-cyclopentyloxy-4-methoxy-benzaldehyde Oxime

To a solution of the compound obtained from step a above (1 eq) in ethanol was added hydroxylamine hydrochloride (2 eq) and sodium acetate (2 eq). The reaction mixture was stirred at room temperature for 2-3 hours. The organic solvent was removed under reduced pressure. The residue thus obtained was diluted with water and extracted with ethyl acetate, washed with water, dried over anhydrous sodium sulphate and concentrated under reduced pressure to furnish the title compound.

Step c: Synthesis of 3-(3-Cyclopentyloxy-4-methoxy-phenyl)-5-methoxy carbonylmethyl-4,5-dihydro-isoxazol-5-carboxylic Acid Methyl Ester To a solution of the compound obtained from step b above (1 eq) in tetrahydrofuran, was added dimethylitaconate (2 eq). The reaction mixture was stirred at 60° C. for 0.5 hours followed by the addition of sodium hypochlorite solution. The resulting reaction mixture was stirred at 60-70° C. for 5-6 hours. Tetrahydrofuran was removed under reduced pressure. The residue thus obtained was diluted with water, extracted with ethyl acetate, washed with saturated sodium chloride solution and water. The reaction mixture was dried over anhydrous sodium sulphate and concentrated under reduced pressure to furnish the title compound.

Step d: Synthesis of 5-carboxymethyl-3-(3-cyclopentyloxy-4-methoxy-phenyl)-4,5-dihydro-isoxazol-5-carboxylic Acid To a solution of the compound obtained from step c in tetrahydrofuran (1.0 eq), was added and lithium hydroxide (5.0 eq) in water (as 5N solution). The mixture was stirred at room temperature over night. The solvent was removed under reduced pressure and the residue thus obtained was diluted with water and acidified with drops of concentrated hydrochloric acid. The organic compound was extracted with ethyl acetate, washed with brine, dried over anhydrous sodium sulphate and finally concentrated under reduced pressure to afford title organic compound.

Step e: Synthesis of 2-[3-(3-cyclopentyloxy-4-methoxy-phenyl)-5-hydroxymethyl-4,5-dihydro-isoxazol-5-yl]-ethanol To a solution of sodium borohydride (3 eq) in tetrahydrofuran, was added a solution of the compound obtained from step d above (1 eq) in tetrahydrofuran. To the resulting reaction mixture was added ethereal solution of trifluoroborane (3 eq) at 0° C. and stirred for 14-16 hours at ambient temperature. Sodium hydroxide (1N) solution was added at 0° C. and stirred for 1 hour. The reaction mixture was diluted with ethylacetate and water. The combined extract was washed with saturated solution of sodium chloride and concentrated under reduced pressure. The residue thus obtained was purified by column chromatography to furnish the title compound.

Step f: Synthesis of 3-(3-cyclopentyloxy-4-methoxyphenyl)-1,7-dioxaza-2-aza-spiro[4.4]non-2-ene To a solution of the compound obtained from step e above (1 eq) in tetrahydrofuran triphenylphosphine (1.12 eq) and succinimide (1 eq), was added diisopropyldiazadicarboxylate (1.14 eq). The reaction mixture was stirred at room temperature for overnight. The organic solvent was removed under reduced pressure and the residue thus obtained was purified by column chromatography to furnish the title compound.

Mass (m/z): 318 ($M^+$+1).

Particular analogs of 3-(3-Cyclopentyloxy-4-methoxyphenyl)-1,7-dioxa-2-aza-spiro[4.4]non-2-ene (Compound No. 38) which are described below can be prepared by reacting appropriate benzaldehyde group with alkyl halide, alkaryl halide or cycloalkyl halide.

3-(3-Cyclopropylmethoxy-4-methoxy-phenyl)-1,7-dioxa-2-aza-spiro[4.4]non-2-ene (Compound No. 39)

Mass (m/z): 304.11 ($M^+$+1).

3-(4-Difluoromethoxy-3-propoxy-phenyl)-1,7-dioxa-2-aza-spiro[4.4]non-2-ene

Mass (m/z): 328.15 ($M^+$+1).

3-(4-Difluoro-3-butoxy-phenyl)-1,7-dioxa-2-aza-spiro[4.4]non-2-ene (Compound No. 41)

Mass (m/z): 342.17 (M++1)

3-(4-Difluoromethoxy-3-isobutoxy-phenyl)-1,7-dioxa-2-aza-spiro[4.4]non-2-ene (Compound No. 42)

Mass (m/z): 328.15 (M++1)

3-(3-Cyclopropylmethoxy-4-difluoromethoxy-phenyl)-1,7-dioxa-2-aza-spiro[4.4]non-2-ene (Compound No. 43)

Mass (m/z): 340.17 ($M^+$+1)

3-(3-Benzyloxy-4-difluoromethoxy-phenyl)-1,7-dioxa-2-aza-spiro[4.4]non-2-ene (Compound No. 44)

Mass (m/z): 376.14.

3-(4-Difluoromethoxy-3-cyclopentyloxy-phenyl)-1,7-dioxa-2-aza-spiro[4.4]non-2-ene (Compound No. 45)

Mass (m/z): 354.11.

3-(3,4-Bis-difluoromethoxy-phenyl)-1,7-dioxa-2-aza-spiro[4.4]non-2-ene (Compound No. 46)

Mass (m/z): 366.18 ($M^+$+1).

3-(3-Benzyloxy-4-methoxy-phenyl)-1,7-dioxa-2-aza-spiro[4.4]non-2-ene (Compound No. 72)

Example 11

5-(1,7-dioxa-2-aza-spiro[4.4]non-2-en-3-yl)-2-methoxy-phenol (Compound No. 73

To a solution of the compound No. 72 (100 mg, 0.29 mmol) in methanol (5 mL), was added palladium on carbon (40 mg, 10%). The reaction mixture was evacuated with hydrogen gas and the resulting reaction mixture was allowed to stir at room temperature for 1 hour. The reaction mixture was filtered through celite pad. The filtrate was concentrated under reduced pressure to furnish the title compound. Yield=48 mg.

Mass (m/z): 250.19 ($M^+$+1).

Example 12

4-(1,7-dioxa-2-aza-spiro[4.4]non-2-en-3-yl)-2-methoxy-phenol (Compound No. 52)

Step a: Synthesis of 3-(4-benzyloxy-3-methoxy-phenyl)-1,7-dioxa-2-aza-spiro[4.4]non-2-ene The title compound was prepared following the procedure as described for the synthesis of compound No. 38 by using benzyl bromide in place of cyclopentyl bromide.

Step b: Synthesis of 4-(1,7-dioxa-2-aza-spiro[4.4]non-2-en-3-yl)-2-methoxy-phenol The title compound was prepared following the procedure as described for the synthesis of compound No. 73, by using compound No. 50 in place of compound No 72.

Mass (m/z): 250 (M$^+$+1).

Example 13

3-(3-Ethoxy-4-methoxy-phenyl)-1,7-dioxa-2-aza-spiro[4.4]non-2-ene (Compound No. 63)

To a solution of the compound No. 73 (1 eq) in dimethylformamide (10 mL), was added potassium iodide (0.1 eq) and potassium carbonate (2 eq). The reaction mixture was stirred at room temperature and ethyl bromide (2 eq) was added. The reaction mixture was stirred for overnight at room temperature. The reaction mixture was cooled and diluted with water, extracted with ethylacetate and washed with saturated solution of sodium chloride. The organic solvent was removed under reduced pressure. The residue thus obtained was purified by column chromatography to furnish the title compound. Yield=90%.

Mass (m/z): 278.18 (M$^+$+1).

Analogues of 3-(3-ethoxy-4-methoxy-phenyl)-1,7-dioxa-2-aza-spiro[4.4]non-2-ene (Compound No. 63) described below, can be prepared by using appropriate alkyl halide or cycloalkyl halide in place of ethyl bromide, respectively as applicable in each case.

3-(3-Butoxy-4-difluoromethoxy-phenyl)-1,7-dioxa-2-aza-spiro[4.4]non-2-ene (Compound No. 47)

Mass (m/z): 342 (M$^+$+1)

3-[3-(Bicyclo[2.2.1]hept-2-yloxy)-4-difluoromethoxy-phenyl]-1,7-dioxa-2-aza-spiro[4.4]non-2-ene (Compound No. 48)

Mass (m/z): 380 (M$^+$+1).

3-(4-Difluoromethoxy-3-methoxy-phenyl)-1,7-dioxa-2-aza-spiro[4.4]non-2-ene (Compound No. 49)

Mass (m/z): 300.06 (M$^+$+1).

3-(3-Cycloheptyloxy-4-difluoromethoxy-phenyl)-1,7-dioxa-2-aza-spiro[4.4]non-2-ene (Compound No. 51)

Mass (m/z): 382.28 (M$^+$+1).

3-[3-(Indan-2-yloxy)-4-methoxy-phenyl]-1,7-dioxa-2-aza-spiro[4.4]non-2-ene (Compound No. 53).

Mass (m/z): 366.37 (M$^+$+1).

3-(3,4-Dimethoxy-phenyl)-1,7-dioxa-2-aza-spiro[4.4]non-2-ene (Compound No. 62)

Mass (m/z): 264.8 (M$^+$+1).

3-(4-Methoxy-3-propoxy-phenyl)-1,7-dioxa-2-aza-spiro[4.4]non-2-ene (Compound No. 64)

Mass (m/z): 292.14 (M+1).

3-(3-Isopropoxy-4-methoxy-phenyl)-1,7-dioxa-2-aza-spiro[4.4]non-2-ene (Compound No. 65)

Mass (m/z): 292.14 (M$^+$+1).

3-(3-Butoxy-4-methoxy-phenyl)-1,7-dioxa-2-aza-spiro[4.4]non-2-ene (Compound No. 66)

Mass (m/z): 306.18 (M$^+$+1).

3-(3-Isobutoxy-4-methoxy-phenyl)-1,7-dioxa-2-aza-spiro[4.4]non-2-ene (Compound No. 67)

Mass (m/z): 306.18 (M$^+$+1).

3-[4-Methoxy-3-(3-methyl-butoxy)-phenyl]-1,7-dioxa-2-aza-spiro[4.4]non-2-ene (Compound No. 68)

Mass (m/z): 320.18 (M$^+$+1).

3-(3-Cyclohexyloxy-4-methoxy-phenyl)-1,7-dioxa-2-aza-spiro[4.4]non-2-ene (Compound No. 69)

Mass (m/z): 332.17 (M$^+$+1).

3-[4-Methoxy-3-(2-morpholin-4-yl-ethoxy)-phenyl]-1,7-dioxa-2-aza-spiro[4.4]non-2-ene (Compound No. 71)

Mass (m/z): 363.14 (M$^+$+1).

3-(3-Benzyloxy-4-methoxy-phenyl)-1,7-dioxa-2-aza-spiro[4.4]non-2-ene (Compound No. 72)

Mass (m/z): 340.14 (M+1).

Example 14

3-(4-Ethoxy-3-methoxy-phenyl)-1,7-dioxa-2-aza-spiro[4.4]non-2-ene (Compound No. 54)

The title compound was prepared following the procedure as described in Example 13, by using compound No. 52 in place of compound No. 73. Yield=79%.

Mass (m/z): 278.24 (M$^+$+1).

Analogues of 3-(4-ethoxy-3-methoxy-phenyl)-1,7-dioxa-2-aza-spiro[4.4]non-2-ene (Compound No. 54) described below, can be prepared by using appropriate alkyl halide or cycloalkyl halide in place of ethyl bromide, respectively, as applicable in each case.

3-(3-Methoxy-4-propoxy-phenyl)-1,7-dioxa-2-aza-spiro[4.4]non-2-ene (Compound No. 55)

Mass (m/z): 292.28 (M$^+$+1).

3-(4-Isopropoxy-3-methoxy-phenyl)-1,7-dioxa-2-aza-spiro[4.4]non-2-ene (Compound 56)

Mass (m/z): 292.28 (M$^+$+1).

3-(4-Butoxy-3-methoxy-phenyl)-1,7-dioxa-2-azaspiro[4.4]non-2-ene (Compound No. 57)

Mass (m/z): 366.18 (M$^+$+1).

3-(4-Cyclopentyloxy-3-methoxy-phenyl)-1,7-dioxa-2-aza-spiro[4.4]non-2-ene (Compound No. 58)

Mass (m/z): 318.27 (M$^+$+1).

3-(4-Isobutoxy-3-methoxy-phenyl)-1,7-dioxa-2-aza-spiro[4,4]non-2-ene (Compound No. 59)

Mass (m/z): 306.25 (M++1).

3-(4-Cyclohexyloxy-3-methoxy-phenyl)-1,7-dioxa-2-aza-spiro[4.4]non-2-ene (Compound No. 60)

Mass (m/z): 332.25 (M++1).

3-(4-Cyclopropylmethoxy-3-methoxy-phenyl)-1,7-dioxa-2-aza-spiro[4.4]non-2-ene (Compound No. 61)

Mass (m/z): 304.24 (M$^+$+1).

Example 15

4-(Methylene-cyclohexyl)-carbamic Acid Tert-butyl Ester

Step a: synthesis of (4-hydroxy-cyclohexyl)-carbamic Acid Tert-butyl Ester

To a solution of the compound trans-amino cyclohexanol hydrochloride (4.0 g, 26.4 mmol) in dichloromethane (100 mL), was added triethylamine (7.35 mL, 52.8 mmol) and stirred the reaction mixture for 30 min. The reaction mixture was cooled to 0° C. followed by the addition of tert-butyl dicarbonate (8.64 g, 39.6 mmol) in dichloromethane (10.0 mL). The resulting reaction mixture was stirred for 8 hours. The reaction mixture was diluted with water and stirred vigorously for 30 minutes. The organic layer was separated, washed with water and brine and dried over anhydrous sodium sulphate. The organic layer was concentrated and purified by column chromatography to furnish the title compound.
Yield=5.05 g.

Step b: Synthesis of (4-oxo-cyclohexyl)-carbamic Acid Tert-butyl Ester

To a solution of the compound obtained from step a above (5 g, 23.4 mmol) in dichloromethane (100 mL), was added pyridinium chlorochromate (7.6 g, 35.0 mmol) and celite (5.0 g). The reaction mixture was stirred at room temperature for 2 hours. Dichloromethane was evaporated under reduced pressure and the residue was diluted with ethylacetate. The reaction mixture filtered through celite pad and concentrated under reduced pressure. The crude compound thus obtained was purified by column chromatography to furnish the title compound.
Yield: 3.5 g.

Step c: Synthesis of 4-methylene-cyclohexyl-carbamic Acid Tert-butyl Ester

Triphenylmethylphosphonium iodide (17.2 g, 42.5 mmol) and potassium tert-butoxide (4.13 g, 36.8 mmol) were taken together under nitrogen atmosphere and dry tetrahydrofuran (150 mL) was added at room temperature. The reaction mixture was stirred for 3 hours at room temperature. To the resulting reaction mixture was added a solution of the compound obtained form step b above in dry tetrahydrofuran under nitrogen atmosphere and cooled to 0° C. followed by stirring for 10 hours at room temperature. The reaction mixture was quenched with water (5.0 mL) and concentrated under reduced pressure. The residue thus obtained was dissolved in dichloromethane, washed with water, brine and dried over anhydrous sodium sulphate. The organic layer was concentrated under reduced pressure and the residue thus obtained was purified by column chromatography to furnish the title compound. Yield=2.1 g Mass (m/z): 211 (M$^+$+1).

Example 16

2-(4-Methylene-cyclohexyl)-isoindole-1,3-dione

Aminocyclohexanol hydrochloride (6.3 g, 41.6 mmol) and triethylamine (11.6 mL, 83.1 mmol) were stirred in toluene (150 mL) at room temperature for 1 hour. To this was added phthalic anhydride (7.4 g, 49.9 mmol) and the reaction mixture was stirred at 120-130° C. The by-product water was removed from the reaction mixture. Toluene was concentrated under reduced pressure. The crude compound thus obtained was purified by column chromatography using ether in hexane solvent mixture (2:1) as eluent to furnish the title compound (8.5 g, 84%).

Mass (m/z): 241 (M$^+$+1).

Example 17

[3-(3-Cyclopentyloxy-4-methoxy-phenyl)-1-oxa-2-aza-spiro[4.5]dec-2-en-8-yl]-carbamic Acid Isopropyl Ester (Compound No. 79)

To a solution of 4-methylene-cyclohexyl-carbonic acid tert-butyl ester (0.55 g, 2.62 mmol), 3-cyclopentyloxy-4-methoxy-benzaldehyde oxime (0.62 g, 2.62 mmol) and pyridine (1 mL) in 20% chloroform in dichloromethane (50 mL) at room temperature under nitrogen atmosphere was added sodium hypochlorite (4.1, 5.0 mL, 2.62 mmol) dropwise. The resulting reaction mixture was stirred for 15 hours at room temperature followed by the addition of sodium hypochlorite (4%, 5.0 mL, 2.62 mmol) dropwise. The resulting reaction mixture was stirred for 15 hours at room temperature followed by the addition of sodium hypochlorite (4%, 5 mL, 2.62 mmol). The reaction mixture was again stirred for 15 hours. The organic layer was washed with water, brine, dried over anhydrous sodium sulphate and concentrated under reduced pressure. The residue thus obtained was purified by column chromatography to furnish the title compound. Yield=0.85 g.

Mass (m/z): 445

Analogues of [3-(3-cyclopentyloxy-4-methoxy-phenyl)-1-oxa-2-aza-spiro[4.5]dec-2-en-8-yl]-carbamic acid isopropyl ester (Compound No. 79) described below can be prepared by using appropriate methylene-cycloalkyl group in place of 4-methylene-cyclohexyl-8-carbonic acid tert-butyl ester, respectively, as applicable in each case.

7-(3-Cyclopentyloxy-4-methoxy-phenyl)-5-oxa-6-aza-spiro[3.4]oct-6-ene (Compound No. 82)

Mass (m/z): 302 (M$^+$+1).

3-(3-Cyclopentyloxy-4-methoxy-phenyl)-1-oxa-2,7-aza-spiro[4.5]dec-2-ene (Compound No. 83)

Mass (m/z): 332.22 (M$^+$+1).

Example 18

2-[3-(3-Cyclopentyloxy-4-methoxy-phenyl)-1-oxa-2-aza-spiro[4.5]dec-2-ene-8-yl]-isoindole-1,3-dione (Compound No. 81)

The title compound was prepared following the procedure as described in Example 15, by using 2-(4-methylene-cyclohexyl)-isoindole-1,3-dione in place of 4-methylene-cyclohexyl-carbamic acid tert-butyl ester. Yield; 0.9 g.
Mass (m/z): 475 (M$^+$+1).

Example 19

3-(3-Cyclopentyloxy-4-methoxy-phenyl)-1-oxa-2-aza-spiro[4.5]dec-2-en-8-ylamine (Compound No. 80)

To a solution of the compound No. 79 (0.26 g, 0.54 mmol) in dichloromethane (50 mL), was added methanolic hydrochloric acid (5.9 mL, 29.3 mmol) at 0° C. and the reaction mixture was stirred at room temperature for 7 hours. The resulting reaction mixture was concentrated under reduced pressure, washed with saturated sodium bicarbonate solution and extracted with ether. Organic layer was concentrated under reduced pressure. The residue thus obtained was purified by column chromatography to furnish the title compound. Yield: 0.19 g.
Mass (m/z): 345 (M$^+$+1).

Example 20

3-(3-Cyclopentyloxy-4-methoxy-phenyl)-1-oxa-2,7-diaza-spiro[4.4]non-2-ene-7-carboxylic Acid Tert-butyl Ester (Compound No. 84)

Step a: Synthesis of 3-hydroxy-pyrrolidine-1-carboxylic Acid Tert-butyl Ester To a solution of tert-butyl dicarbonate (9.06 g, 0.02325 mol) in dichloromethane (25 mL) at 0° C., was added a solution of R(+)-3-hydroxy pyrrolidine in dichloromethane (15 mL). The reaction mixture was stirred for 2 hours at ambient temperature. Reaction mixture was poured into water and extracted with dichloromethane. The organic layer was washed with water, dried over anhydrous sodium sulphate and concentrated under reduced pressure. The residue thus obtained was purified by column chromatography using ethyl acetate in hexane (40:60) solvent mixture as eluent to furnish the title compound. Yield=4.0 g.

Step b: Synthesis of 3-oxo-pyrrolidine-1-carboxylic Acid Tert-butyl Ester

To a solution of the compound obtained from step a above (500 mg, 0.0027 mole) in dichloromethane (10 mL) was added celite (400 mg) and stirred at room temperature for 10 minutes. Pyridinium chlorochromate (869 mg, 0.0040 mole) was added portionwise over a period of 5 minutes. The reaction mixture was stirred at room temperature for 3 hours. Dichloromethane was removed under reduced pressure followed by the addition of ethyl acetate. The resulting reaction mixture was again stirred for 10 minutes and filtered through celite pad. The organic layer was removed under reduced pressure. The residue thus obtained was purified by column chromatography using ethyl acetate in hexane (30:70) solvent mixture as eluent to furnish the title compound. Yield: 350 mg.

Step c: Synthesis of 3-methylene-pyrrolidine-1-carboxylic Acid Tert-butyl Ester The solution of a compound triphenylmethylphosphonium iodide (2.24 g, 0.0055 mole), potassium tert-butoxide (517 mg, 0.0046 mole) in tetrahydrofuran (10 mL) was stirred at −78° C. for 20 minutes and then at room temperature for 1 hour. To the resulting reaction mixture was added a solution of 3-methylene-pyrrolidine-1-carboxylic acid tert-butyl ester (340 mg, 0.0018 mol) in tetrahydrofuran (10 mL) at 0° C. The resulting reaction mixture was stirred at room temperature for 10 min. followed by diluting it with water. Tetrahydrofuran was evaporated under reduced pressure, extracted with ethyl acetate, washed with anhydrous sodium sulphate and concentrated under reduced pressure. The residue thus obtained was purified by column chromatography using ethylacetate in hexane (10:90) solvent mixture as eluent. Yield: 170 mg.

Step d: Synthesis of 3-(3-cyclopentyloxy-4-methoxy-phenyl)-1-oxa-2,7-diaza-spiro[4.4]non-2-ene-7-carboxylic Acid Tert-butyl Ester The compound obtained from step c above (170 mg, 0.0010 mole) and 3-cyclopentyloxy-4-methoxy-benzaldehyde oxime (236 mg, 0.0010 mole) were taken in dichloromethane (20%) in chloroform followed by the addition of pyridine (2 drops). The reaction mixture was stirred at room temperature for 10 minutes followed by the addition of sodium hypochlorite (2 mL) dropwise. The resulting reaction mixture was stirred at room temperature for 4 hours. Tetrahydrofuran was evaporated under reduced pressure followed by diluting it with water. The compound was extracted with ethyl acetate, washed with brine, dried over anhydrous sodium sulphate and evaporated under reduced pressure. The residue thus obtained was purified by column chromatography to furnish the title compound. Yield: 200 mg.

The analogues of 3-(3-cyclopentyloxy-4-methoxy-phenyl)-1-oxa-2,7-diaza-spiro[4.4]non-2-ene-7-carboxylic acid tert-butyl ester (Compound No. 84) described below, can be prepared by using appropriate piperidinyl group in place of 3-methylene-pyrrolidine-1-carboxylic acid tert-butyl ester.

3-(3-Cyclopentyloxy-4-methoxy-phenyl)-1-oxa-2,8-diaza-spiro[4.5]dec-2-ene-8-carboxylic acid tert-butyl ester (Compound No. 74)

Example 21

3-(3-Cyclopentyloxy-4-methoxy-phenyl)-1-oxa-2,7-diaza-spiro[4.4]non-2-ene (Compound No. 85)

The title compound was prepared following the procedure as described in Example 19.
Yield: 60%.
Mass (m/z): 317.16 (M$^+$−HCl).

The analogues of (Compound No. 85) described below, can be prepared by deprotecting appropriate amino group, respectively, as applicable in each case.

Hydrochloride salt of 3-(3-cyclopentyloxy-4-methoxy-phenyl)-1-oxa-2,8-diaza-spiro[4.5]dec-2-ene (Compound No. 75)

Mass (m/z): 331.25 (M$^+$–HCl).

Example 22

3-(3-Cyclopentyloxy-4-methoxy-phenyl)-1-oxa-2,8-diaza-spiro[4.5]dec-2-ene-8-carboxylic acid-(2,6-difluoro-phenyl)-amide (Compound No. 77)

To a solution of the compound No. 75 in dichloromethane (5 mL) was added 1,3-difluoro-2-isocyanato-benzene (0.2954 mol) and stirred the reaction mixture at room temperature for overnight. The reaction mixture was concentrated under reduced pressure. The residue thus obtained was purified by column chromatography to furnish the title compound. Yield: 96 mg.

Mass (m/z): 486.07 (M$^+$+1).

Analogues of 3-(3-cyclopentyloxy-4-methoxy-phenyl)-1-oxa-2,8-diaza-spiro[4.5]dec-2-ene-8-carboxylic acid-(2,6-difluoro-phenyl)-amide (Compound No. 77) described below, can be prepared by using appropriate isocyanate group in place of 1,3-difluoro-isocyanate-benzene, respectively, as applicable in each case.

4-Chloro-N-[3-(3-cyclopentyloxy-4-methoxy-phenyl)-1-oxa-2,8-diaza-spiro[4.5]dec-2-ene-8-carbonyl]-benzene sulfonamide (Compound No. 76)

Mass (m/z): 548.01 (M$^+$+1).

3-(3-Cyclopentyloxy-4-methoxy-phenyl)-1-oxa-2,8-diaza-spiro[4.5]dec-2-ene-8-carboxylic acid (2,6-difluoro-phenyl)-amide (Compound No. 77)

Mass (m/z): 486.07 (M$^+$+1).

Example 23

Efficacy of Compounds as PDE IV Inhibitors

PDE-IV Enzyme Assay

The efficacy of compounds as PDE-4 inhibitor was determined by an enzyme assay (Burnouf et al.; *J. Med. Chem.*, 2000, 43:4850-4867). The PDE-4 enzyme source used was U937 cell cytosolic fraction prepared by sonication. The enzyme reaction was carried out, with the cytosolic fraction as the enzyme source, in the presence of cAMP (1 μM) at 30° C. in the presence or absence of NCE for 45-60 min. An aliquot of this reaction mixture was taken further for the ELISA assay to determine level of cAMP in the sample. The concentration of the cAMP in the sample directly correlates with the degree of PDE-4 enzyme inhibition. Results were expressed as percent control and the IC$_{50}$ values of test compounds were reported to be in the range of μM to low nm.

We claim:

1. A compound having the structure of Formula I,

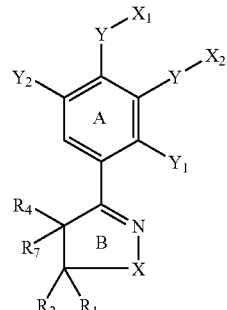

Formula I and its pharmaceutically acceptable salts, wherein

X is O

Y is O $Y_1$, $Y_2$, $R_7$ and $R_4$ are H;

$X_1$ and $X_2$ are independently selected from the group consisting of hydrogen, an alkyl group having 1 to 5 carbon atoms, wherein one or more of the hydrogen atoms of the alkyl group may be substituted with a halo, aryl, cycloalkyl, or heterocyclyl group, and a cycloalkyl group having 5 to 9 carbon atoms;

$R_1$ is an alkyl group of 1-2 carbon atoms, or —CH$_2$—CO—R$_p$ wherein R$_f$ is an optionally substituted 5- to 7-membered heterocyclyl ring having 1 to 2 nitrogen atoms, wherein the substituents are selected from the group consisting of alkyl, —CO-alkyl, —COOalkyl, aralkyl, aryl, and hydroxyalkyl groups $R_2$ is substituted —COR$_p$— wherein R$_p$ is an optionally substituted 5- to 7-membered heterocyclyl ring having 1 or 2 nitrogen atoms, wherein the substituents are selected from the group consisting of alkyl, —CO-alkyl, —COOH, heterocyclyl, oxo, —COOalkyl, —CONH$_2$, —CONH-alkyl, —CON(alkyl)$_2$, (3-aryl-5-alkyl-4,5-dihydro-isoxazol-5-yl)-methanonyl, hydroxyl, aralkyl, aryl, wherein the alkyl or aryl groups may be further substituted with hydroxyl, cycloalkyl or halo groups, with the proviso that when the substituent is (3-aryl-5-alkyl-4,5-dihydro-isoxazol-5-yl)-methanonyl group, R$_p$ is a 1,4-diazepan ring and the substitution is on the nitrogen atom, Alternatively, $R_1$ and $R_2$ may together form an optionally substituted cycloalkyl ring having 4 to 9 carbons, wherein the substituents are selected from the group consisting of oxo, NH$_2$, NH—COO-alkyl, —N—(COO-alkyl)$_2$, and phthalimido groups, or an optionally substituted 5- to 6-membered heterocyclyl ring having 1 to 2 oxygen or nitrogen atoms, wherein the substituents are selected from the group consisting of alkyl, oxo, NH$_2$, COOalkyl, —CONH—SO$_2$-aryl and CO—NH-aryl, with the proviso that that the heterocyclyl ring is not a dihydrofuran ring.

2. The compound according to claim 1, wherein $X_1$ is selected from the group consisting of methyl, ethyl, butyl, propyl, isopropyl, isobutyl, difluoromethyl, cyclopropylmethyl, and benzyl groups and $X_2$ is independently selected from the group comprising of methyl, ethyl, butyl, propyl, isopropyl, isobutyl, morpholinylethyl, cyclopentyl, cyclohexyl, cycloheptyl, indanyl, and benzyl groups.

3. The compound according to claim 1, wherein R$_p$ is selected from the group containing piperazinyl, piperidinyl, pyrrolidinyl, and diaza-bicycloheptyl rings.

4. The compound according to claim 1, wherein the substituents on the 5- to 6-membered heterocyclyl ring having 1 to 2 nitrogen atoms formed by R$_1$ and R$_2$ are —NH$_2$, difluorophenylaminocarbonyl, dichlorophenylaminocarbonyl, indanedione, tertbutylcarbamate, carboxy, tert-butoxycarbonyl or chlorophenylsulphonamidecarbonyl.

5. A compound according to claim 1, which is selected from the group consisting of compounds:

2-[3-(3-Cyclopentyloxy-4-methoxyphenyl)-5-(4-carboxylic acid tert butyl-ester-piperazin-1-yl-carbonyl)-4,5-dihydroisoxazol-5-yl]-(4-carboxylic acid tert butyl-ester-piperazine-1-yl)ethanone (Compound No. 1), 1-{1-(4-Acetyl-4-phenyl-piperidine-1-carbonyl)-3-(3-cyclopentyloxy-4-methoxyphenyl)-4,5-dihydroisoxazole-5-yl]-4-acetyl-4-phenyl-piperidin-4-yl]-ethanone (Compound No. 2),

[3-(3-Cyclopentyloxy-4-methoxyphenyl)-5-(pyrrolidine-1-carbonyl)-4,5-dihydroisoxazol-5-yl]-pyrrolidin-1-yl-ethanone (Compound No. 3),

[3-(3-Cyclopentyloxy-4-methoxyphenyl)-5-(piperidine-1-carbonyl)-4,5-dihydroisoxazol-5-yl]-piperidin-1-yl-ethanone (Compound No. 4), 2-[3-(3-Cyclopentyloxy-4-methoxyphenyl)-5-(pyrrolidin-2-carboxylic acid methyl ester-1-carbonyl)-4,5-dihydro-isoxazol-5-yl]-[pyrrolidine-2-carboxylic acid methyl ester-5-yl]ethanone (Compound No. 5),

[5-[4-(4-Chlorophenyl)-4-hydroxy-piperidine-1-carbonyl]-3-(3-cyclopentyloxy-4-methoxyphenyl)-4,5-dihydro-isoxazol-5-yl]-[4-(4-chlorophenyl)-4-hydroxy-piperidin-1-yl]-ethanone (Compound No. 6),

[3-(3-Cyclopentyloxy-4-methoxyphenyl)-5-(hydroxymethyl-piperidine-1-carbonyl)-4,5-dihydro-isoxazol-5-yl]-(4-hydroxymethyl-piperidin-1-yl)-ethanone (Compound No. 7), 2-[5-(5-Benzyl-2,5-diazabicyclo[2.2.1]heptane-2-carbonyl)-3-(3-cyclopentyloxy-4-methoxy-phenyl)-4,5-dihydro-isoxazol-5-yl](5-benzyl-2,5-diazabicyclo[2.2.1]hept-2-yl)ethanone (Compound No. 8),

[3-(3-Cyclopentyloxy-4-methoxyphenyl)-5-methyl-4,5-dihydro-isoxazol-5-yl]-piperidin-1-yl-methanone (Compound No. 9), 4-[3-(3-Cyclopentyloxy-4-methoxyphenyl)-5-methyl-4,5-dihydroisoxazole-5-carbonyl]-piperazine-1-carboxylic acid tert-butyl ester (Compound No. 10), 1-[3-(3-Cyclopentyloxy-4-methoxyphenyl)-5-methyl-4,5-dihydroisoxazole-carbonyl]-pyrrolidin-2-carboxylic acid (Compound No. 11), 1-[3-(3-Cyclopentyloxy-4-methoxyphenyl)-5-methyl-4,5-dihydro-isoxazol-5-carbonyl]-pyrrolidine-2-carboxylic acid methyl ester (Compound No. 12),

[3-(3-Cyclopentyloxy-4-methoxyphenyl)-5-methyl-4,5-dihydroisoxazole-5-yl]-pyrrolidin-1-yl-methanone (Compound No. 13),

[1,4]Bipiperidinyl-1'-yl-[3-(3-cyclopentyloxy-4-methoxy-phenyl)-5-methyl-4,5-dihydro-isoxazol-5-yl]-methanone (Compound No. 14), 1-{[3-(3-Cyclopentyloxy-4-methoxy-phenyl)-5-methyl-4,5-dihydro-isoxazole-5-carbonyl]-4-phenyl-piperidine-4-yl}ethanone (Compound No. 15),

[3-(3-Cyclopentyloxy-4-methoxyphenyl)-5-methyl-4,5-dihydro-isoxazol-5-yl]-(4-methyl-piperazin-1-yl)-methanone (Compound No. 16),

[3-(3-Cyclopentyloxy-4-methoxyphenyl)-5-methyl-4,5-dihydro-isoxazol-5-yl]-piperazin-1-yl-methanone (Compound No. 17),

[4-(4-Chloro-phenyl)-4-hydroxy-piperidin-1-yl]-[3-(3-cyclopentyloxy-4-methoxyphenyl)-5-methyl-4,5-dihydroisoxazol-5-yl]-methanone (Compound no. 18), {4-[3-(3-Cyclopentyloxy-4-methoxyphenyl)-5-methyl-4,5-dihydroisoxazole-5-carbonyl]-[1,4]diazepan-1-yl}-[3-(3-cyclopentyloxy-4-methoxyphenyl)-5-methyl-4,5-dihydro-isoxazol-5-yl]-methanone (Compound No. 19),

[3-(3-Cyclopentyloxy-4-methoxyphenyl)-5-methyl-4,5-dihydro-isoxazol-5-yl]-(4-cyclopropylmethyl-piperazin-1-yl)-methanone (Compound No. 20)

[3-(3-Cyclopentyloxy-4-methoxyphenyl)-5-methyl-4,5-dihydro-isoxazol-5-yl]-(4-isobutyl-1-piperazin-1-yl)-methanone (Compound No. 21),

[3-Hydroxymethyl-piperidin-1-yl]-[3-(3-cyclopentyloxy-4-methoxyphenyl)-5-methyl-4,5-dihydro-isoxazol-5-yl]-methanone (Compound No. 22),

[3-(3-Cyclopentyloxy-4-methoxyphenyl)-5-methyl-4,5-dihydro-isoxazol-5-yl]-(4-hydroxy-piperidin-1-yl)-methanone (Compound No 23), (4-Benzyl-piperidin-1-yl)-[3-(3-cyclopentyloxy-4-methoxyphenyl)-5-methyl-4,5-dihydro-isoxazol-5-yl]-methanone (Compound No 24), 1-[3-(3-Cyclopentyloxy-4-methoxyphenyl)-5-methyl-4,5-dihydroisoxazole-5-carbonyl]-piperidin-4-one (Compound No. 25),

[4-(4-Bromophenyl)-4-hydroxy-piperidin-1-yl]-[3-(3-cyclopentyloxy-4-methoxyphenyl)-5-methyl-4,5-dihydro-isoxazol-5-yl]-methanone (Compound No 26), (5-Benzyl-2,5-diaza-bicyclo[2.2.1]hept-2-yl)-[3-(3-cyclopentyloxy-4-methoxy-phenyl)-5-methyl-4,5-dihydro-isoxazol-5-yl]methanone (Compound No. 27), (4-Benzyl-piperazin-1-yl)-[3-(3-cyclopentyloxy-4-methoxyphenyl)-5-methyl-4,5-dihydro-isoxazol-5-yl]-methanone (Compound No. 28), 1-[3-(3-Cyclopentyloxy-4-methoxyphenyl)-5-methyl-4,5-dihydroisoxazole-5-carbonyl]-pyrrolidin-2-carboxylic acid methyl amide (Compound No. 29), 1-[3-(3-Cyclopentyloxy-4-methoxyphenyl)-5-methyl-4,5-dihydroisoxazole-5-carbonyl]-pyrrolidine-2-carboxylic acid diethyl amide (Compound No. 30),

[3-(3-Cyclopentyloxy-4-methoxyphenyl)-5-methyl-4,5-dihydro-isoxazol-5-yl]-(2-hydroxymethyl-pyrrolidin-1-yl)-methanone (Compound No. 31), 1-[3-(3-Cyclopentyloxy-4-methoxyphenyl)-5-methyl-4,5-dihydroisoxazole-5-carbonyl]-piperidine-2-carboxylic acid methyl ester (Compound No. 32),

[3-(3-Cyclopentyloxy-4-methoxyphenyl)-5-methyl-4,5-dihydro-isoxozole-5-carboxyl]-pyrrolidine-2-carboxylic acid amide (Compound No. 33), 3'-[3-(Cyclopentyloxy)-4-methoxyphenyl]-3H,4'H-spiro[bicyclo[2.2.1]heptane-2,5'-isoxazol]-3-one dihydroisoxazole (Compound No. 34), 3-[3-Cyclopentyloxy-4-methoxy-phenyl]-1,7-dioxa-2-aza-spiro[4.4]non-2-en-6-one (Compound No. 35), 3-[3-Cyclopentyloxy-4-methoxy-phenyl]-7-methyl-1-oxa-2,7-diaza-spiro[4.4]non-2-ene-6,9-dione (Compound No. 36), 3-(3-Cyclopentyloxy-4-methoxy-phenyl)-5-methyl-4,5-dihydro-isoxazol-5-yl-(2-methoxymethyl-pyrrolidin-1-yl)-methanone (Compound No. 37), 3-(3-Cyclopentyloxy-4-methoxyphenyl)-1,7-dioxa-2-aza-spiro[4.4]non-2-ene (Compound No. 38), 3-(3-Cyclopropylmethoxy-4-methoxyphenyl)-1,7-dioxa-2-aza-spiro[4.4]non-2-ene (Compound No. 39),
3-(4-Difluoromethoxy-3-propoxy-phenyl)-1,7-dioxa-2-aza-spiro[4.4]non-2-ene (Compound No. 40),
3-(4-Difluoromethoxy-3-butoxy-phenyl)-1,7-dioxa-2-aza-spiro[4.4]non-2-ene (Compound No. 41),
3-(4-Difluoromethoxy-3-isobutoxy-phenyl)-1,7-dioxa-2-aza-spiro[4.4]non-2-ene (Compound No. 42),
3-(3-Cyclopropylmethoxy-4-difluoromethoxyphenyl)-1,7-dioxa-2-aza-spiro[4.4:non-2-ene (Compound No. 43),
3-(3-Benzyloxy-4-difluoromethoxyphenyl)-1,7-dioxa-2-aza-spiro[4.4]non-2-ene (Compound No. 44),
3-(4-Difluoromethoxy-3-cyclopentyloxy-phenyl)-1,7-dioxa-2-aza-spiro[4.4]non-2-ene (Compound No. 45),
3-(3,4-Bis-difluoromethoxyphenyl)-1,7-dioxa-2-aza-spiro[4.4]non-2-ene (Compound No. 46),
3-[3-(Bicyclo[2.2.1]hept-2-yloxy)-4-difluoromethoxyphenyl]-1,7-dioxo-2-aza-spiro[4.4]non-2-ene (Compound No. 48),
3-(4-Difluoromethoxy-3-methoxyphenyl)-1,7-dioxa-2-aza-spiro[4.4]non-2-ene (Compound No. 49),
3-(4-Benzyloxy-3-methoxyphenyl)-1,7-dioxa-2-aza-spiro[4.4]non-2-ene (Compound No. 50),
3-(3-Cycloheptyloxy-4-difluoromethoxyphenyl)-1,7-dioxa-2-aza-spiro[4.4]non-2-ene (Compound No. 51),
4-(1,7-Dioxa-2-aza-spiro[4.4]non-2-en-3-yl)-2-methoxyphenol (Compound No. 52),
3-[3-(indan-2-yloxy)-4-methoxyphenyl]-1,7-dioxa-2-aza-spiro[4.4]non-2-ene (Compound No. 53),
3-(4-Ethoxy-3-methoxyphenyl)-1,7-dioxa-2-aza-spiro[4.4]non-2-ene (Compound No. 54),
3-(3-Methoxy-4-propoxy-phenyl)-1,7-dioxa-2-aza-spiro[4.4]non-2-ene (Compound No. 55),
3-(4-Isopropoxy-3-methoxyphenyl)-1,7-dioxa-2-aza-spiro[4.4]non-2-ene (Compound No. 56),
3-(4-Butoxy-3-methoxyphenyl)-1,7-dioxa-2-aza-spiro[4.4]non-2-ene (Compound No. 57),
3-(4-Cyclopentyloxy-3-methoxyphenyl)-1,7-dioxa-2-aza-spiro[4.4]non-2-ene (Compound No. 58),
3-(4-(Isobutoxy-3-methoxyphenyl)-1,7-dioxa-2-aza-spiro[4.4]non-2-ene (Compound No. 59),
3-(4-Cyclohexyloxy-3-methoxyphenyl)-1,7-dioxa-2-aza-spiro[4.4]non-2-ene (Compound No. 60),
3-(4-Cyclopropylmethoxy-3-methoxyphenyl)-1,7-dioxa-2-aza-spiro[4.4]non-2-ene (Compound No. 61),
3-(3,4-Dimethoxyphenyl)-1,7-dioxa-2-aza-spiro[4.4]non-2-ene (Compound No. 62),
3-(3-Ethoxy-4-methoxyphenyl)-1,7-dioxa-2-aza-spiro[4.4]non-2-ene (Compound No. 63),
3-(4-Methoxy-3-propoxy-phenyl)-1,7-dioxa-2-aza-spiro[4.4]non-2-ene (Compound No. 64),
3-(3-Isopropoxy-4-methoxyphenyl)-1,7-dioxa-2-aza-spiro[4.4]non-2-ene (Compound No. 65),
3-(3-Butoxy-4-methoxyphenyl)-1,7-dioxa-2-aza-spiro[4.4]non-2-ene (Compound No. 66),
3-(3-Isobutoxy-4-methoxyphenyl)-1,7-dioxa-2-aza-spiro[4.4]non-2-ene (Compound No. 67),
3-[4-Methoxy-3-(3-methyl-butoxy)-phenyl]-1,7-dioxa-2-aza-spiro[4.4]non-2-ene (Compound No. 68),
3-(3-Cyclohexyloxy-4-methoxyphenyl)-1,7-dioxa-2-aza-spiro[4.4]non-2-ene (Compound No. 69),
3-(3-Cycloheptyloxy-4-methoxyphenyl)-1,7-dioxa-2-aza-spiro[4.4]non-2-ene (Compound No. 70),
3-[4-Methoxy-3-(2-morpholin-4-yl-ethoxy)-phenyl]-1,7-dioxa-2-aza-spiro[4.4]non-2-ene (Compound No. 71),
3-(3-Benzyloxy-4-methoxyphenyl)-1,7-dioxa-2-aza-spiro[4.4]non-2-ene (Compound No. 72),
5-(1,7-Dioxa-2-aza-spiro[4.4]non-2-en-3-yl)-2-methoxyphenol (Compound No. 73),
3-(3-Cyclopentyloxy-4-methoxyphenyl)-1-oxa-2,8-diaza-spiro[4.5]dec-2-ene-8-carboxylic acid tert-butyl ester (Compound No. 74),
Hydrochloride salt of 3-(3-cyclopentyloxy-4-methoxyphenyl)-1-oxa-2,8-diaza-spiro[4.5]dec-2-ene (Compound No. 75),
4-Chloro-N-[3-(3-cyclopentyloxy-4-methoxyphenyl)-1-oxa-2,8-diaza-spiro[4,5]dec-2-ene-8-carbonyl]-benzene sulfonamide (Compound No. 76),
3-(3-Cyclopentyloxy-4-methoxyphenyl)-1-oxa-2,8-diaza-spiro[4.5]dec-2-ene-8-carboxylic acid-(2,6-difluoro-phenyl)-amide (Compound No. 77),
3-[(3-Cyclopentyloxy-4-methoxyphenyl)-1-oxa-2,8-diaza-spiro[4.5]dec-2-ene-8-carboxylic acid-(2,4-dichloro-phenyl)-amide (Compound No. 78),
[3-(3-Cyclopentyloxy-4-methoxyphenyl)-1-oxa-2-aza-spiro[4.5]dec-2-en-8-yl]-carbamic acid tert-butyl ester (Compound No. 79),
Hydrochloride salt of 3-(3-cyclopentyloxy-4-methoxyphenyl)-1-oxa-2-aza-spiro[4.5]dec-2-en-8-ylamine (Compound No. 80),
2-[3-(3-Cyclopentyloxy-4-methoxyphenyl)-1-oxa-2-aza-spiro[4.5]dec-2-en-8-yl]-isoindole-1,3-dione (Compound No. 81),
7-(3-Cyclopentyloxy-4-methoxyphenyl)-5-oxa-6-aza-spiro[3.4]oct-6-ene (Compound No. 82),
3-(3-Cyclopentyloxy-4-methoxyphenyl)-1-oxa-2-aza-spiro[4.5]dec-2-ene (Compound No. 83),
3-(3-Cyclopentyloxy-4-methoxy-phenyl)-1-oxa-2,7-diaza-spiro[4.4]non-2-ene-7-carboxylic acid tert-butyl ester (Compound No. 84),
Hydrochloride salt of 3-(3-cyclopentyloxy-4-methoxyphenyl)-1-oxa-2,7-diaza-spiro[4.4]non-2-ene (Compound No. 85),
its pharmaceutically acceptable salts, enantiomers, or diastereomers.

6. A pharmaceutical composition comprising a therapeutically effective amount of a compound of claim 1 or 5 together with a pharmaceutically acceptable carrier, excipient or diluent.

* * * * *